(12) United States Patent
Salic et al.

(10) Patent No.: US 9,212,381 B2
(45) Date of Patent: Dec. 15, 2015

(54) METHODS AND COMPOSITIONS FOR LABELING POLYPEPTIDES

(71) Applicant: President and Fellows of Harvard College, Cambridge, MA (US)

(72) Inventors: Adrian Salic, Cambridge, MA (US); Jing Liu, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/673,296

(22) Filed: Nov. 9, 2012

(65) Prior Publication Data

US 2013/0122535 A1    May 16, 2013

Related U.S. Application Data

(60) Provisional application No. 61/558,107, filed on Nov. 10, 2011.

(51) Int. Cl.

| | |
|---|---|
| *C07D 473/34* | (2006.01) |
| *C12Q 1/02* | (2006.01) |
| *C07H 19/16* | (2006.01) |
| *G01N 33/533* | (2006.01) |
| *G01N 33/68* | (2006.01) |
| *A61K 49/00* | (2006.01) |

(52) U.S. Cl.
CPC .............. *C12Q 1/02* (2013.01); *A61K 49/0052* (2013.01); *A61K 49/0056* (2013.01); *C07D 473/34* (2013.01); *C07H 19/16* (2013.01); *G01N 33/533* (2013.01); *G01N 33/68* (2013.01); *G01N 2500/10* (2013.01)

(58) Field of Classification Search
USPC ................................................. 544/276, 277
See application file for complete search history.

(56) References Cited

U.S. PATENT DOCUMENTS

| | | | |
|---|---|---|---|
| 5,539,517 | A | 7/1996 | Cabib et al. |
| 5,790,727 | A | 8/1998 | Dhadwal et al. |
| 5,846,708 | A | 12/1998 | Hollis et al. |
| 5,880,473 | A | 3/1999 | Ginestet |
| 5,922,617 | A | 7/1999 | Wang et al. |
| 5,943,129 | A | 8/1999 | Hoyt et al. |
| 6,049,380 | A | 4/2000 | Goodwin et al. |
| 6,054,279 | A | 4/2000 | Nadeau et al. |
| 6,055,325 | A | 4/2000 | Garini et al. |
| 6,066,459 | A | 5/2000 | Garini et al. |
| 6,140,044 | A | 10/2000 | Besemer et al. |
| 6,143,495 | A | 11/2000 | Lizardi et al. |
| 6,191,425 | B1 | 2/2001 | Imai |
| 6,252,664 | B1 | 6/2001 | Barbera-Guillem |
| 6,261,776 | B1 | 7/2001 | Pirrung et al. |
| 6,294,331 | B1 | 9/2001 | Ried et al. |
| 2008/0108636 | A1* | 5/2008 | Honigberg et al. ...... 514/263.22 |

OTHER PUBLICATIONS

N. Doi, H. Takashima, M. Kinjo, K. Sakata, Y. Kawahashi, Y. Oishi, R. Oyama, E. Miyamoto-Sato, T. Sawasaki, Y. Endo, and H. Yanagawa, "Novel Fluorescence Labeling and High-Throughput Assay Technologies for In Vitro Analysis of Protein Interactions", Genome Research 2001, vol. 12, pp. 487-492.*
J.J. Jaffe, "Nucleoside analogs as antiparasitic agents", Annals of the New York Academy of Sciences 1975, vol. 255, pp. 306-316.*
Nicholson, Allen W. FEBS Letters. vol. 90, No. 2 (1978) 203-208.*
Invitrogen "Click-iT® Metabolic Labeling Reagents for Proteins". Molecular Probes® (2009) 1-10.*
Best, Michael. Biochemistry, 2009, 48, 6571-6584.*
Reusch, William. "Proteins, Peptitdes & Amino Acids". (2013) 1-10. <https://www2.chemistry.msu.edu/faculty/reusch/virttxtjml/proteins.htm>.*
Komori, Tadaaki. The Journal of Anitbiotics. vol. 38 No. 5 (1985) 1182-1203.*
Adams et al., Development of the proteasome inhibitor Velcade (Bortezomib). Cancer Invest. 2004;22(2):304-11.
Agard et al., A strain-promoted [3+2] azide-alkyne cycloaddition for covalent modification of biomolecules in living systems. J Am Chem Soc. Nov. 24, 2004;126(46):15046-7. Erratum in: J Am Chem Soc. Aug. 10, 2005;127(31):11196.
Aguilera et al., Permeabilizing action of an antimicrobial lactoferricin-derived peptide on bacterial and artificial membranes. FEBS Lett. Dec. 3, 1999;462(3):273-7.
Aikens et al., Solid-state imagers for microscopy. Methods Cell Biol. 1989;29:291-313.
Al-Sa'Doni et al., Neocuproine, a selective Cu(I) chelator, and the relaxation of rat vascular smooth muscle by S-nitrosothiols. Br J Pharmacol. Jul. 1997;121(6):1047-50.
Andrews et al., Protein synthesis by membrane-bound and free ribosomes of secretory and non-secretory tissues. Biochem J. Feb. 1971;121(4):683-94.
Baek et al., The impact of microRNAs on protein output. Nature. Sep. 4, 2008;455(7209):64-71. Epub Jul. 30, 2008.
Bagnati et al., Cu(I) availability paradoxically antagonizes antioxidant consumption and lipid peroxidation during the initiation phase of copper-induced LDL oxidation. Biochem Biophys Res Commun. Dec. 18, 1998;253(2):235-40.

(Continued)

*Primary Examiner* — Golam M M Shameem
*Assistant Examiner* — Laura Daniel
(74) *Attorney, Agent, or Firm* — Wolf, Greenfield & Sacks, P.C.

(57) ABSTRACT

Synthesis of many proteins is tightly controlled at the level of translation and plays an essential role in fundamental processes such as cell growth and proliferation, signaling, differentiation or death. Methods that allow imaging and identification of nascent proteins allow for dissecting regulation of translation, both spatially and temporally, including in whole organisms. Described herein are robust chemical methods for imaging and affinity-purifying nascent polypeptides in cells and in animals, based on puromycin analogs. Puromycin analogs of the present invention form covalent conjugates with nascent polypeptide chains, which are rapidly turned over by the proteasome and can be visualized and specifically captured by a bioorthogonal reaction (e.g., [3+2] cycloaddition). The methods of the present invention have broad applicability for imaging protein synthesis and for identifying proteins synthesized under various physiological and pathological conditions in vivo.

35 Claims, 10 Drawing Sheets

(56) References Cited

OTHER PUBLICATIONS

Beatty et al., Fluorescence visualization of newly synthesized proteins in mammalian cells. Angew Chem Int Ed Engl. Nov. 13, 2006;45(44):7364-7.

Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.

Bussing et al., Expression of mitochondrial Apo2.7 molecules and caspase-3 activation in human lymphocytes treated with the ribosome-inhibiting mistletoe lectins and the cell membrane permeabilizing viscotoxins. Cytometry. Oct. 1, 1999;37(2):133-9.

Cheung et al., Making and reading microarrays. Nat Genet. Jan. 1999;21(1 Suppl):15-9.

De Man et al., Neocuproine potentiates the activity of the nitrergic neurotransmitter but inhibits that of S-nitrosothiols. Eur J Pharmacol. Sep. 24, 1999;381(2-3):151-9.

Dieterich et al., Selective identification of newly synthesized proteins in mammalian cells using bioorthogonal noncanonical amino acid tagging (BONCAT). Proc Natl Acad Sci U S A. Jun. 20, 2006;103(25):9482-7. Epub Jun. 12, 2006.

Dirksen et al., Rapid oxime and hydrazone ligations with aromatic aldehydes for biomolecular labeling. Bioconjug Chem. Dec. 2008;19(12):2543-8.

Divane et al., Rapid prenatal diagnosis of aneuploidy from uncultured amniotic fluid cells using five-colour fluorescence in situ hybridization. Prenat Diagn. Nov. 1994;14(11):1061-9.

Eckermann et al., Peptide-bond formation on the ribosome. A comparison of the acceptor-substrate specificity of peptidyl transferase in bacterial and mammalian ribosomes using puromycin analogues. Eur J Biochem. Feb. 1, 1974;41(3):547-54.

Foldes-Papp et al., Laser scanning confocal fluorescence microscopy: an overview. Int Immunopharmacol. Dec. 2003;3(13-14):1715-29.

Gocmen et al., Effect of neocuproine, a selective Cu(I) chelator, on nitrergic relaxations in the mouse corpus cavernosum. Eur J Pharmacol. Oct. 13, 2000;406(2):293-300.

Goldberg, Degradation of abnormal proteins in *Escherichia coli* (protein breakdown-protein structure-mistranslation-amino acid analogs-puromycin). Proc Natl Acad Sci U S A. Feb. 1972;69(2):422-6.

Goncalves et al., The use of permeabilized cells to assay protein phosphorylation and catecholamine release. Neurochem Res. Jun. 2000;25(6):885-94.

Hansen et al., Complex environment of nascent polypeptide chains. J Biol Chem. Oct. 28, 1994;269(43):26610-3.

Harvath, Overview of fluorescence analysis with the confocal microscope. Methods Mol Biol. 1999;115:149-58.

Hiraoka et al., The use of a charge-coupled device for quantitative optical microscopy of biological structures. Science. Oct. 2, 1987;238(4823):36-41.

Issacs et al., Cotranslational assembly of myosin heavy chain in developing cultured skeletal muscle. Proc Natl Acad Sci U S A. Sep. 1987;84(17):6174-8.

Jalal et al., Prenatal detection of aneuploidy by directly labeled multicolored probes and interphase fluorescence in situ hybridization. Mayo Clin Proc. Feb. 1998;73(2):132-7.

Kiick et al., Incorporation of azides into recombinant proteins for chemoselective modification by the Staudinger ligation. Proc Natl Acad Sci U S A. Jan. 8, 2002;99(1):19-24. Epub Dec. 18, 2001.

Lecuyer et al., Global analysis of mRNA localization reveals a prominent role in organizing cellular architecture and function. Cell. Oct. 5, 2007;131(1):174-87.

Lee et al., Puromycin analogues. Effect of aryl-substituted puromycin analogues on the ribosomal peptidyltransferase reaction. J Med Chem. Mar. 1981;24(3):304-8.

Lemieux et al., A fluorogenic dye activated by the staudinger ligation. J Am Chem Soc. Apr. 23, 2003;125(16):4708-9.

Lewis et al., Click chemistry in situ: acetylcholinesterase as a reaction vessel for the selective assembly of a femtomolar inhibitor from an array of building blocks. Angew Chem Int Ed Engl. Mar. 15, 2002;41(6):1053-7.

Link et al., Cell surface labeling of *Escherichia coli* via copper(I)-catalyzed [3+2] cycloaddition. J Am Chem Soc. Sep. 17, 2003;125(37):11164-5.

Liu et al., Imaging protein synthesis in cells and tissues with an alkyne analog of puromycin. Proc Natl Acad Sci U S A. Jan. 10, 2012;109(2):413-8. Supporting Information included.

Nathans et al., Structural requirements for puromycin inhibition of protein synthesis. Nature. Mar. 16, 1963;197:1076-7.

Nathans, Inhibition of protein synthesis by puromycin. Fed Proc. Sep.-Oct. 1964;23:984-9.

Nathans, Puromycin inhibition of protein synthesis: incorporation of puromycin into peptide chains. Proc Natl Acad Sci U S A. Apr. 1964;51:585-92.

Pestka et al., Effect of puromycin analogues and other agents on peptidyl-puromycin synthesis on polyribosomes. Antimicrob Agents Chemother. Jul. 1973;4(1):37-43.

Prescher et al., Chemical remodelling of cell surfaces in living animals. Nature. Aug. 19, 2004;430(7002):873-7.

Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.

Salic et al., A chemical method for fast and sensitive detection of DNA synthesis in vivo. Proc Natl Acad Sci U S A. Feb. 19, 2008;105(7):2415-20. Epub Feb. 12, 2008.

Saxon et al., A "traceless" Staudinger ligation for the chemoselective synthesis of amide bonds. Org Lett. Jul. 13, 2000;2(14):2141-3.

Saxon et al., Cell surface engineering by a modified Staudinger reaction. Science. Mar. 17, 2000;287(5460):2007-10.

Selbach et al., Widespread changes in protein synthesis induced by microRNAs. Nature. Sep. 4, 2008;455:58-63. Epub Jul. 30, 2008.

Sletten et al., A bioorthogonal quadricyclane ligation. J Am Chem Soc. Nov. 9, 2011;133(44):17570-3. Epub Oct. 17, 2011.

So et al., Two-photon excitation fluorescence microscopy. Annu Rev Biomed Eng. 2000;2:399-429.

Sonenberg et al., Regulation of translation initiation in eukaryotes: mechanisms and biological targets. Cell. Feb. 20, 2009;136(4):731-45.

Stephens et al., Light microscopy techniques for live cell imaging. Science. Apr. 4, 2003;300(5616):82-6.

Tornoe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

Vanin et al., Structure-activity relationships of puromycin analogues on *Escherichia coli* polysomes. FEBS Lett. Mar. 15, 1974;40(1):124-6.

Wang et al., Bioconjugation by copper(I)-catalyzed azide-alkyne [3+2] cycloaddition. J Am Chem Soc. Mar. 19, 2003;125(11):3192-3.

Wharton et al., Abnormal proteins of shortened length are preferentially degraded in the cytosol of cultured MRC5 fibroblasts. FEBS Lett. Mar. 12, 1984;168(1):134-8.

Van Hest et al., Efficient Incorporation of Unsaturated Methionine Analogues into Proteins in Vivo. *J Am Chem Soc*. 2000;122 (7):1282-1288.

\* cited by examiner

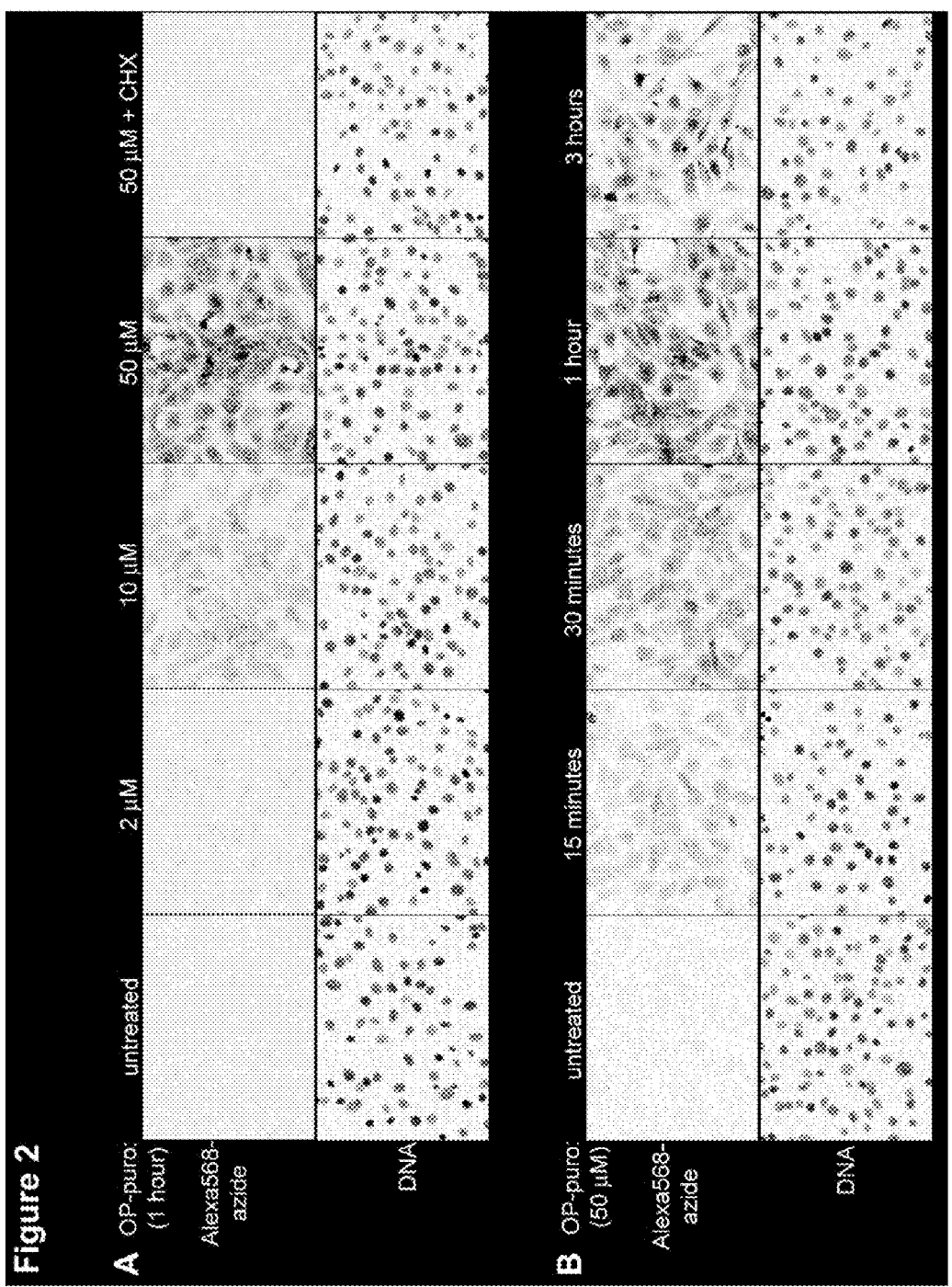

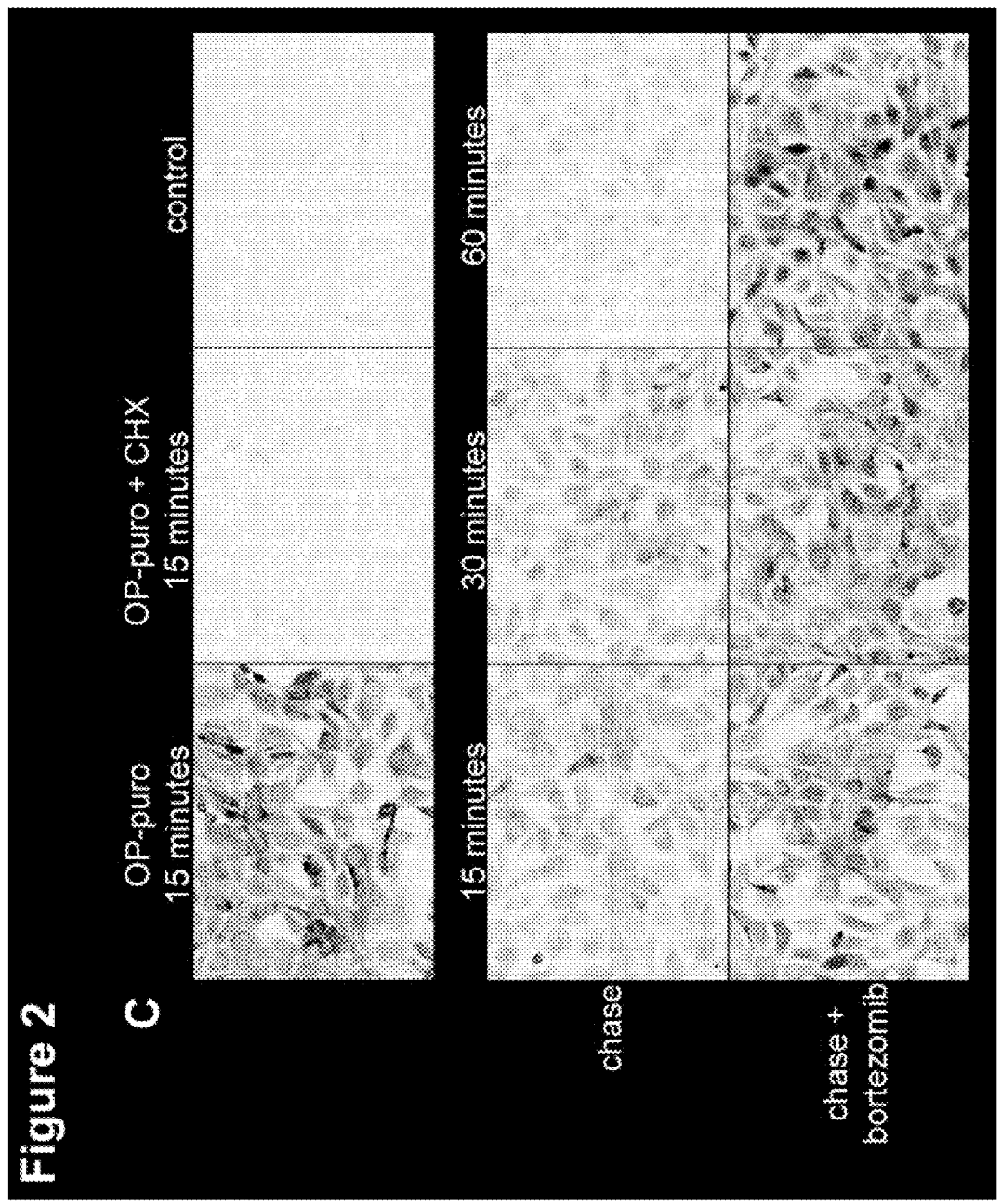

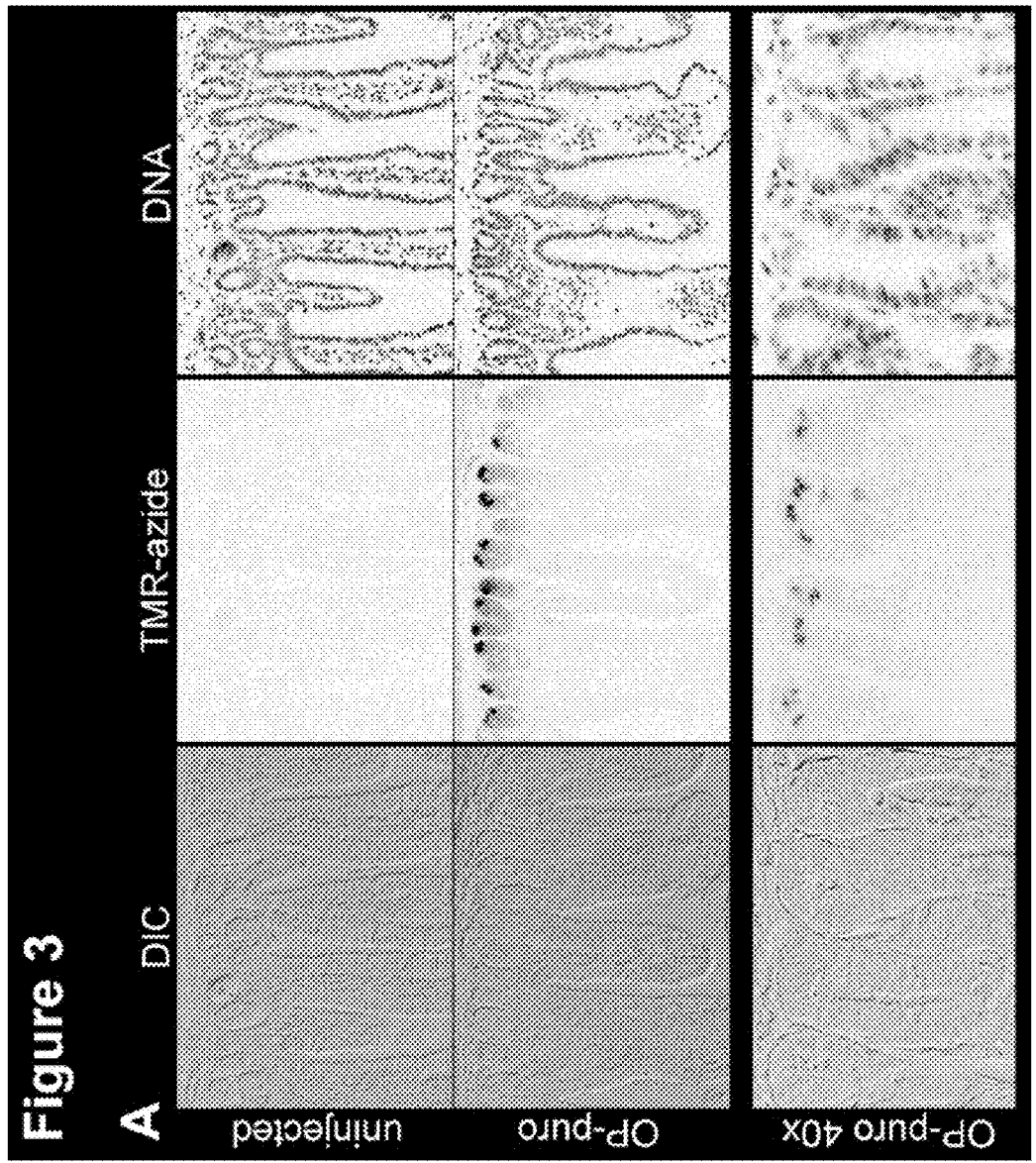

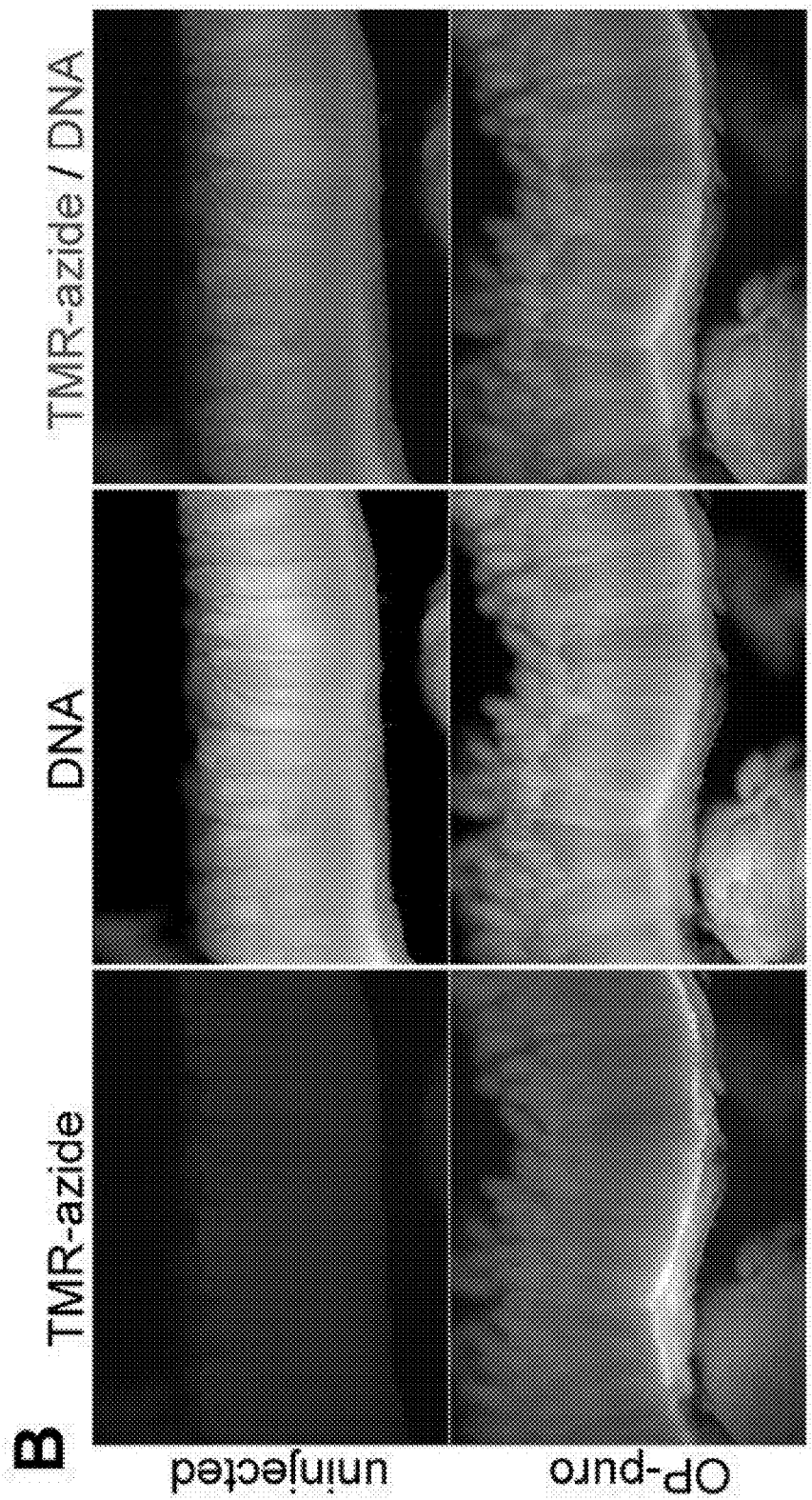

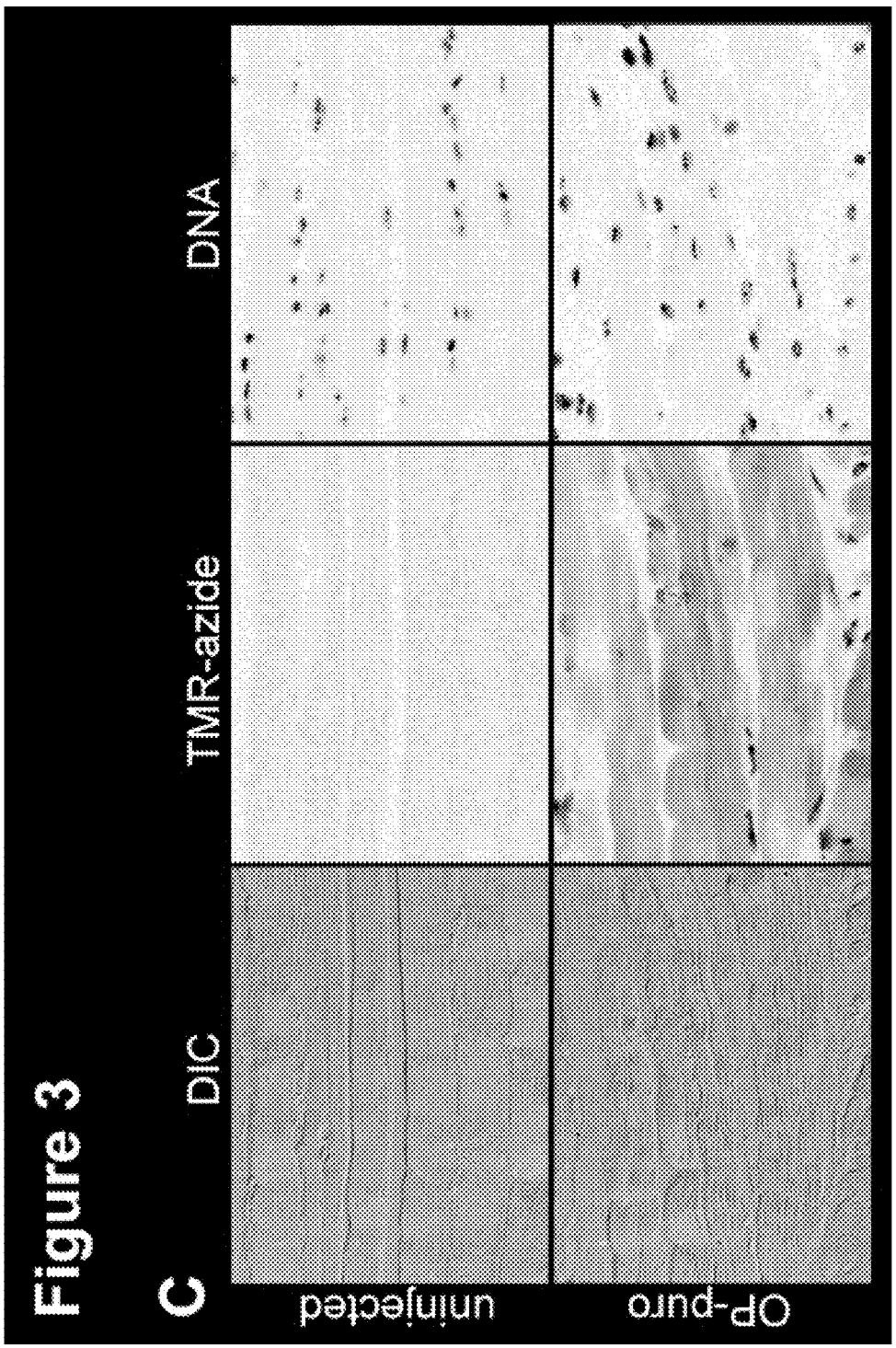

METHODS AND COMPOSITIONS FOR LABELING POLYPEPTIDES

RELATED APPLICATION

The present application claims priority under 35 U.S.C. §119(e) to U.S. provisional patent application, U.S. Ser. No. 61/558,107, filed Nov. 10, 2011, which is incorporated herein by reference.

BACKGROUND OF THE INVENTION

The entire set of cellular proteins is generated through translation of mRNAs by ribosomes. The identity and amount of the proteins that a cell synthesizes are critical parameters in determining the physiological state of the cell. Protein synthesis is frequently not proportional to mRNA levels, mainly because translation is often tightly regulated; indeed, many critical controls in gene expression occur at the level of translation (Sonnenberg et al., *Cell* 136(4):731-745 (2009); Selbach et al., *Nature* 455(7209):58-63 (2008); Baek et al., *Nature* 455(7209):64-71 (2008)). Under specific conditions (such as heat shock, starvation, availability of iron, etc.), translational controls ensure that synthesis of specific cellular proteins is quickly turned on or off. Translational controls are particularly prominent in systems in which transcription is inhibited, such as in early embryonic development before the onset of zygotic transcription. Furthermore, translation of many proteins is spatially localized, as underscored by the finding that the majority of mRNAs in *Drosophila* embryos display distinct subcellular patterns (Lecuyer et al., *Cell* 131(1):174-187 (2007)).

Understanding how gene expression is regulated at the level of translation, spatially and temporally, requires tools for visualizing and identifying nascent polypeptide chains. The current method used for this purpose relies on the biosynthetic incorporation of azide- or alkyne-bearing methionine (Met) analogs such as azidohomoalanine (Aha) (Dieterich et al., *Proc. Natl. Acad. Sci. USA* 103(25):9482-9487 (2006); Link et al., *J. Am. Chem. Soc.* 125(37):11164-11165 (2003)) or homopropargylglycine (Hpg) (Beatty et al., *Angew. Chem. Int. Ed. Engl.* 41(14):2596-2599 (2002)). The resulting azide or alkyne-labeled proteins can be detected by copper(I)-catalyzed azide-alkyne cycloaddition (CuAAC) (Rostovtsev et al., *Angew Chem. Intl. Ed. Engl.* 41(14):2596-2599 (2002); Tornoe et al., *J. Org. Chem.* 67(9):3057-3064 (2002); Wang et al., *J. Am. Chem. Soc.* 125(11):3192-3193 (2003)) with reagents for fluorescence detection (Beatty et al., *Angew. Chem. Int. Ed. Engl.* 41(14):2596-2599 (2002)) or for affinity purification and identification by mass spectrometry (Dieterich et al., *Proc. Natl. Acad. Sci. USA* 103(25):9482-9487 (2006)). Though simple and robust, this method has a number of drawbacks. Cells prefer Met over Aha or Hpg by a factor of about 500 (Beatty et al., *Angew. Chem. Int. Ed. Engl.* 41(14):2596-2599 (2002)), which means cultured cells need to be labeled with Aha or Hpg in Met-free media; this limitation precludes the use of Aha and Hpg to study protein synthesis in whole animals. To be incorporated into proteins, Aha and Hpg need to be activated as aminoacyl-tRNAs, a step which limits the temporal resolution of this method. Finally, this method generates full-length Aha- or Hpg-labeled proteins, not nascent polypeptide chains. Improved labeling techniques are needed for the study of nascent proteins in vivo, in particular methods that are rapid, sensitive, and work well in whole organisms.

SUMMARY OF THE INVENTION

Synthesis of many proteins is tightly controlled at the level of translation and plays an essential role in fundamental processes such as cell growth, proliferation, signaling, differentiation, and death. Methods that allow imaging and identification of nascent proteins allow for studying regulation of translation, both spatially and temporally, including in whole organisms. Described herein are robust chemical methods and systems for imaging and affinity-purifying nascent polypeptides in cells and in animals based on puromycin analogs. Puromycin analogs of the present invention form covalent conjugates with nascent polypeptide chains, which are rapidly turned over by the proteasome and can be visualized and specifically captured by a bioorthogonal reaction (e.g., [3+2] cycloaddition, Staudinger ligation, tetrazine ligation). The methods of the present invention have broad applicability for imaging protein synthesis and for identifying proteins synthesized under various physiological and pathological conditions in vivo and in vitro.

In one aspect, the present invention provides puromycin analogs of Formula (I):

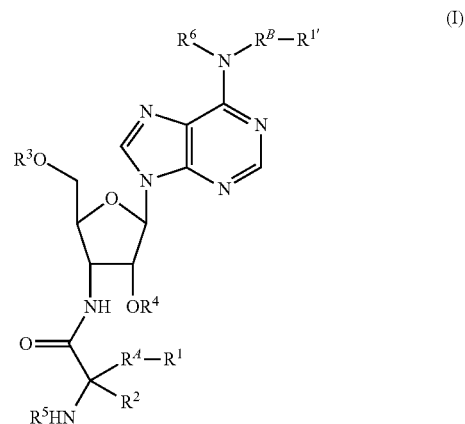

or a salt thereof, wherein $R^A$, $R^B$, $R^1$, $R^{1'}$, $R^2$, $R^3$, $R^4$, $R^5$, and $R^6$ are as defined herein.

In some embodiments, a puromycin analog according to the present invention is of Formula (II):

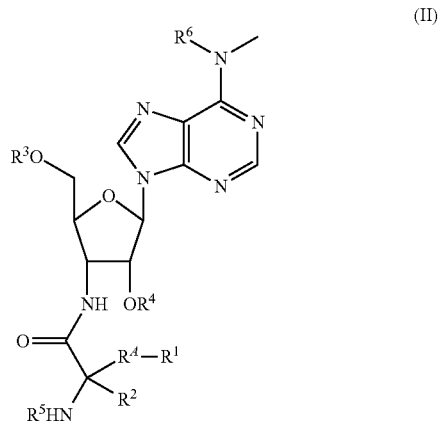

or a salt thereof, wherein $R^A$, $R^1$, $R^2$, $R^3$, $R^4$, $R^5$, and $R^6$ are as defined herein.

In some embodiments, a puromycin analog according to the present invention is of Formula (III):

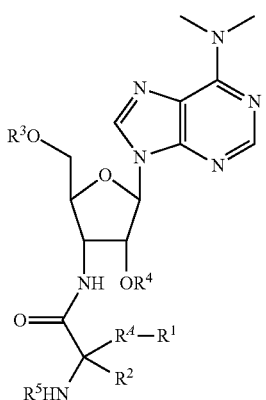

or a salt thereof, wherein $R^A$, $R^1$, $R^2$, $R^3$, $R^4$, and $R^5$ are as defined herein.

In some embodiments, a puromycin analog according to the present invention is of Formula (III-a):

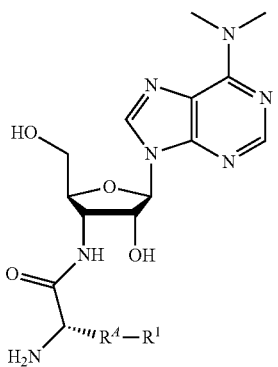

or a salt thereof, wherein $R^A$ and $R^1$ is as defined herein.

In certain embodiments, the present invention provides

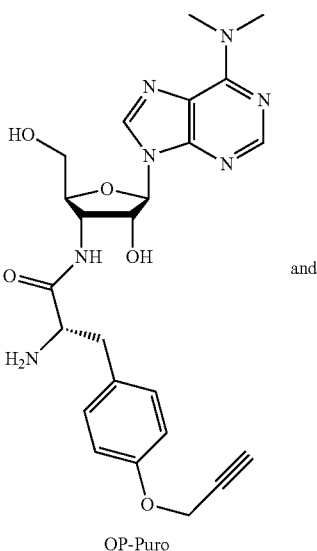

OP-Puro

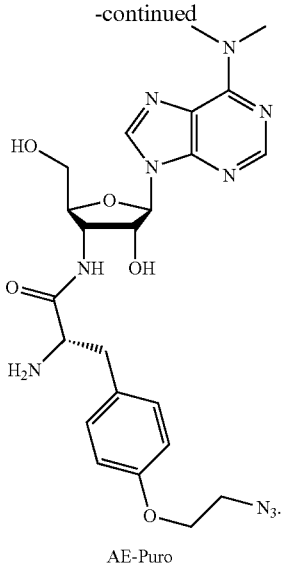

AE-Puro

In another aspect, the present invention provides methods of labeling polypeptides. In certain embodiments, a method of the present invention includes a method of labeling a polypeptide comprising providing a polypeptide-puromycin analog conjugate comprising a first reactive group; and contacting the polypeptide-puromycin analog conjugate with a compound comprising a second reactive group and a label, such that a bioorthogonal reaction occurs between the first and second reactive groups. In certain embodiments, a method of the present invention includes a method of labeling a polypeptide comprising providing a polypeptide-puromycin analog conjugate comprising a first reactive unsaturated group; and contacting the polypeptide-puromycin analog conjugate with a compound comprising a second reactive unsaturated group and a label, such that a [3+2] cycloaddition occurs between the first and second unsaturated groups. In certain embodiments, the first reactive unsaturated group is an alkyne and the second reactive unsaturated group is an azide. In certain other embodiments, the first reactive unsaturated group is an azide and the second reactive unsaturated group is an alkyne. In some embodiments, the present invention provides polypeptides labeled by the methods described herein. In some embodiments, the method of labeling a polypeptide takes place in a cell. In some embodiments, the method of labeling a polypeptide takes place in a whole organism.

The present invention also provides methods of measuring protein synthesis in a cell or organism. For example, in certain embodiments, the present invention provides methods of measuring protein synthesis in a cell or organism comprising contacting a cell or organism with an effective amount of a puromycin analog comprising a first reactive group, such that the puromycin analog is covalently bound to the C-terminus of one or more polypeptides in the cell to form one or more polypeptide-puromycin analog conjugates; contacting the cell or organism with a compound comprising a second reactive group and a label, such that a bioorthogonal reaction occurs between the first and second reactive groups; and determining the amount of labeled protein in the cell to measure protein synthesis. In certain embodiments, the present invention provides methods of measuring protein synthesis in a cell comprising contacting a cell with an effective amount of a puromycin analog comprising a first reactive unsaturated group, such that the puromycin analog is covalently bound to the C-terminus of one or more polypeptides in the cell to form one or more polypeptide-puromycin analog conjugates; contacting the cell with a compound comprising a second reactive unsaturated group and a label, such that a [3+2] cycloaddition occurs between the first and second reactive unsaturated groups; and determining the amount of labeled protein in the cell to measure protein synthesis. In certain embodiments, the present invention provides methods of measuring protein synthesis in an organism comprising administering to an organism an effective amount of a puromycin analog comprising a first reactive unsaturated group, such that the puromycin analog is covalently bound to the C-terminus of one or more polypeptides in the organism to form one or more polypeptide-puromycin analog conjugates; contacting at least one cell of the organism with a compound comprising a second reactive unsaturated group and a label, such that a [3+2] cycloaddition occurs between the first and second reactive unsaturated groups; and determining the amount of labeled protein in the at least one cell in order to measure protein synthesis in the organism.

In another aspect, the present invention also provides screening methods. For example, in certain embodiments, the present invention provides a method of identifying an agent that perturbs protein synthesis comprising: contacting a cell or organism with a test agent; contacting the cell or organism with an effective amount of a puromycin analog comprising a first reactive group, such that the puromycin analog is covalently bound to the C-terminus of nascent polypeptides in the cell; contacting the cell or organism with a compound comprising a second reactive group and a label, such that a bioorthogonal reaction occurs between the first and second reactive groups; determining the amount of label incorporated into nascent polypeptides, wherein the amount of label indicates the extent of protein synthesis; and identifying the test agent as an agent that perturbs cellular proliferation if the amount of label incorporated into nascent polypeptides is less than or greater than the amount of label measured in a control in which a cell is not contacted with the test agent. In certain embodiments, the present invention provides a method of identifying an agent that perturbs protein synthesis comprising: contacting a cell with a test agent; contacting the cell with an effective amount of a puromycin analog comprising a first reactive unsaturated group, such that the puromycin analog is covalently bound to the C-terminus of nascent polypeptides in the cell; contacting the cell with a compound comprising a second reactive unsaturated group and a label, such that a [3+2] cycloaddition occurs between the first and second reactive unsaturated groups; determining the amount of label incorporated into nascent polypeptides, wherein the amount of label indicates the extent of protein synthesis; and identifying the test agent as an agent that perturbs cellular proliferation if the amount of label incorporated into nascent polypeptides is less than or greater than the amount of label measured in a control in which a cell is not contacted with the test agent. In certain embodiments, the present invention provides methods of identifying an agent that perturbs protein synthesis in an organism comprising exposing an organism to a test agent; administering to the organism an effective amount of a puromycin analog comprising a first reactive unsaturated group, such that the puromycin analog is covalently bound to the C-terminus of nascent polypeptides in the organism; contacting at least one cell of the organism with a compound comprising a second reactive unsaturated group and a label, such that a [3+2] cycloaddition occurs between the first and second reactive unsaturated groups; determining the amount of label incorporated into the nascent polypeptides in at least one cell, wherein the amount of label indicates the extent of protein synthesis; and identifying the test agent as an agent that perturbs cellular proliferation if the amount of label incorporated into nascent polypeptides is less than or greater than the amount of label measured in a control in which an organism is not administered the test agent.

The present invention also provides methods of isolating and/or identifying nascent polypeptides. For example, in certain embodiments, the present invention provides a method of identifying a nascent polypeptide comprising contacting a cell with an effective amount of a puromycin analog comprising a first reactive group, such that the puromycin analog is covalently bound to the C-terminus of a nascent polypeptide in the cell to form a polypeptide-puromycin analog conjugate; contacting the cell with a compound comprising a second reactive group and an affinity label, such that a bioorthogonal reaction occurs between the first and second reactive groups to form an affinity-labeled polypeptide; and affinity purifying the affinity-labeled polypeptide. In certain embodiments, the present invention provides a method of identifying a nascent polypeptide comprising contacting a cell with an effective amount of a puromycin analog comprising a first reactive unsaturated group, such that the puromycin analog is covalently bound to the C-terminus of a nascent polypeptide in the cell to form a polypeptide-puromycin analog conjugate; contacting the cell with a compound comprising a second reactive unsaturated group and an affinity label, such that a [3+2] cycloaddition occurs between the first and second reactive unsaturated groups to form an affinity-labeled polypeptide; and affinity purifying the affinity-labeled polypeptide. In other embodiments, the present invention provides a method of identifying a nascent polypeptide comprising contacting a cell with an effective amount of a puromycin analog comprising a first reactive group, such that the puromycin analog is covalently bound to the C-terminus of one or more nascent polypeptides in the cell to form one or more polypeptide-puromycin analog conjugates; contacting the cell with a solid support comprising a second reactive group, such that a bioorthogonal reaction occurs between the first and second reactive groups; and identifying the nascent polypeptide. In certain embodiments, the present invention provides a method of identifying a nascent polypeptide comprising contacting a cell with an effective amount of a puromycin analog comprising a first reactive unsaturated group, such that the puromycin analog is covalently bound to the C-terminus of one or more nascent polypeptides in the cell to form one or more polypeptide-puromycin analog conjugates; contacting the cell with a solid support comprising a second reactive unsaturated group, such that a [3+2] cycloaddition occurs between the first and second reactive unsaturated groups; and identifying the nascent polypeptide. In certain embodiments, a method of identifying further comprises cleaving a polypeptide from a surface.

In another aspect, the invention provides a kit comprising a puromycin analog of the present invention; and a compound comprising a label. In some embodiments, the invention provides a kit comprising a puromycin analog of the present invention comprising a first reactive unsaturated group; and a compound comprising a second reactive unsaturated group and a label. In some embodiments, the kit further comprises Cu(I). In some embodiments, the kit further comprises an aqueous medium. In some embodiments, the kit further comprises instructions for use. These and other aspects of the invention will be described in further detail in connection with the detailed description of the invention.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., a inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex mixtures of isomers.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The "enantiomeric excess" of a substance is a measure of how pure a desired enantiomer is relative to the undesired enantiomer. Enantiomeric excess is defined as the absolute difference between the mole fraction of each enantiomer which is most often expressed as a percent enantiomeric excess. For mixtures of diastereomers, there are analogous definitions and uses for "diastereomeric excess" and percent diastereomeric excess. For example, a sample with 70% of R isomer and 30% of S will have an enantiomeric excess of 40%. This can also be thought of as a mixture of 40% pure R with 60% of a racemic mixture (which contributes 30% R and 30% S to the overall composition).

The term "acyl," as used herein, refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes ($-CHO$), carboxylic acids ($-CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula ($-OR^i$), wherein $R^i$ is an optionally substituted acyl group, as defined herein, and the oxygen moiety is directly attached to the parent molecule.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6, or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2 R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to, aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CHF_2$; —$CH_2F$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties as defined herein may be attached via an alkyl or heteroalkyl moiety and thus also include -(alkyl)aryl, -(heteroalkyl) aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl) aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "aryloxy" refers to a "substituted hydroxyl" of the formula (—OR$^i$), wherein R$^i$ is an optionally substituted aryl group, as defined herein, and the oxygen moiety is directly attached to the parent molecule.

The terms "halo" and "halogen" as used herein refer to an atom selected from fluorine (fluoro, —F), chlorine (chloro, —Cl), bromine (bromo, —Br), and iodine (iodo, —I).

The term "heterocycle" is given its ordinary meaning in the art and refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary ($-NH_2$), secondary ($-NHR_x$), tertiary ($-NR_xR_y$), or quaternary ($-N^+R_xR_yR_z$) amine, where $R_x$, $R_y$, and $R_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, —O-aryl.

The term "alkoxyalkyl" refers to an alkyl group substituted with at least one alkoxy group (e.g., one, two, three, or more, alkoxy groups). For example, an alkoxyalkyl group may be —($C_{1-6}$-alkyl)-O—($C_{1-6}$-alkyl), optionally substituted. In some cases, the alkoxyalkyl group may be optionally substituted with another alkyoxyalkyl group (e.g., —($C_{1-6}$-alkyl)-O—($C_{1-6}$-alkyl)-O—($C_{1-6}$-alkyl), optionally substituted.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

In certain embodiments, the substituent present on the nitrogen atom is an amino protecting group (also referred to herein as a "nitrogen protecting group"). Amino protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is a hydroxyl protecting group (also referred to herein as an "oxygen protecting group"). Hydroxyl protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Hydroxyl protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary hydroxyl protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "independently selected" is used herein to indicate that the R groups can be identical or different.

"Polypeptide," "peptide," or "protein": According to the present invention, a "polypeptide," "peptide," "protein" comprises a string of at least two amino acids linked together by peptide bonds. The terms "protein," "peptide," or "polypeptide" may be used interchangeably. Peptide may refer to an individual peptide or a collection of polypeptides. In certain embodiments, inventive peptides contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In some embodiments, a polypeptide according to the present invention is conjugated to a puromycin analog. In some embodiments, a polypeptide according to the present invention is conjugated to a puromycin analog that is attached to a detectable label.

As used herein, the term "reactive group" refers to a functional group capable of undergoing a bioorthogonal reaction. A "bioorthogonal reaction," as used herein, refers to a reaction that can be performed in a biological system without interfering with biological processes. A bioorthogonal reaction generally has a fast rate under physiological conditions and is inert to chemical functionalities found in vivo. Some examples of bioorthogonal reactions include, but are not limited to, [3+2] cycloadditions, Staudinger ligation, oxime ligation or hydrazone ligation (Dirksen et al., *Biocong. Chem.* 19:2543-2548 (2008)), inverse electron demand Diels-Alder (e.g., tetrazine ligation (Blackman et al., *J. Am. Chem. Soc.* 130:13518-13519 (2008))), and [2+2+2] cycloaddition (e.g., quadricyclane ligation (Sletten et al., *J. Am. Chem. Soc.* 133: 17570-17573 (2011))).

As used herein, the term "reactive unsaturated group" refers to a functional group containing atoms sharing more than one valence bond and that can undergo addition reactions, in particular cycloadditions. A reactive unsaturated group typically possesses at least one double or triple bond. In addition to the reactive moiety itself (e.g., double or triple bonded atoms), a reactive unsaturated group optionally comprises an alkyl or heteroalkyl linker moiety of 1-6 atoms.

The term "1,3-dipole" has herein its art understood meaning and refers to a molecule or functional group that is isoelectronic with the allyl anion and has four electrons in a it system encompassing the 1,3-dipole. 1,3-Dipoles generally have one or more resonance structures showing the characteristic 1,3-dipole. Examples of 1,3-dipoles include nitrile oxides, azides, diazomethanes, nitrones, and nitrile imines.

As used herein, the term "dipolarophile" has its art understood meaning and refers to a molecule or functional group that contains a π bond and that exhibits reactivity toward 1,3-dipoles. The reactivity of dipolarophiles depends both on the substituents present on the π bond and on the nature of the 1,3-dipole involved in the reaction. Dipolarophiles are typically alkenes or alkynes.

As used herein, the term "cycloaddition" refers to a chemical reaction in which two or more π-electron systems (e.g., unsaturated molecules or unsaturated parts of the same molecule) combine to form a cyclic product in which there is a net reduction of the bond multiplicity. In a cycloaddition, the π electrons are used to form new σ bonds. The product of a cycloaddition is called an "adduct" or "cycloadduct". Different types of cycloadditions are known in the art including, but not limited to, [3+2] cycloadditions and Diels-Alder reactions. [3+2] Cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Bertozzi et al., *J. Am. Chem. Soc.*, 2004, 126: 15046-15047).

The terms "labeled", "labeled with a detectable agent", and "labeled with a detectable moiety" are used herein interchangeably. "Label" and "detectable moiety" are also used interchangeably herein. When used in reference to a polypeptide, these terms specify that the polypeptide can be detected or visualized. In certain embodiments, a label is selected such that it generates a signal which can be measured and whose intensity is related to the amount of labeled polypeptides (e.g., in a sample). A label may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical or chemical means. Suitable labels include, but are not limited to, various ligands, radionuclides, fluorescent dyes, chemiluminescent agents, microparticles, enzymes, calorimetric labels, magnetic labels, and haptens.

The terms "fluorophore", "fluorescent moiety" and "fluorescent dye" are used herein interchangeably. They refer to a molecule which, in solution and upon excitation with light of appropriate wavelength, emits light back, generally at a longer wavelength. Numerous fluorescent dyes of a wide variety of structures and characteristics are suitable for use in the practice of the present invention. In choosing a fluorophore, it is often desirable that the molecule absorbs light and emits fluorescence with high efficiency (i.e., the fluorescent molecule has a high molar extinction coefficient at the excitation wavelength and a high fluorescence quantum yield, respectively) and is photostable (i.e., the fluorescent molecule does not undergo significant degradation upon light excitation within the time necessary to perform the detection).

As used herein, the term "effective amount" refers to the amount of a substance, compound, molecule, agent or composition that elicits the relevant response in a cell, a tissue, or an organism. For example, in the case of a puromycin analog administered to an organism, an effective amount of puromycin analog is an amount of puromycin analog that is conjugated to nascent polypeptides in one or more cell of the organism.

As used herein, the term "organism" refers to a living system that has or can develop the ability to act or function independently. An organism may be unicellular or multicellular. Organisms include humans, animals, plants, bacteria, protozoa, and fungi.

As used herein, the term "puromycin analog" refers to a compound having the general aminonucleoside core structure of puromycin that is capable of conjugating to the C-terminus of a polypeptide and is modified to include a reactive group capable of undergoing a bioorthogonal reaction. In certain embodiments, "puromycin analog" refers to a compound having the general aminonucleoside core structure of puromycin that is capable of conjugating to the C-terminus of a polypeptide and is modified to include a reactive unsaturated group, such as a 1,3-dipole or a dipolarophile. In some embodiments, a puromycin analog according to the present invention is of Formula (I) as described herein.

As used herein, the term "polypeptide-puromycin analog conjugate" refers to a polypeptide where a puromycin analog as described herein is covalently conjugated to the C-terminus.

The terms "detectable polypeptide" and "labeled polypeptide" are used interchangeably herein, and refer to a polypeptide-puromycin analog conjugate that has undergone a bioorthogonal reaction and is thereby attached to a label.

BRIEF DESCRIPTION OF THE DRAWINGS

FIG. 2 depicts imaging of nascent proteins in cultured cells with OP-puro. (A) Cultured NIH-3T3 cells were incubated for 1 hour in complete media supplemented with increasing concentrations of OP-puro, OP-puro and cycloheximide (CHX), or control vehicle. The cells were then fixed, stained by CuAAC with Alexa568-azide and imaged by fluorescence microscopy. A specific signal is observed in cells treated with OP-puro, which is proportional to the concentration of added OP-puro; this signal is abolished if protein translation is blocked with CHX (50 micrograms/mL), which dissociates ribosomes and thus prevents the formation of conjugates between nascent polypeptide chains and OP-puro. (B) Time course of OP-puro incorporation into nascent proteins. NIH-3T3 cells were incubated with OP-puro (50 microM, which is sufficient to completely block protein synthesis) for 14 varying amounts of time, after which OP-puro incorporation was imaged as in (A). The intensity of the OP-puro signal reaches a maximum after about 1 hour. (C) The nascent protein-OP-puro conjugates are unstable and are cleared from cells in a proteasome-dependent manner. NIH-3T3 cells were treated with 50 microM OP-puro for 15 minutes, followed by incubation in media without OP-puro, in the absence or presence of 5 microM of the proteasome inhibitor bortezomib. Parallel cultures were fixed at the indicated times after removal of OP-puro, and nascent protein-OP-puro conjugates were imaged by CuAAC labelling using Alexa568-azide. The OP-puro conjugates have largely disappeared after 1 hour but are completely stabilized by proteasome inhibition. Untreated cells and cells incubated for 15 minutes with OP-puro (50 microM) and CHX (50 micrograms/mL) served as negative controls.

FIG. 3 depicts the use of OP-puro to image protein synthesis in whole animals. One hundred microliters of a 20 mM OP-puro solution in PBS or PBS alone (negative control) were injected intraperitoneally into mice. Organs were harvested 1 hour later, fixed in formalin, and stained using CuAAC with tetramethylrhodamine (TMR)-azide, either after paraffin sectioning or whole mount. (A) Section through mouse small intestine showing intestinal vili sectioned longitudinally. OP-puro stains strongly the cells in the crypts (particularly Paneth cells) and the cells at the base of the villi. Bottom panels show a higher magnification (40× objective) view of the intestinal crypts in an OP-puro-injected mouse. Note the intense staining of the secretory granules characteristic of Paneth cells. (B) Whole mount staining of mouse small intestine, showing the localization of the OP-puro stain in the crypts. Protein-OP-puro conjugates were detected with TMR-azide (red), while nuclear DNA was stained with Oli-Green (green). (C) OP-puro incorporation into striated muscle fibers. Paraffin sections of muscle were stained as in (A). Sarcomeres are strongly stained with OP-puro, likely because some protein-OP-puro conjugates are functional and are properly assembled into sarcomeres. Images of OP-puro staining of other surveyed mouse tissues (spleen, kidney, liver) are shown in FIG. 4.

DETAILED DESCRIPTION OF CERTAIN EMBODIMENTS

Figure 1:
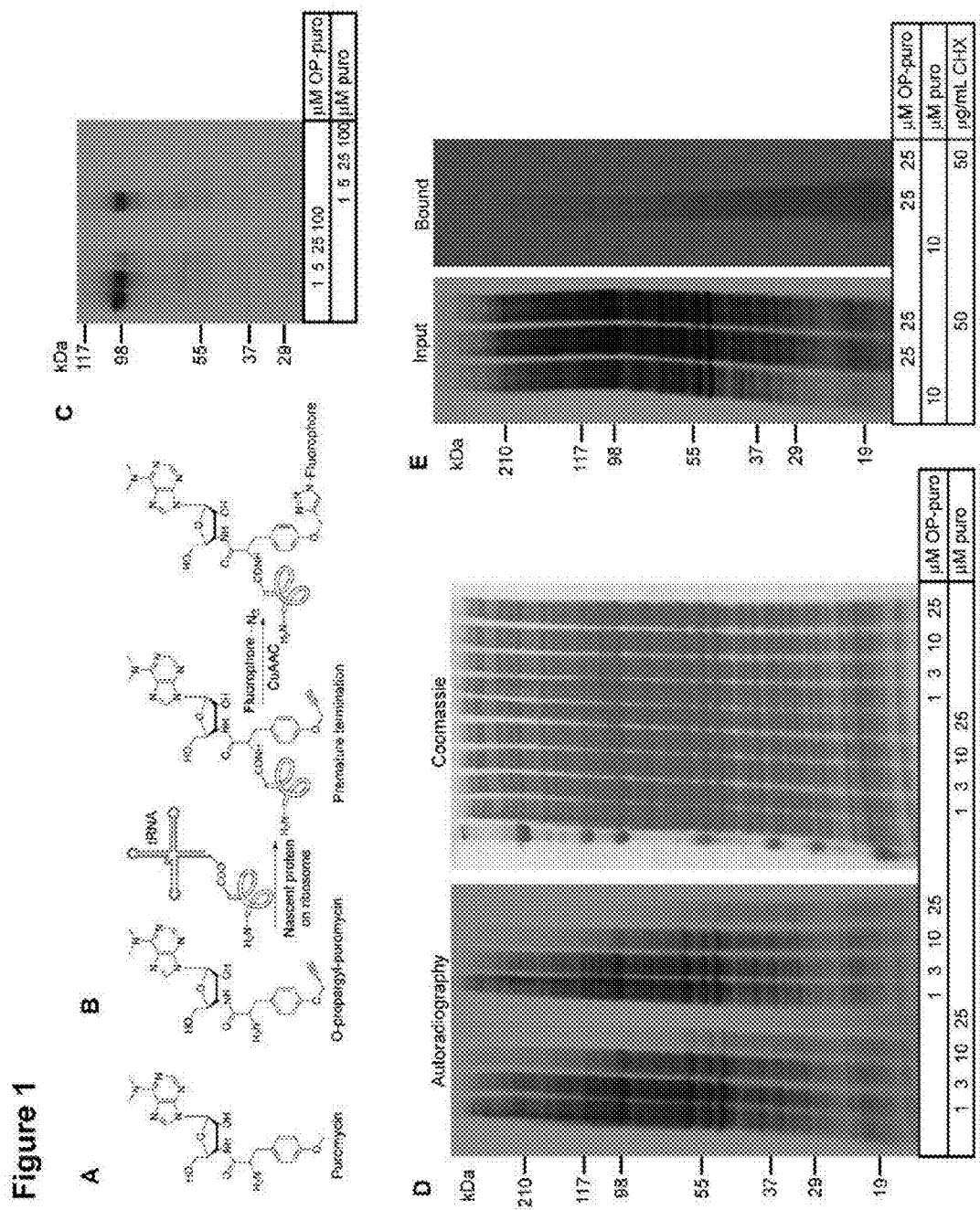
FIG. 1 shows that O-propargyl-puromycin (OP-puro), an alkyne puromycin (puro) analog, is a potent protein synthesis inhibitor. (A) Structure of puro and the analog OP-puro, which bears a terminal alkyne group. (B) Schematic of OP-puro incorporation into nascent polypeptide chains on translating ribosomes. The prematurely terminated polypeptides are subsequently detected by copper(I)-catalyzed azide-alkyne cycloaddition (CuAAC) using a fluorescent azide. (C) Inhibition of protein translation in vitro by puro and OP-puro. A $^{35}$S-methionine-labeled protein (a GFP fusion of mouse Suppressor of Fused) was generated by translation in rabbit reticulocyte lysates, in the absence or presence of varying concentrations of puro and OP-puro. The translation reactions were separated by SDS-PAGE, and the translated protein was visualized by autoradiography. OP-puro inhibits protein synthesis in a dose-dependent manner. (D) Inhibition of protein translation in cultured cells by puro and OP-puro. Human embryonic kidney 293T cells were incubated in methionine-free media supplemented with $^{35}$S-methionine, in the absence or presence of varying concentrations of puro and OP-puro. Total cell lysates were analyzed by SDS-PAGE, followed by autoradiography, to measure bulk protein translation. The gel was also stained with Coomassie Blue, to demonstrate equal protein loading. (E) Formation of conjugates between OP-puro and nascent polypeptide chains. Cultured 293T cells were labeled with $^{35}$S-methionine as in D), in the presence of OP-puro, puro or OP-puro and the protein synthesis inhibitor, cycloheximide (CHX). Cellular lysates were reacted with biotin-azide under conditions for CuAAC, after which biotinylated molecules were purified on streptavidin beads. Bound proteins were eluted, separated by SDS-PAGE, followed by autoradiography to detect nascent proteins.

The present invention provides methods and compositions for labeling polypeptides and for measuring protein synthesis and identifying nascent polypeptides both in vitro and in vivo.
Labeling of Polypeptides In some embodiments, labeling methods of the present invention generally include a bioorthogonal reaction between a first reactive group on a puromycin analog incorporated into a polypeptide and a second reactive group attached to a label. In some embodiments, labeling methods of the present invention generally include a [3+2] cycloaddition between a first reactive unsaturated group on a puromycin analog incorporated into a polypeptide and a second reactive unsaturated group attached to a label. An example of such a labeling method is schematically presented in FIG. 1B.

In certain embodiments, the present invention provides a method of labeling a polypeptide comprising providing a polypeptide-puromycin analog conjugate comprising a first reactive group; and contacting the polypeptide-puromycin analog conjugate with a compound comprising a second reactive group and a label, such that a bioorthogonal reaction occurs between the first and second reactive groups. In certain embodiments, the present invention provides a method of labeling a polypeptide comprising providing a polypeptide-puromycin analog conjugate comprising a first reactive unsaturated group; and contacting the polypeptide-puromycin analog conjugate with a compound comprising a second reactive unsaturated group and a label, such that a [3+2] cycloaddition occurs between the first and second unsaturated groups.
Puromycin Analogs Puromycin (puro) (FIG. 1A) is an aminonucleoside antibiotic that blocks protein synthesis in both prokaryotes and eukaryotes, by causing premature termination of nascent polypeptide chains. Puromycin mimics an aminoacyl-tRNA molecule and binds to the acceptor site of translating ribosomes, which leads to the formation of an amide bond between the C-terminus of the nascent polypeptide chain and the primary amine group of puromycin (Nathans, *Proc. Natl. Acad. Sci. USA* 51:585-592 (1964); Nathans, *Fed. Proc.* 23:984-989 (1964)). The polypeptide chain-puro conjugate is then released from the ribosome, followed by its quick, ubiquitin-dependent proteolysis (Goldberg, *Proc. Natl. Acad. Sci. USA* 69(2):422-426 (1972); Wharton et al., *FEBS Lett.* 168 (1):134-138 (1984)). The translation inhibition mechanism of puro has been exploited in the past to assay the rate of synthesis of specific proteins, using labeling with radioactive puro followed by immunoprecipitation with antibodies against the protein of interest (Issacs et al., *Proc. Natl. Acad. Sci. USA* 84(17):6174-6178 (1987)).

Puromycin analogs suitable for use in the practice of the methods of the present invention include any puromycin analog that contains a reactive group that can undergo a bioorthogonal reaction. In some embodiments, puromycin analogs suitable for use in the practice of the methods of the present invention include any puromycin analog that contains a reactive unsaturated group that can undergo a [3+2] cycloaddition. In other embodiments, puromycin analogs suitable for use in the practice of the methods of the present invention include any puromycin analog that contains a reactive group that can undergo a Staudinger ligation. In some embodiments, puromycin analogs suitable for use in the practice of the methods of the present invention include any puromycin analog that contains a reactive group that can undergo an inverse electron demand Diels-Alder reaction (e.g., tetrazine ligation), oxime addition, hydrazone addition, or [2+2+2] cycloaddition (e.g., quadricyclane ligation). In some embodiments, the reactive unsaturated group is carried by the amino acid side chain portion of the puromycin analog. An amino acid side chain can be any side chain of a natural or non-natural amino acid. For example, the side chain of phenylalanine is benzyl, the side chain of alanine is methyl, and the side chain of tyrosine is 4-hydroxybenzyl.

In certain embodiments, a reactive unsaturated group is a 1,3-dipole such as a nitrile oxide, an azide, a diazomethane, a nitrone, or a nitrile imine. In certain embodiments, the 1,3-dipole is an azide. Alternatively, a reactive unsaturated group can be a dipolarophile such as an alkene (e.g., vinyl, propylenyl, and the like) or an alkyne (e.g., ethynyl, propynyl, and the like). In certain embodiments, the dipolarophile is an alkyne, such as, for example, an ethynyl group or a propargyl group.

Methods for the preparation of puromycin analogs are known in the art. For example, see Pestka et al., *Antimicrob Agents Chemother* 4(1):37-43 (1973); Eckermann et al., *Eur J Biochem* 41(3):547-554 (1974); Vanin et al., *FEBS Lett* 40(1):124-126 (1974); Lee et al., *J Med Chem* 24(3):304-308 (1981).

In certain embodiments, a puromycin analog of the present invention is a compound of Formula (I):

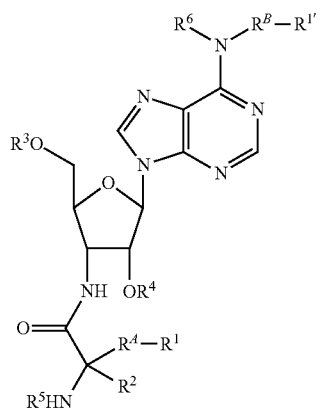

wherein
$R^A$ is a bond, or an optionally substituted group selected from aliphatic, heteroaliphatic, aryl, and heteroaryl, or a combination thereof;
$R^B$ is a bond or $C_{1-6}$ aliphatic;
$R^1$ is hydrogen or a reactive group capable of undergoing a bioorthogonal reaction;
$R^{1'}$ is hydrogen or a reactive group capable of undergoing a bioorthogonal reaction;
wherein $R^1$ and $R^{1'}$ are not simultaneously hydrogen;
$R^2$ is hydrogen or $C_{1-6}$ aliphatic;
$R^3$, $R^4$, and $R^5$ are each independently hydrogen or a protecting group;
$R^6$ is hydrogen or $C_{1-6}$ aliphatic;
or a salt thereof.

In certain embodiments, a puromycin analog of the present invention is a compound of Formula (II):

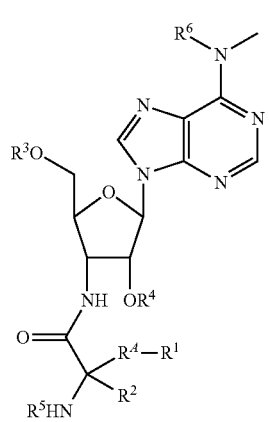

wherein
$R^A$ is a bond, or an optionally substituted group selected from aliphatic, heteroaliphatic, aryl, and heteroaryl, or a combination thereof;
$R^1$ is a reactive group capable of undergoing a bioorthogonal reaction;
$R^2$ is hydrogen or $C_{1-6}$ aliphatic;
$R^3$, $R^4$, and $R^5$ are each independently hydrogen or a protecting group;
$R^6$ is hydrogen or $C_{1-6}$ aliphatic;
or a salt thereof.

In certain embodiments, a puromycin analog of the present invention is a compound of Formula (III):

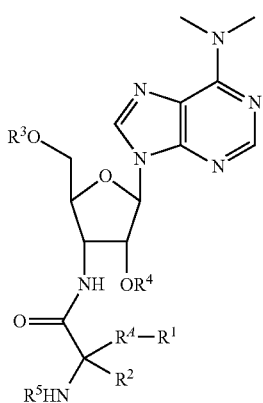

wherein
$R^A$ is a bond, or an optionally substituted group selected from aliphatic, heteroaliphatic, aryl, and heteroaryl, or a combination thereof;
$R^1$ is a reactive unsaturated group;
$R^2$ is hydrogen or $C_{1-6}$ aliphatic;
$R^3$, $R^4$, and $R^5$ are each independently hydrogen or a protecting group;
or a salt thereof.

In certain embodiments, a puromycin analog of the present invention is a compound of Formula (I-a), (II-a), or (III-a):

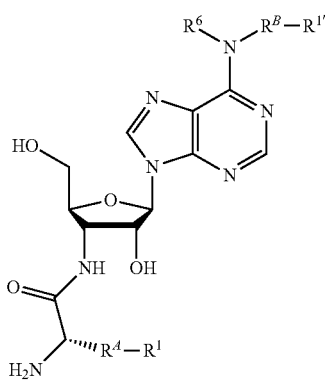

(I-a)

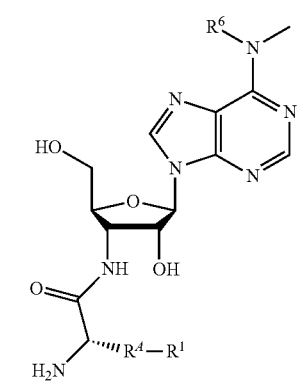

(II-a)

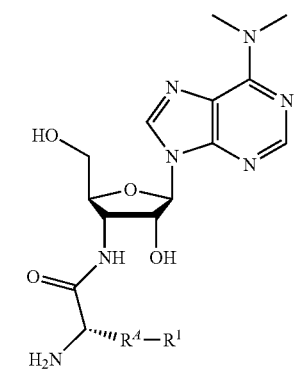

(III-a)

As defined generally above, $R^A$ is a bond, or an optionally substituted group selected from aliphatic, heteroaliphatic, aryl, and heteroaryl, or a combination thereof. In some embodiments, $R^A$ is a bond. It will be understood by one of ordinary skill in the art that when $R^A$ is a bond, $R^1$ is directly attached to the α-carbon of the molecule, geminal to $R^2$. In some embodiments, $R^A$ is a substituted aliphatic group. In other embodiments, $R^A$ is an unsubstituted aliphatic group. In some embodiments, $R^A$ is a substituted heteroaliphatic group. In other embodiments, $R^A$ is an unsubstituted heteroaliphatic group. In some embodiments, $R^A$ is a substituted aryl group. In other embodiments, $R^A$ is an unsubstituted aryl group. In some embodiments, $R^A$ is a substituted heteroaryl group. In other embodiments, $R^A$ is an unsubstituted heteroaryl group. In some embodiments, $R^A$ is a side chain of a naturally occurring amino acid. In some embodiments, $R^A$ is an aryl group. In some embodiments, $R^A$ is a combination of aliphatic, heteroaliphatic, aryl, and/or heteroaryl. For example, in some embodiments, $R^A$ is an -alkylaryl group. In certain embodiments, $R^A$ is a benzyl group. In some embodiments, $R^A$ is a tyrosine side chain. In some embodiments, $R^A$ is an alkyl group. In some embodiments, $R^A$ is a $C_{1-3}$ alkyl group. In certain embodiments, $R^A$ is $C_1$ or $C_2$ alkyl group. In some embodiments, $R^A$ is a heteroaryl group. In some embodiments, $R^A$ is a 5-6 membered heteroaryl having 1-3 heteroatoms selected from nitrogen, oxygen, and sulfur. In certain embodiments, $R^A$ is a 6-membered heteroaryl having 1-3 nitrogens. In certain embodiments, $R^A$ is a pyridyl group. In certain embodiments, —$R^A$—$R^1$ is selected from:

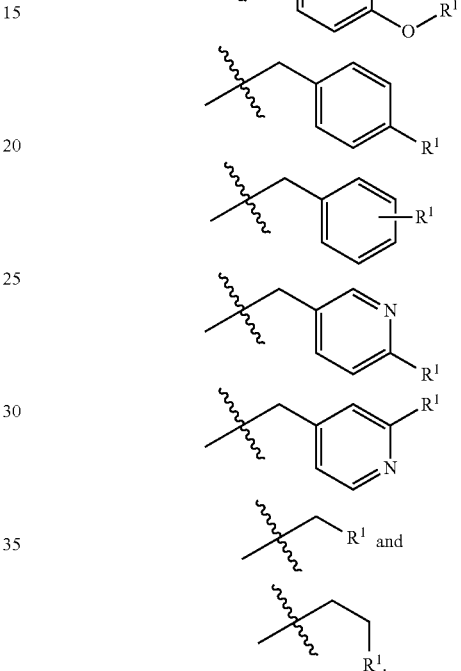

As defined generally herein, $R^1$ is hydrogen or a reactive group capable of undergoing a bioorthogonal reaction. In some embodiments, $R^1$ is hydrogen. In certain embodiments, $R^1$ is a reactive unsaturated group capable of undergoing a [3+2] cycloaddition (sometimes referred to as "click" chemistry). In certain embodiments, $R^1$ comprises an azide capable of undergoing a Staudinger ligation. In certain embodiments, $R^1$ comprises an aldehyde. In certain embodiments, $R^1$ comprises a tetrazine. In certain embodiments, $R^1$ comprises a trans-cyclooctene.

In certain embodiments, $R^1$ is a reactive unsaturated group. As defined generally herein, a reactive unsaturated group is a functional group containing atoms sharing more than one valence bond and that can undergo addition reactions, in particular cycloadditions. In addition to the reactive moiety itself (e.g., double or triple bonded atoms), a reactive unsaturated group optionally comprises an alkyl or heteroalkyl linker moiety of 1-6 atoms. For example, in some embodiments, a reactive unsaturated group is a group selected from propargyloxy, ethynyl, propargyl, homopropargyl, azidoethoxy, azido, azidomethyl, or azidoethyl. In some embodiments, $R^1$ is a reactive unsaturated group that possesses at least one double or triple bond. In some embodiments, a reactive unsaturated group comprises a dipolarophile. In certain embodiments, $R^1$ is a reactive unsaturated group that comprises a triple bond. In certain embodiments, $R^1$ comprises an alkyne. In certain other embodiments, $R^1$ comprises an alkene. In certain embodiments, $R^1$ comprises an ethynyl group. In certain embodiments, $R^1$ is an ethynyl or propargyl group. In other embodiments, $R^1$ is a reactive unsaturated group that comprises a 1,3-dipole. In certain embodiments, $R^1$ is a reactive unsaturated group that comprises a nitrile oxide, azide, diazomethane, nitrone, or nitrile imine. In certain embodiments, $R^1$ comprises an azide. In certain embodiments, $R^1$ is an azide. In certain embodiments, $R^1$ is a azidoalkyl group, wherein the alkyl portion is $C_{1-6}$. In certain embodiments, $R^1$ is an azidomethyl group. In certain embodiments, $R^1$ is an azidoethyl group.

In some embodiments, an $—R^A—R^1$ group is selected from the group consisting of:

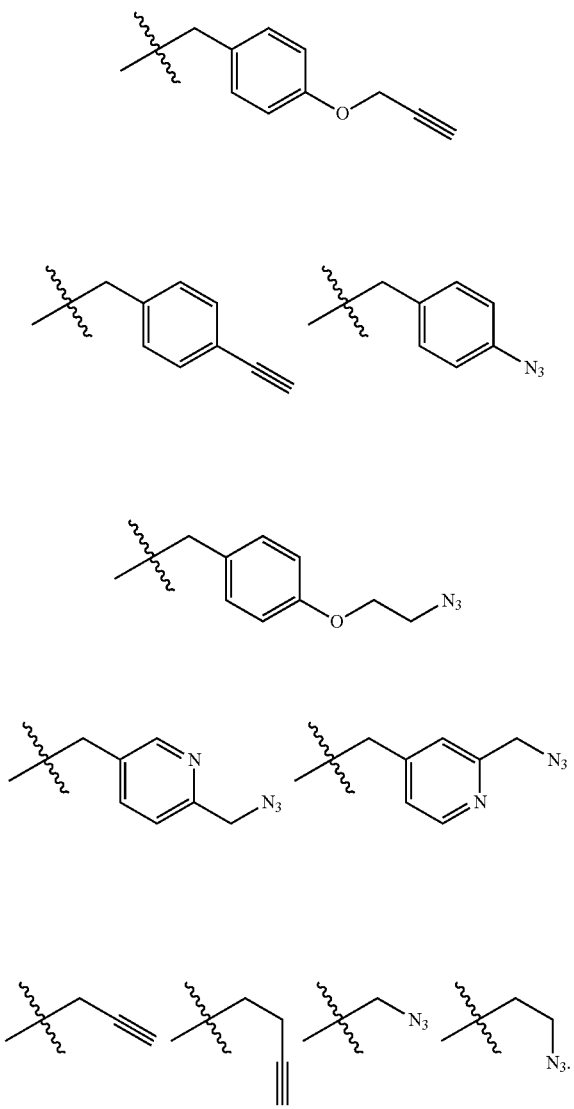

As defined generally above, $R^B$ is a bond or $C_{1-6}$ aliphatic. In some embodiments, $R^B$ is a bond. In some embodiments, $R^B$ is $C_{1-6}$ aliphatic. In some embodiments, $R^B$ is a $C_{1-3}$ alkylene. In certain embodiments, $R^B$ is $C_1$ or $C_2$ alkylene. In certain embodiments, $R^B$ is methylene.

As defined generally herein, $R^{1'}$ is hydrogen or a reactive group capable of undergoing a bioorthogonal reaction. In some embodiments, $R^{1'}$ is hydrogen. In certain embodiments, $R^{1'}$ is a reactive unsaturated group capable of undergoing a [3+2] cycloaddition (sometimes referred to as "click" chemistry). In certain embodiments, $R^{1'}$ comprises an azide capable of undergoing a Staudinger ligation. In certain embodiments, $R^{1'}$ comprises an aldehyde. In certain embodiments, $R^{1'}$ comprises a tetrazine. In certain embodiments, $R^{1'}$ comprises a trans-cyclooctene.

In certain embodiments, $R^{1'}$ is a reactive unsaturated group. As defined generally herein, a reactive unsaturated group is a functional group containing atoms sharing more than one valence bond and that can undergo addition reactions, in particular cycloadditions. In addition to the reactive moiety itself (e.g., double or triple bonded atoms), a reactive unsaturated group optionally comprises an alkyl or heteroalkyl linker moiety of 1-6 atoms. For example, in some embodiments, a reactive unsaturated group is a group selected from propargyloxy, ethynyl, propargyl, homopropargyl, azidoethoxy, azido, azidomethyl, or azidoethyl. In some embodiments, $R^{1'}$ is a reactive unsaturated group that possesses at least one double or triple bond. In some embodiments, $R^{1'}$ is a reactive unsaturated group comprises a dipolarophile. In certain embodiments, $R^{1'}$ is a reactive unsaturated group that comprises a triple bond. In certain embodiments, $R^{1'}$ comprises an alkyne. In certain other embodiments, $R^{1'}$ comprises an alkene. In certain embodiments, $R^{1'}$ comprises an ethynyl group. In certain embodiments, $R^{1'}$ is an ethynyl or propargyl group. In other embodiments, $R^{1'}$ is a reactive unsaturated group that comprises a 1,3-dipole. In certain embodiments, $R^{1'}$ is a reactive unsaturated group that comprises a nitrile oxide, azide, diazomethane, nitrone, or nitrile imine. In certain embodiments, $R^{1'}$ comprises an azide. In certain embodiments, $R^{1'}$ is an azide. In certain embodiments, $R^{1'}$ is a azidoalkyl group, wherein the alkyl portion is $C_{1-6}$. In certain embodiments, $R^{1'}$ is an azidomethyl group. In certain embodiments, $R^{1'}$ is an azidoethyl group. In certain embodiments, $—R^B—R^{1'}$ is propargyl.

In some embodiments, $R^1$ is hydrogen and $R^{1'}$ is a reactive group. In some embodiments, $R^1$ is a reactive group and $R^{1'}$ is hydrogen. In some embodiments, $R^1$ is hydrogen and $R^{1'}$ is a reactive unsaturated group as defined herein. In some embodiments, $R^1$ is a reactive unsaturated group as defined herein and $R^{1'}$ is hydrogen.

In some embodiments, $R^1$ and $R^{1'}$ are each reactive groups. In some embodiments, $R^1$ and $R^{1'}$ are each reactive unsaturated groups. In some embodiments, $R^1$ and $R^{1'}$ are orthogonal to one another. In some embodiments, $R^1$ and $R^{1'}$ are the same. In some embodiments, $R^1$ and $R^{1'}$ are different.

As defined generally above, $R^2$ is hydrogen or $C_{1-6}$ aliphatic. In certain embodiments, $R^2$ is hydrogen. In other embodiments, $R^2$ is $C_{1-6}$ aliphatic. In certain embodiments, $R^2$ is $C_{1-6}$ alkyl. In certain embodiments, $R^2$ is $C_{1-3}$ alkyl. In certain embodiments, $R^2$ is methyl or ethyl.

As defined generally above, $R^3$, $R^4$, and $R^5$ are each independently hydrogen or a protecting group. In certain embodiments, $R^3$, $R^4$, and $R^5$ are each hydrogen. In other embodiments, $R^3$, $R^4$, and $R^5$ are each protecting groups. In certain embodiments, at least one of $R^3$, $R^4$, and $R^5$ is a protecting group. In certain embodiments, at least two of $R^3$, $R^4$, and $R^5$ are protecting groups. In certain embodiments, $R^3$ and $R^4$ are protecting groups, and $R^5$ is hydrogen. In certain embodiments, $R^3$ and $R^4$ are hydrogen, and $R^5$ is a protecting group.

In certain embodiments, a puromycin analog according to the present invention is:
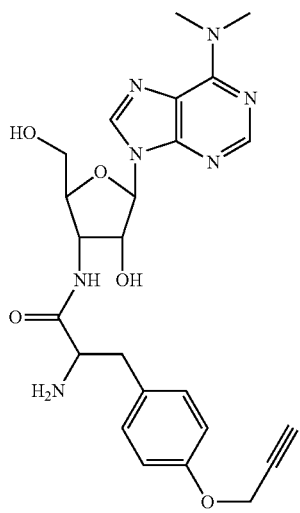
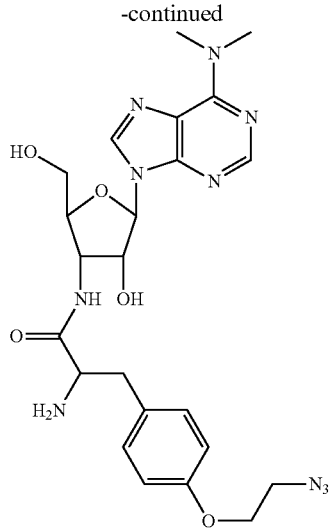
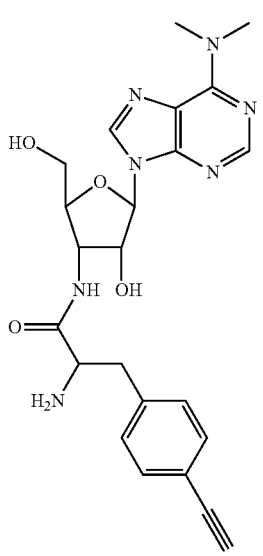
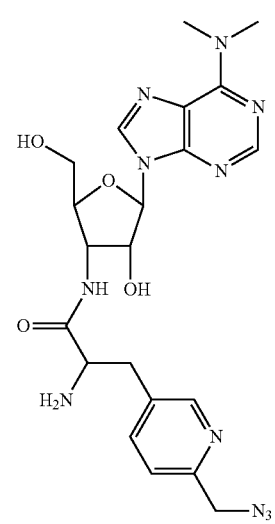
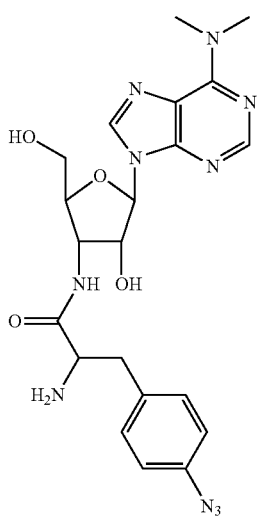
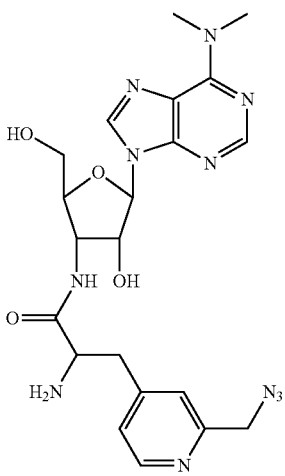

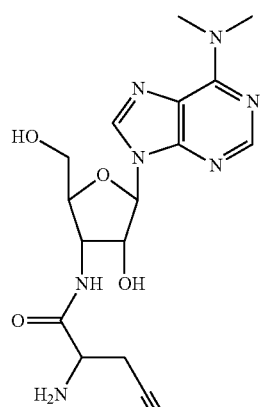
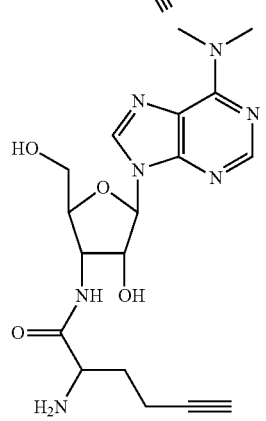
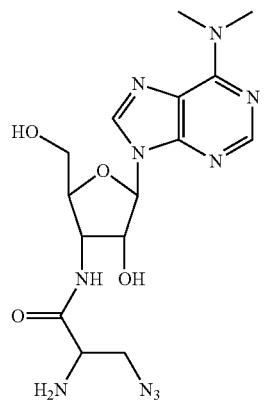
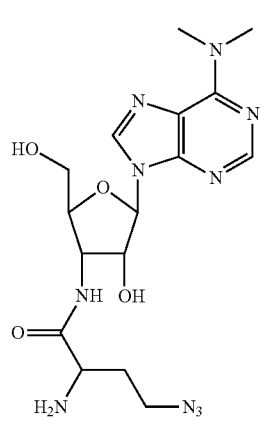
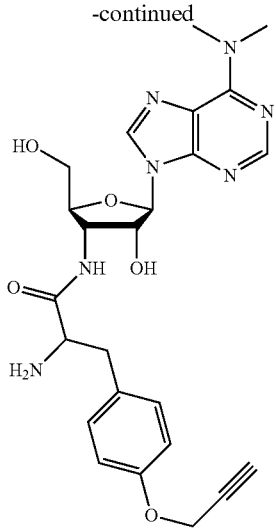
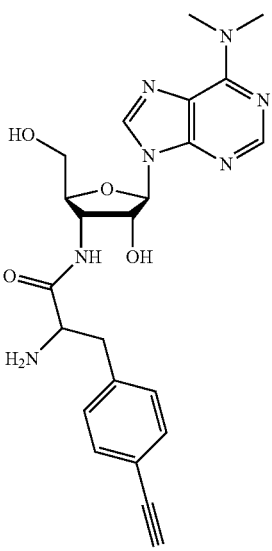
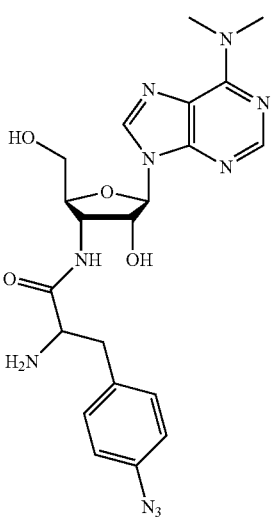

33
-continued
34
-continued
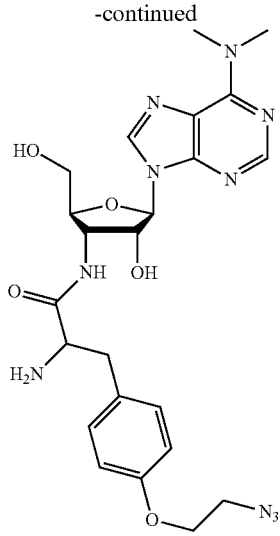
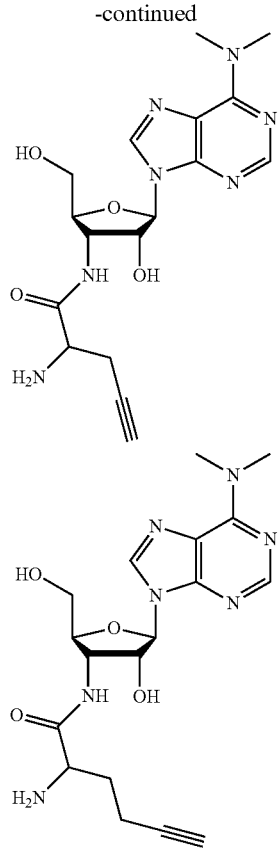

35
-continued
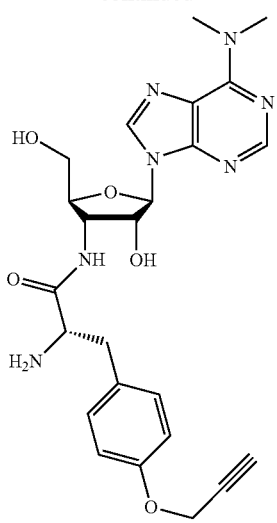
36
-continued
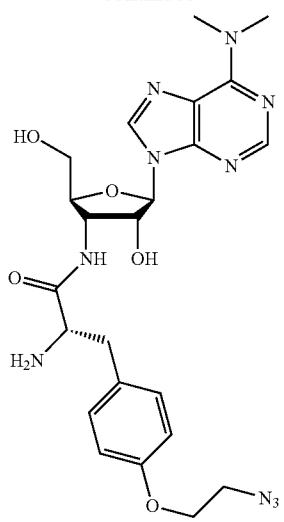
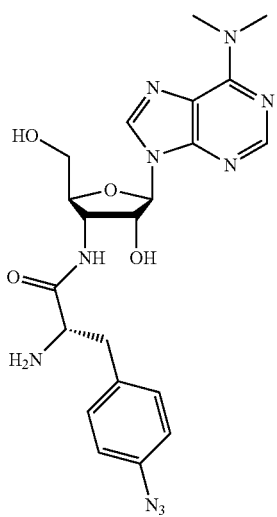
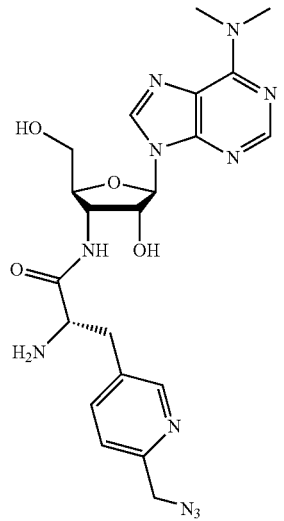
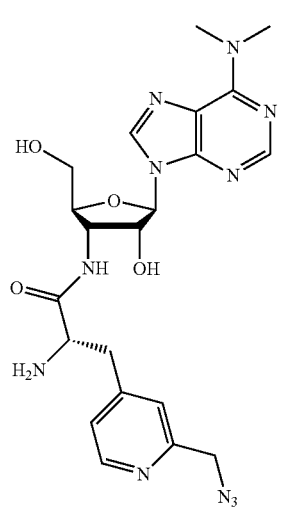

-continued

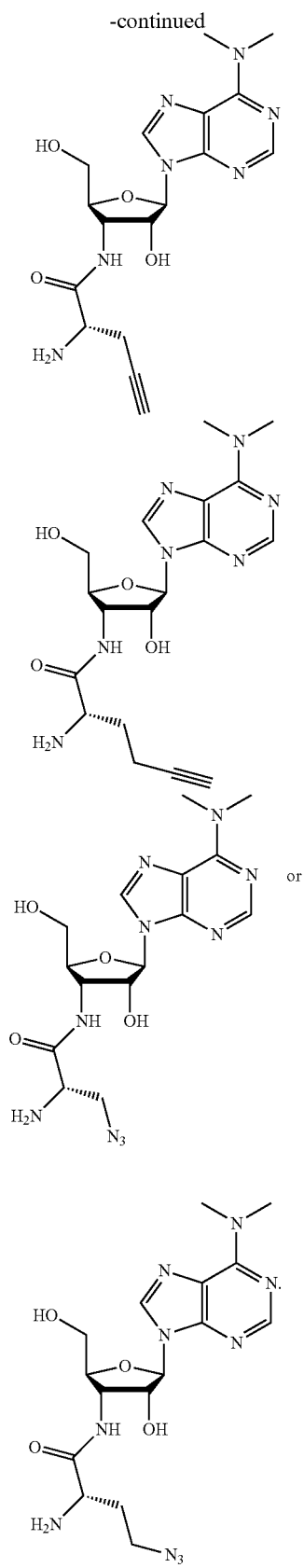

In certain embodiments, a puromycin analog according to the present invention is OP-puro or AE-puro.

Polypeptides and Polypeptide-Puromycin Analog Conjugates

In some embodiments, polypeptides are produced according to methods of the present invention or utilized in methods of the present invention. As will be appreciated by one of ordinary skill in the art, the polypeptides can be of any of a wide range of lengths including short peptides comprising at least 2, 4, 6, 8, 10, 12, 15, 20, 25, 30, or 40 amino acids as well as longer polypeptides and full length proteins.

In some embodiments, puromycin analogs can be incorporated into the proteome of a cell or organism. Isolation or purification of the polypeptides and polypeptide-puromycin analog conjugates of the present invention, where necessary, may be carried out by any of a variety of methods well-known in the art. In some embodiments, purification of polypeptides and polypeptide-puromycin analog conjugates is performed by affinity chromatography or reverse phase HPLC. In certain embodiments, a polypeptide-puromycin analog is purified by affinity chromatography via an affinity label attached to the puromycin analog.

If desired, the sequence of polypeptides or polypeptide-puromycin analog conjugates can be verified using any suitable sequencing method including, but not limited to, Edman degradation, matrix-assisted laser desorption ionization time-of-flight (MALDI-TOF) mass spectrometry, liquid chromatography-mass spectrometry, and the like.

[3+2] Cycloaddition

In certain embodiments, methods provided herein generally include a [3+2] cycloaddition. In such methods, a [3+2] cycloaddition occurs between a first reactive unsaturated group on a polypeptide-puromycin analog conjugate and a second reactive unsaturated group on a reagent comprising a label (also called herein a labeling reagent).

In some embodiments, a labeling reagent is selected such that the second reactive unsaturated group can react via a [3+2] cycloaddition with the first reactive unsaturated group on the puromycin analog. More specifically, in certain embodiments, when the first unsaturated group is a 1,3-dipole, the second unsaturated group will be a dipolarophile that can react with the 1,3-dipole. In other embodiments, when the first unsaturated group is a dipolarophile, the second unsaturated group will be a 1,3-dipole that can react with the dipolarophile.

Optimization of [3+2] cycloaddition reaction conditions is within the skill of the art. In certain embodiments, the [3+2] cycloaddition is performed under aqueous conditions.

In embodiments where the 1,3-dipole is an azide, and the dipolarophile is an alkyne (e.g., ethynyl group), the [3+2] cycloaddition may be performed as described by Sharpless and coworkers (Rostovtsev et al., *Angew Chem. Int. Ed. Engl.* 41:1596-1599 (2002); Lewis et al., *Angew Chem. Int. Ed. Engl.* 41:1053-1057 (2002); Wang et al., *J. Am. Chem. Soc.* 125:3192-3193 (2003)) at physiological temperatures, under aqueous conditions and in the presence of copper(I) (or Cu(I)), which catalyzes the cycloaddition. This catalyzed version of the [3+2] cycloaddition is termed "click" chemistry.

In other embodiments, for example where the presence of exogenous Cu(I) is not desired (e.g., when Cu(I) is toxic to a living system), the [3+2] cycloaddition between the azide and the alkyne may be performed as described by Sharpless and coworkers except for the presence of Cu(I). In certain embodiments, a labeling reagent used in a cycloaddition comprises a copper chelating moiety in addition to a reactive unsaturated group and a label. As used herein, the term "Cu chelating moiety" refers to any entity characterized by the presence of two or more polar groups that can participate in the formation of a complex (containing more than one coordinate bond) with copper(I) ions. A copper chelating moiety can mobilize copper(I) ions naturally present in a living system (e.g., a cell) in the vicinity of the [3+2] cycloaddition. Specific Cu(I) chelators are known in the art and include, but are not limited to, neocuproine (Al-Sa'doni et al., *Br. J. Pharmacol.* 121:1047-1050 (1997); De Man et al., *Eur. J. Pharmacol.* 381:151-159 (1999); Gocmen et al., *Eur. J. Pharmacol.* 406: 293-300 (2000)) and bathocuproine disulphonate (Bagnati et al., *Biochem. Biophys. Res. Commun.* 253:235-240 (1998)). In other embodiments, an alternative copper-free system that does not require a copper-chelating moiety is employed. For example, [3+2] cycloadditions between azides and cyclooctynes and difluorocyclooctynes described by Bertozzi et al. (*J. Am. Chem. Soc.* 126:15046-15047 (2004)) may be employed.

Staudinger Ligation

In certain embodiments, methods provided herein generally include a Staudinger ligation. In certain embodiments, the Staudinger ligation occurs between an azide group on a polypeptide-puromycin analog conjugate and a staining agent comprising an optionally substituted triarylphosphine attached to a label.

Optimization of reaction conditions for the Staudinger is within the skill in the art. In certain embodiments, the Staudinger ligation is performed under aqueous conditions. Examples of reaction conditions have been described, for example, in: Saxon et al., *Science,* 2000, 287: 2007-2010; Saxon et al., *Org. Lett.,* 2000, 2: 2141-2143; Kiick et al., *Proc. Natl. Acad. Sci. USA,* 2002, 99: 19-24; Lemieux et al., *J. Am. Chem. Soc.,* 2003, 125: 4708-4709; Prescher et al., *Nature,* 2004, 430: 873-877.

Other Bioorthogonal Reactions

Other bioorthogonal reactions may also be used in methods provided herein. In certain embodiments, methods provided herein generally include a bioorthogonal reaction selected from the group consisting of [3+2] cycloaddition, Staudinger ligation, inverse electron demand Diels-Alder, oxime ligation, hydrazone ligation, and [2+2+2] cycloaddition. In certain embodiments, an inverse electron demand Diels-Alder reaction is used in a provided method. In certain embodiments, a tetrazine ligation is used in a provided method. In certain embodiments, an oxime ligation is used in a method provided herein. In certain embodiments, a hydrazone ligation is used in a method provided herein. In certain embodiments, a [2+2+2] cycloaddition is used in a method provided herein. In certain embodiments, a quadricyclane ligation is used in a method provided herein.

Labels and Detection of Labeled Polypeptides

In certain embodiments, methods of the present invention include a bioorthogonal reaction between a first reactive group on a puromycin analog conjugated to a polypeptide and a second reactive group attached to a label. The bioorthogonal reaction results in labeling of the polypeptide. In certain embodiments, methods of the present invention include a [3+2] cycloaddition between a first reactive unsaturated group on a puromycin analog conjugated to a polypeptide and a second reactive unsaturated group attached to a label, resulting in labeling of the polypeptide.

As described herein, the role of a label is to allow visualization, detection, and/or identification of a polypeptide, e.g., a nascent polypeptide in a cell, following labeling. In certain embodiments, a label (or detectable agent or moiety) is selected such that it generates a signal which can be measured and whose intensity is related (e.g., proportional) to the amount of labeled polypeptide, e.g., in a sample being analyzed. In certain embodiments, in array-based detection methods described herein, the detectable agent is also selected such that it generates a localized signal, thereby allowing spatial resolution of the signal for each spot on the array.

In certain embodiments, the association between a label and a labeling reagent comprising the second reactive group (e.g., a reactive unsaturated group) is covalent. A label can be directly attached to a reactive group on the labeling reagent or indirectly through a linker.

Methods for attaching detectable moieties to chemical molecules are well-known in the art. In certain embodiments, the label and unsaturated group are directly, covalently linked to each other. In certain embodiments, the direct covalent binding is through an amide, ester, carbon-carbon, disulfide, carbamate, ether, thioether, urea, amine, or carbonate linkage. In certain embodiments, covalent binding is achieved by taking advantage of functional groups present on the reactive group and detectable moiety. Suitable functional groups that can be used to attach the two chemical entities together include, but are not limited to, amines, anhydrides, hydroxy groups, carboxy groups, and thiols. A direct linkage may also be formed using an activating agent, such as a carbodiimide. A wide range of activating agents are known in the art and are suitable for linking a label and an reactive group (e.g., a reactive unsaturated group).

In other embodiments, a reactive group (e.g., a reactive unsaturated group) of a labeling reagent and a label are indirectly covalently linked to each other via a linker group. Such indirect attachment can be accomplished by using any number of stable bifunctional agents well known in the art, including homofunctional and heterofunctional linkers (see, for example, Pierce Catalog and Handbook). Use of a bifunctional linker differs from the use of an activating agent in that the former results in a linking moiety being present in the reaction product, whereas the latter results in a direct coupling between the two moieties involved in the reaction. The role of the bifunctional linker may be to allow the reaction between two otherwise inert moieties. Alternatively or additionally, the bifunctional linker, which becomes part of the reaction product, may be selected such that it confers some degree of conformational flexibility to the reaction product, or other useful or desired properties. In certain embodiments, the linker is cleavable (e.g., chemically cleavable or photochemically cleavable). The presence of a cleavable linker between the label and the puromycin analog allows for temporary labeling of the polypeptide-puromycin analog conjugate. With such a system, whenever desired (e.g., following detection of the polypeptide), the label can be cleaved off the puromycin analog to which it is attached. Cleavable linkers are known in the art. For example, the linker may be a cystamine linker, the disulfide bond of which can be reduced using dithiothreitol (DTT).

Any of a wide variety of labeling/detectable agents can be used in the practice of the present invention. Suitable detectable agents include, but are not limited to, various ligands, radionuclides (such as, for example, $^{32}$P, $^{35}$S, $^{3}$H, $^{14}$C, $^{125}$I, $^{131}$I, and the like); fluorescent dyes (for specific exemplary fluorescent dyes, see below); chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, i.e., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin, haptens, and proteins for which antisera or monoclonal antibodies are available.

In certain embodiments, the label comprises a fluorescent moiety. Numerous known fluorescent labeling moieties of a wide variety of chemical structures and physical characteristics are suitable for use in the practice of the present invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™ cyanine dyes (e.g. Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for coupling fluorescent dyes to other chemical entities see, for example, "The Handbook of Fluorescent Probes and Research Products", 9th Ed., Molecular Probes, Inc., Eugene, Oreg.

Favorable properties of fluorescent labeling agents to be used in the practice of the invention include high molar absorption coefficient, high fluorescence quantum yield, and photostability. In certain embodiments, labeling fluorophores desirably exhibit absorption and emission wavelengths in the visible (i.e., between 400 and 750 nm) rather than in the ultraviolet range of the spectrum (i.e., lower than 400 nm). Other desirable properties of the fluorescent moiety may include cell permeability and low toxicity, for example if labeling of the polypeptide is to be performed in a cell or an organism (e.g., a living animal).

As reported in the Examples, various fluorescent labelling reagents (e.g., staining reagents) have been used by the present Applicants, including Alexa568-azide, which is non-cell permeable, and tetramethylrhodamine (TMR)-azide, which is cell permeable.

Selection of a particular label will depend on the purpose of the labeling to be performed and will be governed by several factors, such as the ease and cost of the labeling method, the quality of sample labeling desired, the effects of the detectable moiety on the cell or organism, the nature of the detection system, the nature and intensity of the signal generated by the detectable moiety, and the like.

As will be recognized by one of ordinary skill in the art, detection of polypeptides labeled according to methods disclosed herein may be performed by any of a wide variety of methods, and using any of a wide variety of techniques. Selection of a suitable detection method and/or detection technique based on the nature of the label (e.g., radionuclide, fluorophore, chemiluminescent agent, quantum dot, enzyme, magnetic label, hapten, etc.) is within the skill in the art.

For example, fluorescently labeled polypeptides may be detected using fluorescence detection techniques, including, but not limited to, flow cytometry and fluorescence microscopy. Selection of a specific fluorescence detection technique will be governed by many factors including the purpose of the labeling experiment (e.g., study of chromosomes ultrastructure, cell proliferation determination, or toxicity assay) as well as the location of the labeled polypeptide to be detected (i.e., such as inside a living cell or inside a tissue).

Flow cytometry is a sensitive and quantitative technique that analyzes particles (such as cells) in a fluid medium based on the particles' optical characteristic (H. M. Shapiro, "Practical Flow Cytometry", 3rd Ed., 1995, Alan R. Liss, Inc.; and "Flow Cytometry and Sorting, Second Edition", Melamed et al. (Eds), 1990, Wiley-Liss: New York). A flow cytometer hydrodynamically focuses a fluid suspension of particles containing one or more fluorophores, into a thin stream so that the particles flow down the stream in a substantially single file and pass through an examination or analysis zone. A focused light beam, such as a laser beam, illuminates the particles as they flow through the examination zone, and optical detectors measure certain characteristics of the light as it interacts with the particles (e.g., light scatter and particle fluorescence at one or more wavelengths).

Alternatively or additionally, fluorescently labeled polypeptides in cells, tissues or organisms may be visualized and detected by fluorescence microscopy using various imaging techniques. In addition to conventional fluorescence microscopy, fluorescently labeled polypeptides can be analyzed by, for example, time-lapse fluorescence microscopy, confocal fluorescence microscopy, or two-photon fluorescence microscopy. Time-lapse microscopy techniques (D. J. Stephens and V. J. Allan, *Science,* 2003, 300:82-86) can provide a complete picture of complex cellular processes that occur in three dimensions over time. Information acquired by these methods allow dynamic phenomena such as cell growth, cell motion and cell nuclei division to be monitored and analyzed quantitatively. Confocal microscopy (L. Harvath, *Methods Mol. Biol.,* 1999, 115:149-158; Z. Foldes-Papp et al., *Int. Immunopharmacol.,* 2003, 3:1715-1729) offers several advantages over conventional optical microscopy, including controllable depth of field, the elimination of image degrading out-of-focus information, and the ability to collect serial optical sections from thick specimens (e.g., tissues or animals). Two-photon fluorescence microscopy (P. T. So et al., *Annu. Rev. Biomed. Eng.,* 2000, 2:399-429), which involves simultaneous absorption of two photons by the fluorophore at the focal point of the microscope, allows three-dimensional imaging in highly localized volumes (e.g., in the nucleus of cells) with minimal photobleaching and photodamage.

Signals from fluorescently labeled polypeptides attached to microarrays or located inside cells in multi-well plates can be detected and quantified by any of a variety of automated and/or high-throughput instrumentation systems including fluorescence multi-well plate readers, fluorescence activated cell sorters (FACS) and automated cell-based imaging systems that provide spatial resolution of the signal. Methods for the simultaneous detection of multiple fluorescent labels and the creation of composite fluorescence images are well-known in the art and include the use of "array reading" or "scanning" systems, such as charge-coupled devices (i.e., CCDs) (see, for example, Hiraoka et al., *Science,* 1987, 238: 36-41; Aikens et al., *Meth. Cell Biol.* 1989, 29:291-313; Divane et al., *Prenat. Diagn.* 1994, 14: 1061-1069; Jalal et al., *Mayo Clin. Proc.* 1998, 73: 132-137; Cheung et al., *Nature Genet.* 1999, 21: 15-19; see also, for example, U.S. Pat. Nos.

5,539,517; 5,790,727; 5,846,708; 5,880,473; 5,922,617; 5,943,129; 6,049,380; 6,054,279; 6,055,325; 6,066,459; 6,140,044; 6,143,495; 6,191,425; 6,252,664; 6,261,776; and 6,294,331). A variety of instrumentation systems have been developed to automate such analyses including the automated fluorescence imaging and automated microscopy systems developed by Cellomics, Inc. (Pittsburgh, Pa.), Amersham Biosciences (Piscataway, N.J.), TTP LabTech Ltd (Royston, UK), Quantitative 3 Dimensional Microscopy (Q3DM) (San Diego, Calif.), Evotec AG (Hamburg, Germany), Molecular Devices Corp. (Sunnyvale, Calif.), and Carl Zeiss AG (Oberkochen, Germany).

Signal-to-Noise Ratio Improvements

In another aspect, the present invention provides a system for improving the signal-to-noise ratio in the detection of a polypeptide labeled with a fluorescent moiety using a labeling process disclosed herein.

Any molecule of labeling reagent that has not been consumed by a bioorthogonal labeling reaction may contribute to the background (i.e., non-specific) signal. The present invention provides a strategy for reducing or eliminating this background signal which comprises quenching the fluorescent signal of the label on the unreacted labeling reagent by reaction with a molecule comprising a quencher moiety. For example, in some embodiments, the reaction between the reagent and the molecule comprising the quencher moiety is a [3+2] cycloaddition.

Thus, certain inventive methods for improving the signal-to-noise ratio in detection of a fluorescently labeled polypeptide prepared as described herein, comprise contacting unreacted reagent comprising a second reactive unsaturated group and a fluorescent label with a quenching molecule comprising a reactive unsaturated group attached to a quenching moiety such that a [3+2] cycloaddition takes place between the reactive unsaturated groups of the labelling reagent and quenching molecule. After reaction, the physical proximity between the fluorescent label and the quenching moiety prevents detection of a fluorescent signal from the fluorescent label.

Examples of quenching moieties include, but are not limited to, DABCYL (i.e., 4-(4'-dimethylaminophenylazo)-benzoic acid) succinimidyl ester, diarylrhodamine carboxylic acid, succinimidyl ester (or QSY-7), and 4',5'-dinitrofluorescein carboxylic acid, succinimidyl ester (or QSY-33) (all available, for example, from Molecular Probes), quencher 1 (Q1; available from Epoch Biosciences, Bothell, Wash.), or "Black hole quenchers" BHQ-1, BHQ-2, and BHQ-3 (available from BioSearch Technologies, Inc., Novato, Calif.).

Labeling of Polypeptides in Cells

The present invention also provides methods for labeling polypeptides in cells. In some embodiments, such methods comprise: contacting a cell with an effective amount of a puromycin analog comprising a first reactive group, such that the puromycin analog is covalently bound to the C-terminus of one or more nascent polypeptides in the cell to form one or more polypeptide-puromycin analog conjugates; and contacting the cell with a compound comprising a second reactive group and a label, such that a bioorthogonal reaction occurs between the first and second reactive groups. In certain embodiments, such methods comprise: contacting a cell with an effective amount of a puromycin analog comprising a first reactive unsaturated group, such that the puromycin analog is covalently bound to the C-terminus of one or more nascent polypeptides in the cell to form one or more polypeptide-puromycin analog conjugates; and contacting the cell with a compound comprising a second reactive unsaturated group and a label, such that a [3+2] cycloaddition occurs between the first and second reactive unsaturated groups.

Unless otherwise stated, the labeling reagent and reaction conditions used in these methods are analogous to those described above for the methods of labeling polypeptides. As discussed herein, the labeling methods of the present invention exhibit several advantages over currently available labeling protocols including the possibility of staining polypeptides in living cells. The terms "living cell" and "live cell" are used herein interchangeably and refer to a cell which is considered living according to standard criteria for that particular type of cell, such as maintenance of normal membrane potential, energy metabolism, or proliferative capability. In particular, the methods of the present invention do not require fixation and/or denaturation of the cells.

In some embodiments, the invention relates to incorporation of labels into polypeptides in cells in culture. In certain embodiments, the cells are grown in standard tissue culture plastic ware. Such cells include normal and transformed cells derived. In certain embodiments, cells are of mammalian (human or animal, such as rodent or simian) origin. Mammalian cells may be of any fluid, organ or tissue origin (e.g., blood, brain, liver, lung, heart, bone, and the like) and of any cell types (e.g., basal cells, epithelial cells, platelets, lymphocytes, T-cells, B-cells, natural killer cells, macrophages, tumor cells, and the like).

Cells suitable for use in the methods of the present invention may be primary cells, secondary cells or immortalized cells (i.e., established cell lines). They may have been prepared by techniques well-known in the art (for example, cells may be obtained by drawing blood from a patient or a healthy donor) or purchased from immunological and microbiological commercial resources (for example, from the American Type Culture Collection, Manassas, Va.). Alternatively or additionally, cells may be genetically engineered to contain, for example, a gene of interest such as a gene expressing a growth factor or a receptor.

Cells to be used in the methods of the present invention may be cultured according to standard culture techniques. For example, cells are often grown in a suitable vessel in a sterile environment at 37° C. in an incubator containing a humidified 95% air-5% $CO_2$ atmosphere. Vessels may contain stirred or stationary cultures. Various cell culture media may be used including media containing undefined biological fluids such as fetal calf serum. Cell culture techniques are well known in the art, and established protocols are available for the culture of diverse cell types (see, for example, R. I. Freshney, *Culture of Animal Cells: A Manual of Basic Technique,* 2nd Edition, 1987, Alan R. Liss, Inc.).

Incorporation of Puromycin Analog into Nascent Polypeptides to Form Conjugates

Puromycin-polypeptide conjugates are well known in the art. Puromycin is an antibiotic that competes with aminoacyl-tRNAs for the A-site of ribosomes. After binding to the ribosome, puromycin then becomes covalently attached to the C-terminus of the nascent polypeptide chain, resulting in termination. The puromycin mechanism of action is used to provide a snapshot of nascent polypeptides synthesized in vivo. Traditional methods include using a polyclonal antibody to puromycin to isolate the conjugates (Hansen et al., *J. Biol. Chem.* 269:26610-26613 (1994)) or employing bioorthogonal methionine (Met) analogs such as an azido analog azidohomoalanine (Aha) and an alkyne analog homopropargylglycine (Hpg) (Dietrich et al., *Proc. Natl. Acad. Sci. USA* 103:9482-9487 (2006); Beatty et al., *Angew. Chem. Intl. Ed. Engl.* 45:7364-7367 (2006)). However, there are disadvantages to the traditional approaches. Antibod-based technologies can exhibit a lot of variability and non-specific background noise. Antibodies are less uniform and more difficult to standardize than a chemical compound. Antibodies have high molecular weights and do not penetrate effectively and efficiently through a thick tissue or organ sample. In contrast, fluorescent molecules such as those employed in the present invention are much smaller than antibodies, in some embodiments about 300-500 times smaller, and in some embodiments they can diffuse into and stain thick specimens. In some embodiments, the methods described herein allow whole-mount fluorescent imaging of large fragments of tissue and organs, which would have to be physically sectioned to be imaged by traditional immunofluorescence. Metabolic labeling with Met analogs requires Met-free media, which prevents the use of this method in animals, unlike the methods of the present invention which can be used in vivo. Met analog incorporation is proportional to the number of Met residues in a protein, while the puromycin analogs of the present invention incorporate at exactly one molecule per nascent polypeptide chain. Met analogs will not label proteins that do not start with or contain a Met residue, while the methods of the present invention do not depend on amino acid content. Met analogs need to be first activated and converted to amino acyl-tRNAs before incorporation into proteins; by contrast, puromycin analogs of the present invention generate covalent conjugates with nascent polypeptide chains directly, without any prior modification.

Contacting cells in vitro with an effective amount of a puromycin analog such that the puromycin analog is conjugated to a nascent polypeptide in the cell may be carried out using any suitable protocol. A step of contacting a cell with an effective amount of a puromycin analog may be performed, for example, by incubating the cell with the puromycin analog under suitable incubation conditions (e.g., in culture medium at 37° C.). In certain embodiments, it may be desirable to avoid disturbing the cells in any way (e.g., by centrifugation steps or temperature changes) that may perturb their protein synthesis patterns. The incubation time will be dependent on the cell population's rate of cell cycling entry and progression. Optimization of incubation time and conditions is within the skill in the art.

Following conjugation of a puromycin analog to a nascent polypeptides of in vitro cells, the step of contacting the cells with a labeling reagent comprising the second reactive group and a label may be performed by any suitable method. In some embodiments, cells are incubated in the presence of a labeling reagent in a suitable incubation medium (e.g., culture medium) at 37° C. and for a time sufficient for the reagent to penetrate into the cell and react with any polypeptide-puromycin analog conjugate. Optimization of the concentration of labeling reagent, reaction time and conditions is within the skill in the art.

As described herein, in embodiments where the presence of exogenous Cu(I) is not desirable, a [3+2] cycloaddition may be carried out using various copper-free reaction conditions.

In embodiments where the labelling reagent does not exhibit high cell permeability, permeabilization may be performed to facilitate access of the labelling reagent to cellular cytoplasm, or intracellular components or structures of the cells. In certain embodiments, permeabilization may allow a reagent to enter into a cell and reach a concentration within the cell that is greater than that which would normally penetrate into the cell in the absence of such permeabilization treatment.

Permeabilization of the cells may be performed by any suitable method (see, for example, C. A. Goncalves et al., *Neurochem. Res.* 2000, 25: 885-894). Such methods include, but are not limited to, exposure to a detergent (such as CHAPS, cholic acid, deoxycholic acid, digitonin, n-dodecyl-β-D-maltoside, lauryl sulfate, glycodeoxycholic acid, n-lauroylsarcosine, saponin, and triton X-100) or to an organic alcohol (such as methanol and ethanol). Other permeabilization methods comprise the use of certain peptides or toxins that render membranes permeable (see, for example, O. Aguilera et al., *FEBS Lett.* 1999, 462: 273-277; A. Bussing et al., *Cytometry,* 1999, 37: 133-139). Selection of an appropriate permeabilizing agent and optimization of the incubation conditions and time can easily be performed by one of ordinary skill in the art.

Labeling of Polypeptides in Tissues or Organisms

The present invention also provides methods for labeling polypeptides in organisms (i.e., living biological systems). In certain embodiments, such methods comprise the steps of administering to an organism an effective amount of a puromycin analog comprising a first reactive group, such that the puromycin analog is covalently bound to the C-terminus of one or more nascent polypeptides in the organism to form one or more polypeptide-puromycin analog conjugates; contacting at least one cell of the organism with a compound comprising a second reactive group and a label, such that a bioorthogonal reaction occurs between the first and second reactive groups. In certain embodiments, a provided method comprises the steps of administering to an organism an effective amount of a puromycin analog comprising a first reactive unsaturated group, such that the puromycin analog is covalently bound to the C-terminus of one or more nascent polypeptides in the organism to form one or more polypeptide-puromycin analog conjugates; contacting at least one cell of the organism with a compound comprising a second reactive unsaturated group and a label, such that a [3+2] cycloaddition occurs between the first and second reactive unsaturated groups.

Unless otherwise stated, labelling reagents and reaction conditions used in these methods are analogous to those described herein for the methods of labeling polypeptides in cells and can be determined/optimized by one skilled in the art.

Methods of labeling of the present invention may be performed using any living system that has or can develop the ability to act or function independently. Thus, labeling methods of the present invention may be performed in unicellular or multicellular systems, including, humans, animals, plants, bacteria, protozoa, and fungi. In certain embodiments, labeling methods of the present invention are performed in a human or another mammal (e.g., mouse, rat, rabbit, dog, cat, cattle, swine, sheep, horse or primate). In certain embodiments, labeling methods of the present invention are performed in a non-human whole animal.

Administration of a puromycin analog to an organism may be performed using any suitable method that results in conjugation of the puromycin analog to nascent polypeptides of the organism.

For example, a puromycin analog may be formulated in accordance with conventional methods in the art. Proper formulation is dependent upon the route of administration chosen. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections. Alternatively, a puromycin analog preparation can be administered in a local rather than systemic manner, for example, via injection directly into a specific tissue, often in a depot or sustained release formulation.

Following conjugation of a puromycin analog to nascent polypeptides in cells of the organism, a step of contacting at least one cell of the organism with a reagent comprising the second reactive group attached to a label may be performed by any suitable method that allows for a bioorthogonal reaction to take place.

In certain embodiments, cells are collected (e.g., by drawing blood from the organism), isolated from a tissue obtained by biopsy (e.g., needle biopsy, laser capture micro dissection or incisional biopsy) or isolated from an organ or part of an organ (e.g., harvested at autopsy). The cells can then be submitted to the bioorthogonal labeling as described above.

In other embodiments, a tissue obtained by biopsy or an organ or part of an organ harvested at autopsy may be prepared for labelling as known in the art (e.g., fixed, embedded in paraffin and sectioned) and incubated in the presence of the bioorthogonal reagent (e.g., after de-waxing).

Example 4 describes an experiment where a mouse was intraperitoneally injected with OP-puro and its organs harvested 1 hour after injection, prepared for staining and stained with tetramethylrhodamine(TMR)-azide and with Hoechst. Fluorescence images of the small intestine, spleen, kidney, and liver are presented in FIGS. 3 and 4.

Isolated Labeled Polypeptides

In another aspect, the present invention provides isolated detectable polypeptides, for example, prepared by one of the methods described herein. More specifically, in certain embodiments, the present invention provides polypeptides that are detectable following a bioorthogonal reaction as well as isolated polypeptides that contain at least one detectable moiety that has been incorporated via a bioorthogonal reaction. In certain embodiments, the present invention provides polypeptides that are detectable following a [3+2] cycloaddition reaction as well as isolated polypeptides that contain at least one detectable moiety that has been incorporated via a [3+2] cycloaddition.

In certain embodiments, an inventive polypeptide contains at least one puromycin analog comprising a reactive group. In certain embodiments, the reactive group undergoes a bioorthogonal reaction in the presence of a reagent comprising a different reactive group attached to a label. In certain embodiments, an inventive polypeptide contains at least one puromycin analog comprising a reactive unsaturated group. In certain embodiments, the reactive unsaturated group undergoes a [3+2] cycloaddition in the presence of a reagent comprising a different reactive unsaturated group attached to a label.

In other embodiments, an inventive polypeptide contains at least one puromycin analog attached to a label. For example, the puromycin analog may comprise a cycloadduct resulting from a [3+2] cycloaddition.

Detectable polypeptides of the present invention may be prepared by any suitable method, as described herein, including synthetic methods, enzymatic methods, and by using ribosomal machinery.

As can be appreciated by one of ordinary skill in the art, isolated detectable polypeptides of the present invention may be used in a wide variety of applications. For example, isolated detectable polypeptides may be used in assays. In certain embodiments, detectable polypeptides may be provided with appropriate labelling reagents. In other embodiments, detectable polypeptides are provided attached to an array or micro-array.

Arrays according to the present invention comprise a plurality of detectable polypeptides immobilized to discrete spots on a substrate surface. Substrate surfaces can be made of any of rigid, semi-rigid or flexible materials that allow for direct or indirect attachment (i.e., immobilization) of detectable polypeptides to the substrate surface. Suitable materials include, but are not limited to, cellulose, cellulose acetate, nitrocellulose, glass, quartz other crystalline substrates such as silicones, and various plastics and plastic copolymers. When fluorescence is to be detected, arrays comprising cyclo-olefin polymers may be used in some embodiments.

The presence of reactive functional chemical groups on the materials can be exploited to directly or indirectly attach the detectable polypeptides to the substrate surface. Methods for immobilizing polypeptides to substrate surfaces to form an array are well-known in the art.

Cells Comprising Labeled Polypeptides

In another aspect, the present invention provides cells comprising detectable polypeptides, for example prepared by one or more of the methods described herein. More specifically, in certain embodiments, the present invention provides cells comprising polypeptides that are detectable following a bioorthogonal reaction as well as cells comprising polypeptides that contain at least one detectable moiety that has been incorporated via a bioorthogonal reaction. In certain embodiments, the present invention provides cells comprising polypeptides that are detectable following a [3+2] cycloaddition reaction as well as cells comprising polypeptides that contain at least one detectable moiety that has been incorporated via a [3+2] cycloaddition.

As will be recognized by one of ordinary skill in the art, a cell of the present invention may comprise any of the detectable polypeptides described herein.

Determination of Protein Synthesis

In another aspect, the present invention provides methods for measuring protein synthesis and/or protein synthesis rates in a cell or an organism. Such methods may comprise steps of: contacting a cell with an effective amount of a puromycin analog comprising a first reactive group, such that the puromycin analog is covalently bound to the C-terminus of one or more nascent polypeptides in the cell to form one or more polypeptide-puromycin analog conjugates; contacting the cell with a compound comprising a second reactive group and a label, such that a bioorthogonal reaction occurs between the first and second reactive groups; and determining the amount of labeled protein in the cell to measure protein synthesis. In certain embodiments, a provided method comprises steps of: contacting a cell with an effective amount of a puromycin analog comprising a first reactive unsaturated group, such that the puromycin analog is covalently bound to the C-terminus of one or more nascent polypeptides in the cell to form one or more polypeptide-puromycin analog conjugates; contacting the cell with a compound comprising a second reactive unsaturated group and a label, such that a [3+2] cycloaddition occurs between the first and second reactive unsaturated groups; and determining the amount of labeled protein in the cell to measure protein synthesis. In certain embodiments, the amount of label gives information about the extent of protein synthesis. In other embodiments, the amount of label gives information about the rate of protein synthesis.

In other embodiments, such methods comprise steps of: administering to an organism an effective amount of a puromycin analog comprising a first reactive group, such that the puromycin analog is covalently bound to the C-terminus of one or more nascent polypeptides in the organism to form one or more polypeptide-puromycin analog conjugates; contacting at least one cell of the organism with a compound comprising a second reactive group and a label, such that a bioorthogonal reaction occurs between the first and second reactive groups; and determining the amount of label in the at least one cell in order to measure protein synthesis in the organism. In certain embodiments, a provided method comprises steps of: administering to an organism an effective amount of a puromycin analog comprising a first reactive unsaturated group, such that the puromycin analog is covalently bound to the C-terminus of one or more nascent polypeptides in the organism to form one or more polypeptide-puromycin analog conjugates; contacting at least one cell of the organism with a compound comprising a second reactive unsaturated group and a label, such that a [3+2] cycloaddition occurs between the first and second reactive unsaturated groups; and determining the amount of label in the at least one cell in order to measure protein synthesis in the organism.

In certain embodiments, the amount of label gives information about the extent of protein synthesis in the organism. In other embodiments, the amount of label gives information about the rate of protein synthesis in the organism.

These methods may be performed using techniques and procedures as described herein for methods of labeling polypeptides in cells and organisms. With such methods, the manner of performing the contacting and/or administering steps, type of labelling reagent, type of label, and techniques for the detection of such labels are analogous to those described for other methods of the present invention relating to labeling polypeptides in cells or in organisms.

Methods for measuring protein synthesis or protein synthesis rates according to the present invention may be used in a wide variety of applications, including, but not limited to characterization of cell lines, optimization of cell culture conditions, characterization of protein synthesis in normal, diseased and injured tissues, and diagnosis of a variety of diseases and disorders in which protein synthesis is involved. In certain embodiments, methods of the present invention allow for the identification of proteins regulated at the level of translation, such as targets of specific miRNAs, targets of other RNA-binding proteins that control translation of specific mRNAs, and targets of signaling pathways that regulate translation, such as TOR signaling.

Diseases and disorders characterized by altered rates of protein synthesis can be monitored by methods of the present invention.

Screening Assays

In another aspect, the present invention provides methods for the identification of agents that perturb protein synthesis. These methods may be used for screening agents for their ability to induce (i.e., increase, enhance or otherwise exacerbate) or inhibit (i.e., decrease, slow down or otherwise suppress) protein synthesis.

For example, such methods may comprise steps of: contacting a cell with a test agent; contacting the cell with an effective amount of a puromycin analog comprising a first reactive group, such that the puromycin analog is covalently bound to the C-terminus of nascent polypeptides in the cell; contacting the cell with a compound comprising a second reactive group and a label, such that a bioorthogonal reaction occurs between the first and second reactive groups; determining the amount of label incorporated into the nascent polypeptides, wherein the amount of label indicates the extent of protein synthesis; and identifying the test agent as an agent that perturbs cellular proliferation if the amount of label incorporated into nascent polypeptides is less than or greater than the amount of label measured in a control in which a cell is not contacted with the test agent. In certain embodiments, a provided method comprises steps of: contacting a cell with a test agent; contacting the cell with an effective amount of a puromycin analog comprising a first reactive unsaturated group, such that the puromycin analog is covalently bound to the C-terminus of nascent polypeptides in the cell; contacting the cell with a compound comprising a second reactive unsaturated group and a label, such that a [3+2] cycloaddition occurs between the first and second reactive unsaturated groups; determining the amount of label incorporated into the nascent polypeptides, wherein the amount of label indicates the extent of protein synthesis; and identifying the test agent as an agent that perturbs cellular proliferation if the amount of label incorporated into nascent polypeptides is less than or greater than the amount of label measured in a control in which a cell is not contacted with the test agent.

In certain embodiments, the determining step is limited to the portion of the proteome being synthesized upon contacting with a test agent.

The manner of performing the steps of contacting the cell; the labelling reagent; the label type; and methods of detecting the labeled polypeptides are analogous to those described for other methods of the present invention relating to measuring protein synthesis and protein synthesis rates in cells in vitro.

As will be appreciated by one of ordinary skill in the art, screening methods of the present invention may also be used to identify compounds or agents that regulate protein synthesis.

In certain embodiments, screening assays of the present invention may be performed using any normal or transformed cells that can be grown in standard tissue culture plastic ware. Cells may be primary cells, secondary cells, or immortalized cells. In certain embodiments, cells to be used in inventive screening methods are of mammalian (human or animal) origin. Cells may be from any organ or tissue origin and of any cell types, as described above.

Selection of a particular cell type and/or cell line to perform a screening assay according to the present invention will be governed by several factors such as the nature of the agent to be tested and the intended purpose of the assay. For example, a toxicity assay developed for primary drug screening may be performed using established cell lines, which are commercially available and usually relatively easy to grow, while a toxicity assay to be used later in the drug development process may preferably be performed using primary or secondary cells, which are often more difficult to obtain, maintain, and/or grow than immortalized cells but which represent better experimental models for in vivo situations.

In certain embodiments, screening methods are performed using cells contained in a plurality of wells of a multi-well assay plate. Such assay plates are commercially available, for example, from Strategene Corp. (La Jolla, Calif.) and Corning Inc. (Acton, Mass.), and include, for example, 48-well, 96-well, 384-well and 1536-well plates.

As will be appreciated by those of ordinary skill in the art, any kind of compounds or agents can be tested using inventive methods. A test compound may be a synthetic or natural compound; it may be a single molecule, a mixture of different molecules or a complex of different molecules. In certain embodiments, inventive methods are used for testing one or more compounds. In other embodiments, inventive methods are used for screening collections or libraries of compounds.

Compounds that can be tested for their capacity or ability to perturb (i.e., induce or inhibit) or regulate protein synthesis may belong to any of a variety of classes of molecules including, but not limited to, small molecules, peptides, saccharides, steroids, antibodies (including fragments or variants thereof), fusion proteins, antisense polynucleotides, ribozymes, small interfering RNAs, peptidomimetics, and the like.

Compounds or agents to be tested according to methods of the present invention may be known or suspected to perturb or regulate protein synthesis. Alternatively, assays may be performed using compounds or agents whose effects on protein synthesis are unknown.

Examples of compounds that may affect protein synthesis and that can be tested by the methods of the present invention include, but are not limited to, carcinogens; toxic agents; chemical compounds such as solvents; mutagenic agents; pharmaceuticals; particulates, gases and noxious compounds in smoke (including smoke from cigarette, cigar and industrial processes); food additives; biochemical materials; hormones; pesticides; ground-water toxins; and environmental pollutants. Examples of agents that may affect protein synthesis and that can be tested by the methods of the present invention include, but are not limited to, microwave radiation, electromagnetic radiation, radioactive radiation, ionizing radiation, heat, and other hazardous conditions produced by or present in industrial or occupational environments.

According to screening methods of the present invention, determination of the ability of a test agent to perturb or regulate protein synthesis includes comparison of the amount of label incorporated into polypeptides of a cell that has been contacted with the test agent with the amount of label incorporated into polypeptides of a cell that has not been contacted with the test agent.

A test agent is identified as an agent that perturbs protein synthesis if the amount of label incorporated into polypeptides of the cell that has been contacted with the test agent is less than or greater than the amount of label measured in the control cell. More specifically, if the amount of label incorporated into polypeptides of the cell that has been contacted with the test agent is less than the amount of label measured in the control cell, the test agent is identified as an agent that inhibits protein synthesis. If the amount of label incorporated into polypeptides of the cell that has been contacted with the test agent is greater than the amount of label measured in the control cell, the test agent is identified as an agent that induces protein synthesis.

Reproducibility of the results may be tested by performing the analysis more than once with the same concentration of the test agent (for example, by incubating cells in more than one well of an assay plate). Additionally, since a test agent may be effective at varying concentrations depending on the nature of the agent and the nature of it mechanism(s) of action, varying concentrations of the test agent may be tested (for example, added to different wells containing cells). Generally, test agent concentrations from 1 fM to about 10 mM are used for screening. In certain embodiments, screening concentrations are between about 10 pM and about 100 μM.

In certain embodiments, the methods described herein further involve the use of one or more negative or positive control compounds. A positive control compound may be any molecule or agent that is known to perturb (i.e., induce or inhibit) or regulate protein synthesis. A negative control compound may be any molecule or agent that is known to have no detectable effects on protein synthesis. In certain embodiments, inventive methods further comprise comparing the effects of the test agent to the effects (or absence thereof) of the positive or negative control compound.

As will be appreciated by those skilled in the art, it is generally desirable to further characterize an agent identified by the inventive screening methods as an agent that perturbs or an agent that regulates protein synthesis. For example, if a test compound has been identified as an agent that perturbs (or regulates) protein synthesis using a given cell culture system (e.g., an established cell line), it may be desirable to test this ability in a different cell culture system (e.g., primary or secondary cells).

Test agents identified by screening methods of the present invention may also be further tested in assays that allow for the determination of the agents' properties in vivo. Accordingly, the present invention provides methods for identifying an agent that perturbs protein synthesis or protein synthesis rate in vivo. Such methods comprise steps of: exposing an organism to a test agent; administering to the organism an effective amount of a puromycin analog comprising a first reactive group, such that the puromycin analog is covalently bound to the C-terminus of nascent polypeptides in the organism; contacting at least one cell of the organism with a compound comprising a second reactive group and a label, such that a bioorthogonal reaction occurs between the first and second reactive groups; determining the amount of label incorporated into the nascent polypeptides in the at least one cell, wherein the amount of label indicates the extent of protein synthesis; and identifying the test agent as an agent that perturbs cellular proliferation if the amount of label incorporated into nascent polypeptides is less than or greater than the amount of label measured in a control in which an organism is not administered a test agent. In certain embodiments, a provided method comprises steps of: exposing an organism to a test agent; administering to the organism an effective amount of a puromycin analog comprising a first reactive unsaturated group, such that the puromycin analog is covalently bound to the C-terminus of nascent polypeptides in the organism; contacting at least one cell of the organism with a compound comprising a second reactive unsaturated group and a label, such that a [3+2] cycloaddition occurs between the first and second reactive unsaturated groups; determining the amount of label incorporated into the nascent polypeptides in the at least one cell, wherein the amount of label indicates the extent of protein synthesis; and identifying the test agent as an agent that perturbs cellular proliferation if the amount of label incorporated into nascent polypeptides is less than or greater than the amount of label measured in a control in which an organism is not administered a test agent.

As will be appreciated by one of ordinary skill in the art, these methods can be used to identify agents that regulate protein synthesis in vivo.

The manner of administration, labelling reagent, type of label and method of detection of the labeled polypeptides are analogous to those described herein for other inventive methods relating to measuring protein synthesis in living systems.

Identification of Nascent Polypeptides

In another aspect, the present invention provides methods of isolating and/or identifying nascent polypeptides.

For example, in certain embodiments, the present invention provides a method of isolating a nascent polypeptide comprising contacting a cell with an effective amount of a puromycin analog comprising a first reactive group, such that the puromycin analog is covalently bound to the C-terminus of a nascent polypeptide in the cell to form a polypeptide-puromycin analog conjugate; contacting the cell with a compound comprising a second reactive group and an affinity label, such that a bioorthogonal reaction occurs between the first and second reactive groups to form an affinity-labeled polypeptide; and affinity purifying the affinity-labeled polypeptide. In certain embodiments, the present invention provides a method of isolating a nascent polypeptide comprising contacting a cell with an effective amount of a puromycin analog comprising a first reactive unsaturated group, such that the puromycin analog is covalently bound to the C-terminus of a nascent polypeptide in the cell to form a polypeptide-puromycin analog conjugate; contacting the cell with a compound comprising a second reactive unsaturated group and an affinity label, such that a [3+2] cycloaddition occurs between the first and second reactive unsaturated groups to form an affinity-labeled polypeptide; and affinity purifying the affinity-labeled polypeptide.

In certain embodiments, an affinity label comprises a hapten. In certain embodiments, the hapten is biotin.

In certain embodiments, the labeled polypeptide is identified by methods known in the art (e.g., mass spectrometry). Such methods are useful in identifying proteins that are synthesized under certain conditions in the cell. In some embodiments, the cell is in a whole animal.

In other embodiments, the present invention provides a method of identifying a nascent polypeptide comprising contacting a cell with an effective amount of a puromycin analog comprising a first reactive group, such that the puromycin analog is covalently bound to the C-terminus of one or more nascent polypeptides in the cell to form one or more polypeptide-puromycin analog conjugates; contacting the cell with a solid support comprising a second reactive group, such that a bioorthogonal reaction occurs between the first and second reactive groups; and identifying the nascent polypeptide. In certain embodiments, the present invention provides a method of identifying a nascent polypeptide comprising contacting a cell with an effective amount of a puromycin analog comprising a first reactive unsaturated group, such that the puromycin analog is covalently bound to the C-terminus of one or more nascent polypeptides in the cell to form one or more polypeptide-puromycin analog conjugates; contacting the cell with a solid support comprising a second reactive unsaturated group, such that a [3+2] cycloaddition occurs between the first and second reactive unsaturated groups; and identifying the nascent polypeptide. In certain embodiments, a method of identifying further comprises cleaving a polypeptide from a surface.

In certain embodiments, the step of identifying is performed using methods known in the art (e.g., mass spectrometry). In other embodiments, the step of contacting a cell is performed by administering a puromycin analog to a whole animal, and at least one cell is then isolated from the animal in order to perform subsequent steps.

Kits

In another aspect, the present invention provides kits comprising materials useful for carrying out one or more of the methods described herein. The inventive kits may be used by diagnostic laboratories, clinical laboratories, experimental laboratories, or practitioners. The invention provides kits which can be used in these different settings.

Basic materials and reagents for labeling polypeptides according to the present invention may be assembled together in a kit. An inventive kit for labeling a polypeptide may include a puromycin analog as described herein and a label. In certain embodiments, an inventive kit for labeling a polypeptide includes a puromycin analog comprising a first reactive group and a compound comprising a second reactive group and a label. In certain embodiments, an inventive kit for labeling a polypeptide may include a puromycin analog comprising a first reactive unsaturated group; and a compound comprising a second reactive unsaturated group and a label. In certain embodiments, a kit comprises reagents which render the procedure specific. Thus, if the detectable agent is a hapten, in certain embodiments the kit comprises the corresponding appropriate antibody. Similarly, in certain embodiments a kit intended to be used for the labeling of polypeptides in living organisms will contain puromycin analog formulated such that it can be administered to a living organism. In certain embodiments, a kit intended to be used for screening compounds for their ability to induce or inhibit protein synthesis may include cells comprising labeled polypeptides of the present invention.

Certain inventive kits may further comprise buffers and/or reagents useful to perform a bioorthogonal reaction. In certain embodiments, a kit further comprises buffers and/or reagents useful to perform a [3+2] cycloaddition reaction, such as aqueous medium and Cu(I).

An inventive kit may further comprise one or more of: wash buffers and/or reagents, cell fixation buffers and/or reagents, immunohistochemical buffers and/or reagents, DAB photoconversion buffers and/or reagents, and detection means. In certain embodiment, the buffers and/or reagents are optimized for the particular labeling/detection technique for which the kit is intended. Protocols for using these buffers and reagents for performing different steps of the procedure may also be included in the kit.

In certain embodiments, a kit according to the present invention contains instruments (e.g., needle biopsy syringe) and/or reagents for the isolation of cells from an organism.

Reagents may be supplied in a solid (e.g., lyophilized) or liquid form. In certain embodiments, kits of the present invention comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the labeling/detection assay may also be provided. In certain embodiments, individual containers of a kit are maintained in close confinement for commercial use.

In certain embodiments, a kit according to the present invention further comprises instructions for use. Instructions for using a kit according to one or more inventive methods may comprise instructions for labeling polypeptides, instructions for measuring protein synthesis, instructions for interpreting results obtained as well as a notice in the form prescribed by a governmental agency (e.g., FDA) regulating the manufacture, use or sale of pharmaceuticals or biological products.

These and other aspects of the present invention will be further appreciated upon consideration of the following Examples, which are intended to illustrate certain particular embodiments of the invention but are not intended to limit its scope, as defined by the claims.

EXAMPLES

General Methods

All solvents and reagents were obtained from commercial suppliers and were used without further purification. NMR spectra were recorded on a Varian Oxford AS600 600 MHz NMR instrument. NMR chemical shifts were expressed in ppm relative to internal solvent peaks, and coupling constants were measured in Hz. (br=broad). Mass spectra were determined on a Waters Micromass ZQ instrument, using an ESI source coupled to a Waters 2525 HPLC system operating in reverse mode, with an Waters Sunfire™ C18 5 µM 4.6×50 mm column. Flash chromatography was performed using a Biotage Isolera One flash purification system.

Example 1

Synthesis of O-propargyl-puromycin

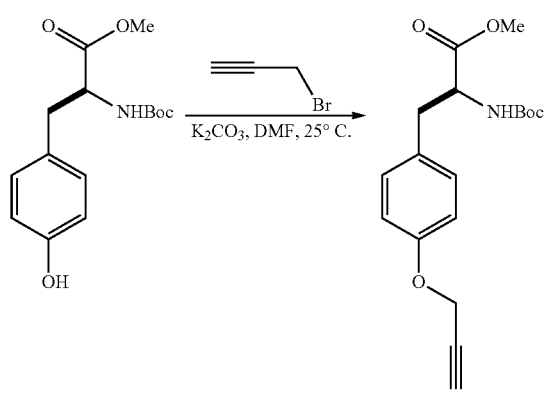

O-Propargyl Boc-Tyr-OMe (1). A solution of Boc-Tyr-OMe (2.01 g, 6.80 mmol), propargyl bromide (80% wt solution in toluene, 910 μL, 8.16 mmol), $K_2CO_3$ (2.82 g, 20.4 mmol) in dry DMF (19 mL) was stirred for 17 h at room temperature. After dilution with water (200 mL), the resulting mixture was extracted with EtOAc (2×100 mL). The combined organic layers were washed with saturated $NaHCO_3$ and brine followed by drying over $Na_2SO_4$. After removal of the solvent in vacuo, the crude product was obtained as a yellow liquid and was used in the next step without further purification.

O-Propargyl Boc-Tyrosine N-Hydroxysuccinimide Ester (3). Disuccinimidyl carbonate (2.46 g, 9.60 mmol) was added to a solution of 2 (2.04 g, 6.40 mmol) and pyridine (1.04 mL, 12.80 mmol) in acetonitrile (16 ml). The reaction was stirred at room temperature for 15 h, during which the solution became clear and evolved gas. The reaction mixture was added to EtOAc, washed twice with 1 N HCl and twice with saturated $NaHCO_3$, dried over $Na_2SO_4$, and concentrated in vacuo to yield a white solid (1.90 g, 71%), which was used in the next step without further purification.

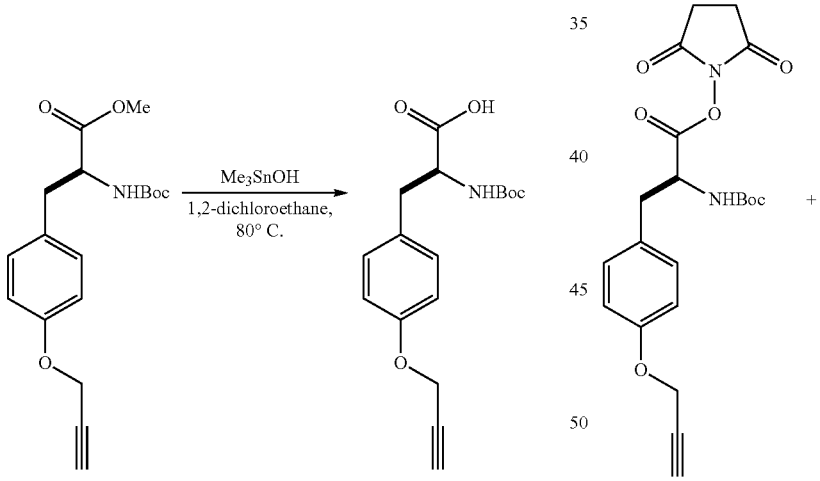

O-Propargyl Boc-Tyr-OH (2). A solution of O-Propargyl Boc-Tyr-OMe 1 (2.27 g, 6.80 mmol) was dissolved in 27 mL 1,2-dichloroethane and after addition of trimethyltin hydroxide (3.69 g, 20.4 mmol), the mixture was heated to 80° C. until TLC analysis indicated a complete reaction. The mixture was then concentrated in vacuo, and the residue was dissolved in EtOAc (100 mL). The organic layer was washed with aqueous HCl (5%) (3×60 mL), then washed with brine and dried over $Na_2SO_4$. After removal of the solvent in vacuo, the residue was purified by flash column chromatography ($SiO_2$, stepwise gradient from 2-20% MeOH in $CH_2Cl_2$) to give 2 (2.08 g, 96%) as a clear oil.

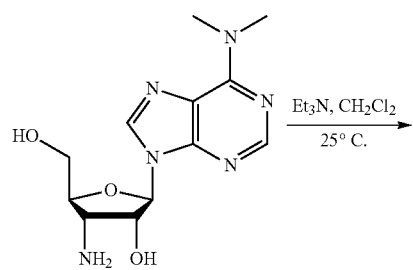

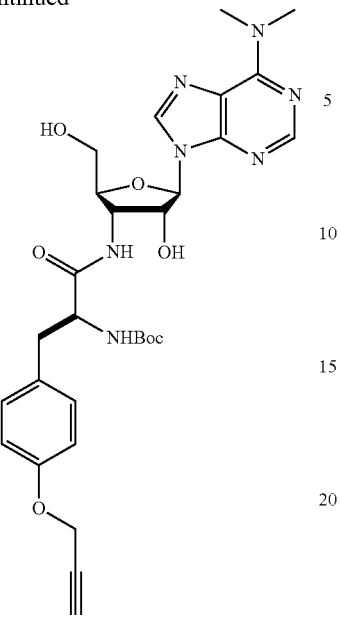

tert-Butyl ((S)-1-(((2S,3S,4R,5R)-5-(6-(dimethylamino)-9H-purin-9-yl)-4-hydroxy-2-(hydroxymethyl)tetrahydrofuran-3-yl)amino)-1-oxo-3-(4-(prop-2-yn-1-yloxy)phenyl)propan-2-yl)carbamate (O-propargyl Boc-puromycin) (4). O-Propargyl Boc-Tyrosine N-hydroxysuccinimide ester 3 (1.42 g, 3.40 mmol) and triethylamine (0.47 mL, 3.40 mmol) were added to a solution of puromycin aminoglycoside (500.0 mg, 1.70 mmol) in $CH_2Cl_2$ (15 mL). The solution was stirred at room temperature for 1.5 h and then directly purified by flash chromatography ($SiO_2$, step-wise gradient from 2-10% MeOH in $CH_2Cl_2$), to yield the product as a white solid (480 mg, 47%). $^1$H NMR (600 MHz, DMSO-$d_6$): δ 8.44 (s, 1H), 8.24 (s, 1H), 8.00 (d, J=7.8 Hz, 1H), 7.21 (d, J=8.4 Hz, 2H), 6.84-6.92 (m, 3H), 6.05 (d, J=4.8 Hz, 1H), 5.99 (d, J=3.0 Hz, 1H), 5.15 (t, J=5.4 Hz, 1H), 4.74 (d, J=1.8 Hz, 2H), 4.43-4.53 (m, 2H), 4.17-4.24 (m, 1H), 3.91-3.96 (m, 1H), 3.64-3.72 (m, 1H), 3.10-3.62 (m, 8H), 2.91 (dd, J=13.8, 4.2 Hz, 1H), 2.70 (dd, J=13.8, 10.2 Hz, 1H), 1.30 (s, 9H); LC/MS (ESI, m/z): calcd for $C_{29}H_{37}N_7O_7[M+H]^+$ 596. found 596.

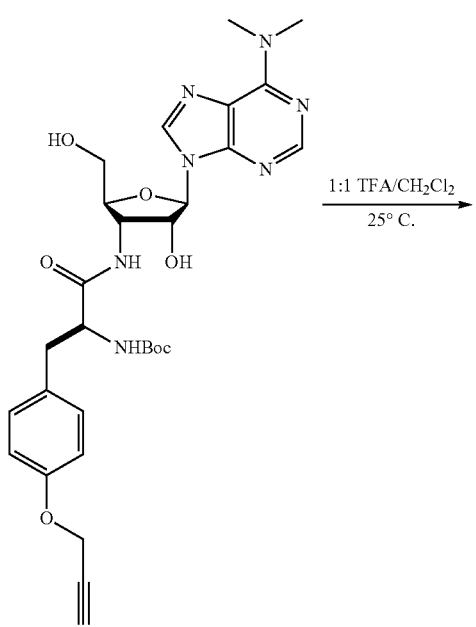

1:1 TFA/$CH_2Cl_2$
25° C.

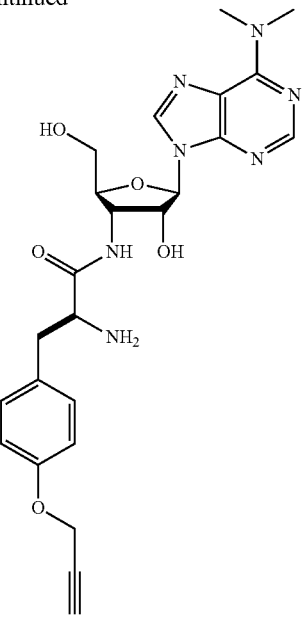

(S)-2-Amino-N-((2S,3S,4R,5R)-5-(6-(dimethylamino)-9H-purin-9-yl)-4-hydroxy-2-(hydroxymethyl)tetrahydrofuran-3-yl)-3-(4-(prop-2-yn-1-yloxy)phenyl)propanamide (O-propargyl-puromycin) (5). O-Propargyl Boc-Puromycin 4 (480 mg, 0.81 mmol) was dissolved in a 1:1 TFA (4 mL) and $CH_2Cl_2$ (4 mL) mixture and then stirred at room temperature for 30 min. Volatiles were evaporated in vacuo and the residue was dissolved in $CH_2Cl_2$. The solution was poured into saturated aqueous $NaHCO_3$. The organic layer was dried over $Na_2SO_4$ and evaporated to dryness in vacuo. The residue was purified by flash chromatography ($SiO_2$, step-wise gradient from 5-15% MeOH in $CH_2Cl_2$) to afford the O-propargyl-puromycin 5 (111 mg, 28%) as a white solid. $^1$H NMR (600 MHz, DMSO-$d_6$): δ 8.44 (s, 1H), 8.24 (s, 1H), 8.06 (br, 1H), 7.17 (d, J=8.4 Hz, 2H), 6.90 (d, J=8.4 Hz, 2H), 6.13 (d, J=5.4 Hz, 1H), 5.98 (d, J=3.0 Hz, 1H), 5.13 (t, J=5.4 Hz, 1H), 4.74 (d, J=1.8 Hz, 2H), 4.42-4.51 (m, 2H), 3.91-3.96 (m, 1H), 3.66-3.72 (m, 1H), 3.26-3.58 (m, 9H), 2.92 (dd, J=14.4, 4.8 Hz, 1H), 2.52-2.58 (m, 1H), 2.02 (br, 2H); $^{13}$C NMR (150 MHz, DMSO-$d_6$): δ 174.6, 155.7, 154.3, 151.8, 149.6, 137.9, 131.3, 130.2, 119.6, 114.5, 89.4, 83.5, 79.4, 78.0, 73.2, 61.0, 56.1, 55.3, 50.0, 40.4, 40.0; HRMS: (ESI, m/z) calcd $[M+H]^+$ for $C_{24}H_{29}N_7O_5$: 496.2303. found 496.2308.

Example 2

OP-puro Labeling of Cultured Cells and Detection by Fluorescence Microscopy

A chemically-tagged puro was developed to label newly synthesized proteins, for subsequent imaging by fluorescence microscopy and for isolation by affinity chromatography. Structure-activity studies of puro (Nathans et al. *Nature* 197: 1076-1077 (1963); Pestka et al. *Antimicrob. Agents. Chemother.* 4(1):37-43 (1973); Eckermann et al. *Eur. J. Biochem.* 41(3):547-554 (1974); Vanin et al. *FEBS Lett.* 40(1): 124-126 (1974); Lee et al. *J. Med. Chem.* 24(3):304-308 (1981)) indicated that the molecule tolerates modifications of the O-Me phenyl ring, without significant loss of activity. O-propargyl-puromycin (OP-puro, FIG. 1B), a puro analog that bears a terminal alkyne group, was synthesized to allow detection of nascent polypeptide chains by copper(I)-catalyzed azide-alkyne cycloaddition (CuAAC) (Wang et al., *J. Am. Chem. Soc.* 125(11):3192-3193).

NIH-3T3 cells were grown on glass coverslips in Dulbecco modified Eagle's medium (DMEM) supplemented with 10% bovine calf serum, penicillin and streptomycin. OP-puro was added to cells in complete culture medium. After incubation for the desired amount of time, the cells were washed with PBS and then fixed with cold methanol for 2 minutes at −20° C. The cells were washed with TBS (10 mM Tris pH 7.5, 150 mM NaCl), permeabilized with TBST (TBS with 0.2% Triton X-100), and then washed with TBS again. CuAAC detection of OP-puro incorporated into nascent protein was performed by reacting the fixed cells for 30 minutes at room temperature with 20 µM Alexa568-azide, as described (Salic et al., *Proc. Natl. Acad. Sci. USA* 105(7):2415-2420 (2008)). Cu(I) was generated in situ from CuSO4 and ascorbic acid. After staining, the coverslips were washed several times with TBST, counterstained with Hoechst, and mounted in standard mounting media. The stained cells were imaged by DIC and by epi-fluorescence microscopy on a Nikon TE2000U microscope equipped with an OrcaER camera (Hammamatsu), and 20× PlanApo 0.75 NA and 40× PlanApo 0.95 NA air objectives (Nikon). Images were collected using Metamorph image acquisition software (Applied Precision).

To determine if protein synthesis is required for OP-puro incorporation into nascent polypeptides, cells were incubated with OP-puro, in the presence or absence of 50 micrograms/mL cycloheximide (CHX), added to the cells 15 minutes before OP-puro. This concentration of CHX was determined to completely block protein translation in cells.

When cultured cells were treated for one hour with varying concentrations of OP-puro followed by fixation and staining with Alexa568-azide, a specific fluorescent signal proportional to the concentration of OP-puro was detected (FIG. 2A). OP-puro incorporation required functional ribosomes and was abolished if cells were treated with CHX (FIG. 2A, right-most panel), as seen before by autoradiography (FIG. 1E). The intensity of the OP-puro stain increased with incubation time (FIG. 2B) and reached saturation after about one hour. A strong signal was seen after as little as 15 minutes of incubation with OP-puro. While the OP-puro staining pattern was mostly cytoplasmic, many cells also showed a punctate nuclear stain, suggesting that the truncated protein-OP-puro conjugates released from ribosomes can localize to various subcellular compartments. At later time points (see the 3 hour image of FIG. 2B), the cytoplasmic OP-puro signal is significantly decreased, suggesting that the polypeptide-OP-puro conjugates are turned over.

The OP-puro conjugates do not form if protein synthesis is inhibited by CHX, which blocks translational initiation, demonstrating that translating ribosomes are required for OP-puro incorporation into nascent polypeptide chains, at the level of polypeptide chain elongation. These results demonstrate that OP-puro is a translation inhibitor that forms covalent adducts with elongating polypeptide chains on the ribosome. A concentration of 25 microM OP-puro blocked protein synthesis almost completely, defining a concentration that should capture almost quantitatively the proteins synthesized by a given cell in the form of OP-puro-polypeptide conjugates.

To determine the effect of inhibiting the proteasome on the stability of OP-puro-conjugated polypeptide chains, cells were pulse-labeled with 50 microM OP-puro for 15 minutes and were then incubated in complete media supplemented with 50 micrograms/mL CHX (to block further incorporation of OP-puro into nascent proteins), in the presence or absence of 5 microM of the proteasome inhibitor bortezomib. Cells were fixed at the indicated times and were stained in parallel with Alexa568-azide. Two negative controls were used: 1) untreated cells; and 2) cells pre-incubated with 50 micrograms/mL CHX for 15 minutes, followed by incubation with 50 microM OP-puro and 50 micrograms/mL CHX for another 15 minutes.

Polypeptide-puro conjugates have been reported to be unstable (Goldberg, *Proc. Natl. Acad. Sci. USA* 69(2):422-426 (1972); Wharton et al. *FEBS Lett.* 168(1):134-138 (1984)). Cultured cells were labeled with a short pulse of OP-puro, after which the cells were washed and chased in the absence or presence of the proteasome inhibitor bortezomib (Adams et al. *Cancer Invest.* 22(2):304-311 (2004)). In the absence of bortezomib, OP-puro conjugates are unstable and disappear from cells in under 1 hour (FIG. 2C, middle panel). If the proteasome is inhibited with bortezomib, the OP-puro conjugates become stable (FIG. 2C, bottom row of panels), demonstrating that the rapid disappearance of OP-puro conjugates is due to degradation by the proteasome. We conclude that the majority of conjugates of OP-puro with nascent polypeptide chains are short-lived, which suggests that the OP-puro signal is a good reflection of instant protein synthesis in cells.

Example 3

Inhibition of Translation by OP-puro

A plasmid carrying a GFP fusion of the mouse Suppressor of Fused (SuFu) gene under the control of an SP6 RNA polymerase promoter was used to generate 35[S]-Met-labeled GFP-SuFu by in vitro translation in rabbit reticulocyte lysates (TNT SP6 Quick coupled transcription/translation kit, Promega), according to the manufacturer's instructions. Translation reactions were performed for 1 hour at 30° C., in the absence or presence of varying concentrations of puro and OP-puro. The reactions were stopped by addition of SDS-PAGE sample buffer with 50 mM DTT and boiling. Equal amounts of lysate were separated by SDS-PAGE and the amount of in vitro translated GFP-SuFu was determined by autoradiography.

To measure translation inhibition in cells, human embryonic kidney 293T cells were pre-incubated for 30 minutes with varying concentrations of puro or OP-puro, in complete media. The cells were then incubated for 3 hours in Met-free media supplemented with 35[S]-Met (from Perkin-Elmer, at 100 microCi/mL final concentration), in the continued presence of varying concentrations of puro or OP-puro. The cells were harvested, lyzed in TBS with 1% Triton X-100 and protease inhibitors (Complete tablets, Roche), and centrifuged for 15 minutes at 20,000 g in a refrigerated centrifuge. The clarified cells lysates were analyzed by SDS-PAGE, followed by autoradiography, to measure bulk protein translation.

OP-puro inhibits protein synthesis, both in reticulocyte lysates (FIG. 1C) and in cultured cells (FIG. 1D), displaying a potency 2-3 fold lower than that of unmodified puro.

Example 4

Affinity Purification of Nascent Polypeptide-OP-puro Conjugates

Human 293T cells were labeled for 1 hour in Met-free DMEM supplemented with 10% dialyzed fetal bovine serum and 35[S]-Met (100 microCi/mL final). The cells were then incubated in the same media, in the presence of 10 microM puro, 25 microM OP-puro or 25 microM OP-puro and 50 micrograms/mL CHX, for an additional 1 hour. The cells were harvested, washed with ice cold PBS and then lyzed on ice in 100 mM Tris pH 8.5 with 1% Triton-X10 and protease inhibitors. The lysates were clarified by centrifugation for 15 minutes at 20,000 g and 4° C., and were then subjected to CuAAC with biotin azide for 30 minutes at room temperature. The final concentrations in the CuAAC reaction were: 100 microM biotin azide, 1 mM $CuSO_4$ and 50 mM ascorbic acid (added last to the lysates). Biotinylated proteins were diluted in binding buffer (20 mM Tris pH 8, 500 mM NaCl, 1% Triton-X100) and were bound to Neutravidin beads (Pierce). After extensive washes with binding buffer, bound proteins were eluted, separated by SDS-PAGE and detected by autoradiography. OP-puro formed conjugates with 35[S]-Met-labeled nascent polypeptide chains (FIG. 1E), which can be specifically retrieved on streptavidin beads.

Example 5

Use of OP-puro to Image Protein Synthesis in Animals

One hundred microliters of a 20 mM solution of OP-puro in PBS were injected intraperitoneally into a 3-week old mouse, while a mouse injected with 100 microliters of PBS was used as negative control. Various organs were harvested after one hour and were fixed in formalin overnight. Organ fragments were embedded in paraffin, sectioned, and washed with xylene to remove the paraffin. After washing with ethanol and rehydration in TBS, the tissue sections were stained with 20 microM tetramethylrhodamine(TMR)-azide, as described (Salic et al., *Proc. Natl. Acad. Sci. USA* 105(7):2415-2420 (2008)). The tissue sections were counterstained with Hoechst, mounted in standard mounting media and were then imaged by fluorescence microscopy and DIC.

Figure 4:
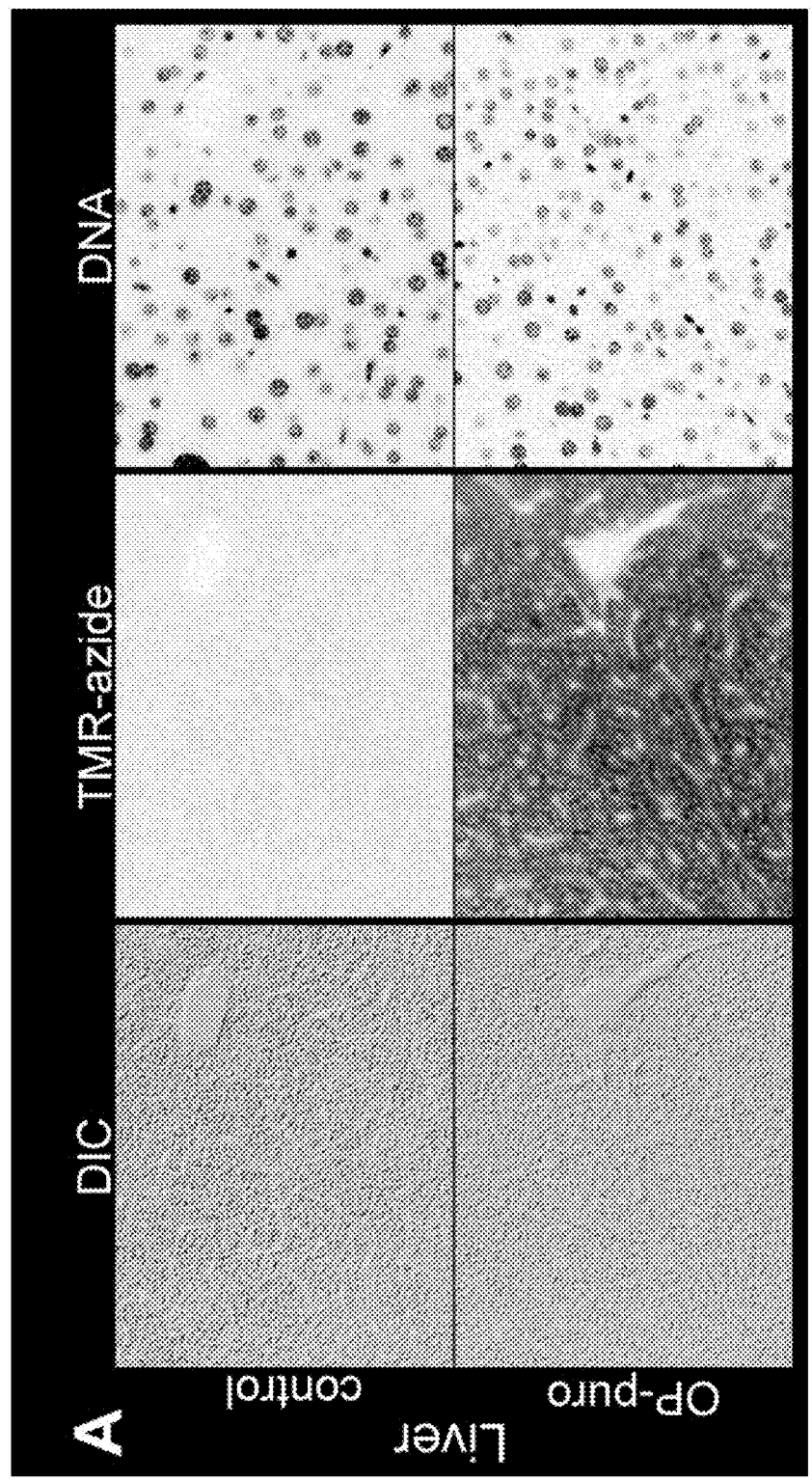
FIG. 4 depicts imaging of protein synthesis in whole animals with OP-puro. One hundred microliters of a 20 mM OP-puro solution in PBS or PBS alone (negative control) were injected intraperitoneally into mice. Organs were harvested 1 hour later and were fixed in formalin. Organ fragments were embedded in paraffin, sectioned, and stained using CuAAC with 15 tetramethylrhodamine (TMR)-azide, followed by imaging by fluorescence microscopy and by DIC. (A) Section through mouse liver. OP-puro stains strongly all hepatocytes. (B) Section through mouse kidney. (C) Section through mouse spleen.
Figure 4:
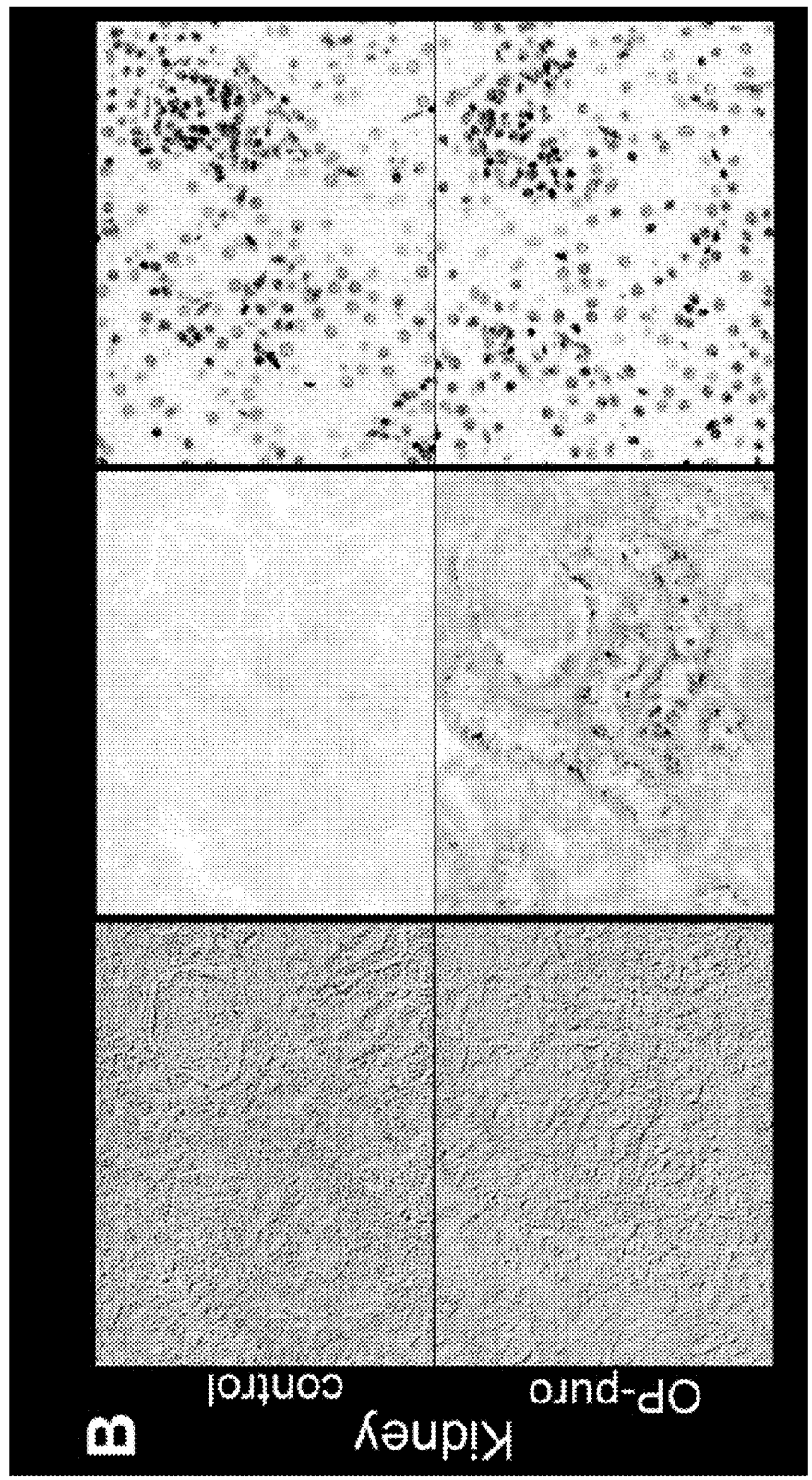
Figure 4:
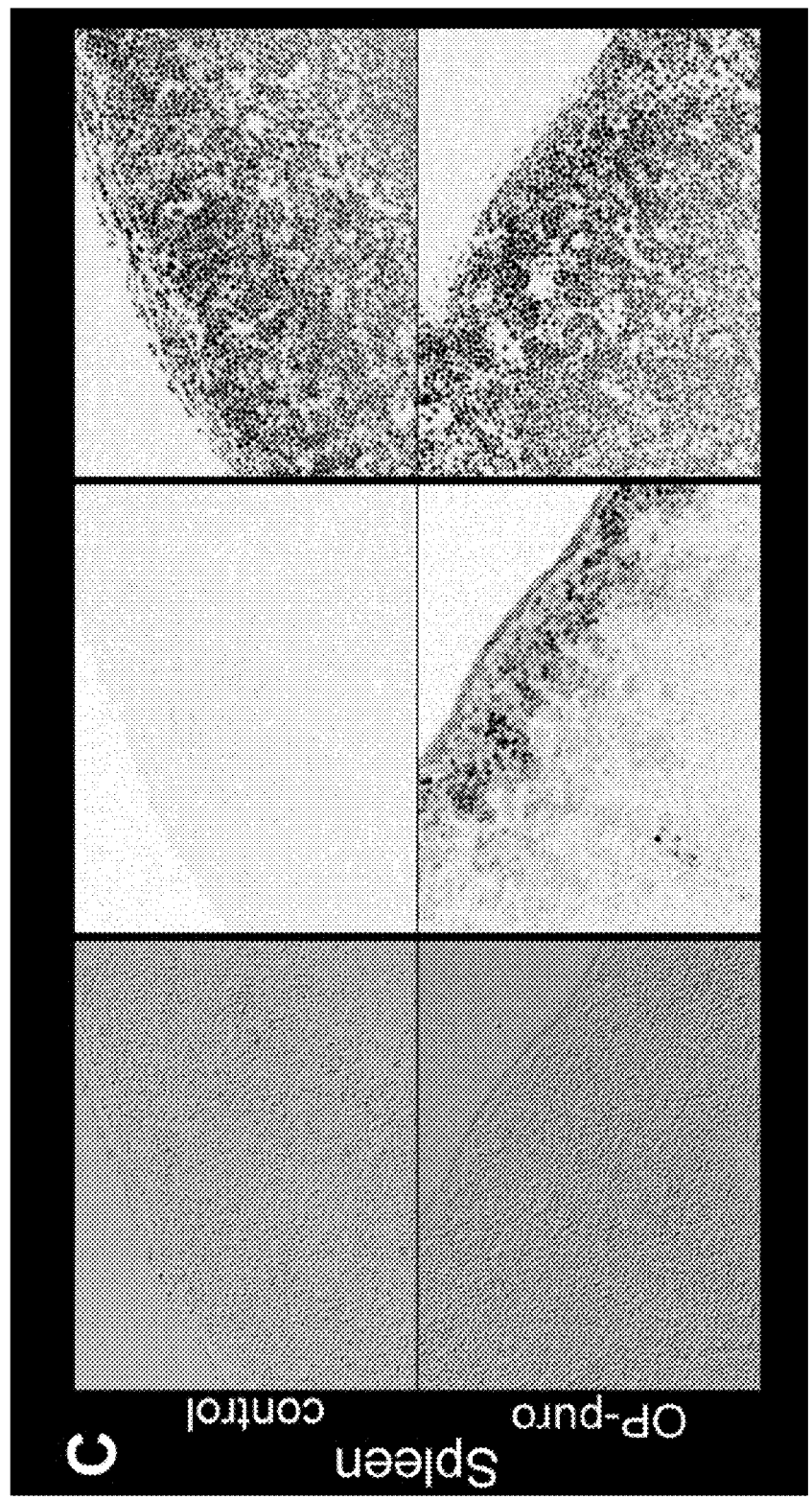

Mice were injected intraperitoneally with OP-puro, and tissues were harvested 1 hour later, fixed and stained with fluorescent azide, either after sectioning or in whole mount. As shown in FIGS. 3 and 4, tissues from uninjected mice showed low non-specific staining, while tissues from OP-puro-injected mice displayed specific patterns of OP-puro incorporation into nascent proteins. In the small intestine, translation was strongest in cells in the crypts and at the base of intestinal villi (FIG. 3A), consistent with the high proliferative and secretory activity of these cells. The stain was particularly strong in Paneth cells, which are located close to the base of the crypts and are filled with secretory vesicles. The intense OP-puro labeling of vesicles in Paneth cells (FIG. 3A, bottom panels) suggests that prematurely-terminated, OP-puro-conjugated secretory proteins are translocated into the ER lumen, as described before for puro (Andrews et al., *Biochem. J.* 121(4):683-694 (1971)). The same pattern of OP-puro labeling was observed in whole mount stains of the small intestine (FIG. 3B), suggesting that OP-puro is uniquely suited for visualizing protein synthesis in whole tissues and organs, with high sensitivity.

Patterns of protein synthesis in other mouse tissues surveyed (liver, kidney, and spleen) are shown in FIG. 4. The level of protein synthesis varies between tissues, being the strongest in hepatocytes (FIG. 4A), consistent with the high levels of protein synthesis in the liver. Protein synthesis levels are uniformly high in hepatocytes but can vary significantly within other tissues, such as spleen (FIG. 4C), in which the strongest OP-puro signal is found at the organ's periphery, under the capsule. Interestingly, in muscle the OP-puro stain shows a striking striated pattern (FIG. 3C), suggesting that some muscle OP-puro-protein conjugates are properly incorporated into sarcomeres, This method might thus be suitable for imaging the assembly and turnover of structures such as sarcomeres.

Example 6

Preparation of azido-puromycin

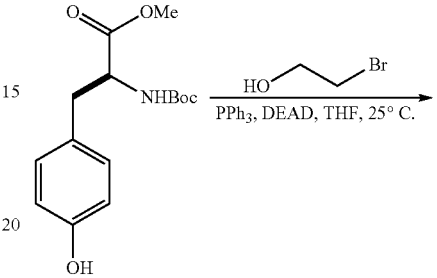

(S)-Methyl 3-(4-(2-bromoethoxy)phenyl)-2-((tert-butoxycarbonyl)amino)propanoate (1A). 2-Bromo-ethanol (0.61 mL, 8.03 mmol), followed by $PPh_3$ (3.16 g, 12.05 mmol) was added to a solution of Boc-Tyr-OMe (2.85 g, 9.64 mmol) in anhydrous THF (50 mL). The mixture was cooled to 0° C. and DEAD (5.5 mL of 40% wt solution in toluene, 12.05 mmol) was added. The mixture was allowed to warm at room temperature and was stirred overnight. After the reaction was finished, the solvent was evaporated and the residue dissolved in EtOAc (100 mL) was washed with NaOH (0.1 M, 2×50 mL), followed by brine. The organic phase was dried over $Na_2SO_4$ and evaporated. The crude product was purified by flash column chromatography ($SiO_2$, step-wise gradient from 2-40% EtOAc in Hexanes) to give 1A (1.61 g, 50%) as a white solid. $^1$H NMR (600 MHz, $CDCl_3$): δ 7.04 (2H, d, J=8.4 Hz), 6.84 (2H, d, J=8.4 Hz), 4.96 (1H, d, J=7.8 Hz), 4.51-4.58 (1H, m), 4.27 (2H, t, J=6.6 Hz), 3.71 (3H, s), 3.62 (2H, t, J=6.6 Hz), 3.06 (1H, dd, J=13.8, 5.4 Hz), 3.00 (1H, dd, J=13.8, 5.4 Hz), 1.42 (9H, s); $^{13}$C NMR (150 MHz, $CDCl_3$): δ 172.3, 157.2, 155.1, 130.4, 128.8, 114.8, 79.9, 67.9, 54.5, 52.2, 37.5, 29.1, 28.3; MS (ESI, m/z): 424 (M+Na)$^+$.

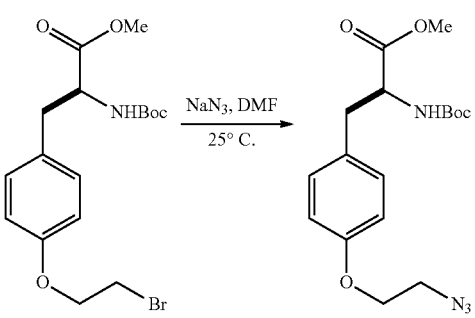

(S)-Methyl 3-(4-(2-azidoethoxy)phenyl)-2-((tert-butoxycarbonyl)amino)propanoate (2A). A mixture of 1A (1.61 g, 4.0 mmol) and sodium azide (0.78 g, 12.0 mmol) in DMF (27 mL) was stirred at room temperature for 20 h. The reaction mixture was diluted with H$_2$O (120 mL) and extracted with EtOAc (3×60 mL). The combined organic phases were washed with brine, dried over Na$_2$SO$_4$ and concentrated in vacuo. The residue was purified by flash column chromatography (SiO$_2$, step-wise gradient from 2-40% EtOAc in Hexanes) to give 2A (1.46 g, 100%) as a clear oil. $^1$H NMR (600 MHz, CDCl$_3$): δ 7.05 (2H, d, J=8.4 Hz), 6.85 (2H, d, J=8.4 Hz), 4.97 (1H, d, J=7.8 Hz), 4.51-4.58 (1H, m), 4.13 (2H, t, J=5.4 Hz), 3.71 (3H, s), 3.58 (2H, t, J=5.4 Hz), 3.06 (1H, dd, J=13.8, 5.4 Hz), 3.00 (1H, dd, J=13.8, 5.4 Hz), 1.42 (9H, s); $^{13}$C NMR (150 MHz, CDCl$_3$): δ 172.3, 157.3, 155.1, 130.4, 128.7, 114.6, 79.9, 66.9, 54.5, 52.2, 50.2, 37.5, 28.3; MS (ESI, m/z): 387 (M+Na)$^+$.

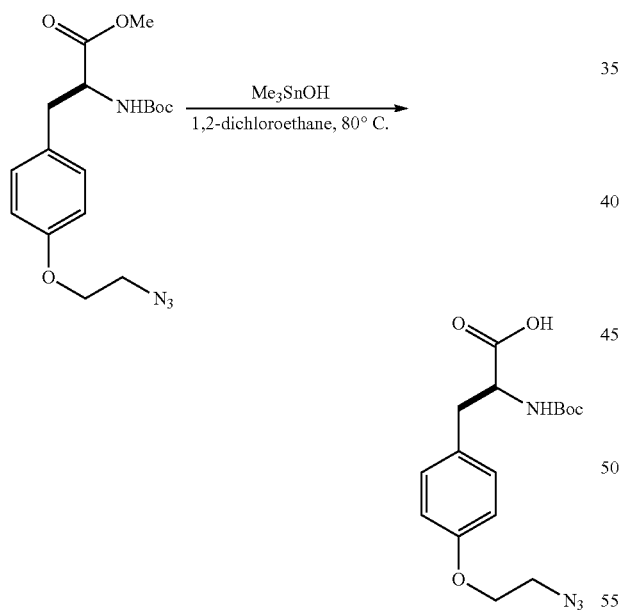

(S)-3-(4-(2-Azidoethoxy)phenyl)-2-((tert-butoxycarbonyl)amino)propanoic acid (3A). A solution of 2A (1.46 g, 4.0 mmol) was dissolved in 1,2-dichloroethane (20 mL) and after addition of trimethyltin hydroxide (2.17 g, 12.0 mmol), the mixture was heated at 80° C. until TLC analysis indicated a complete reaction. After completion of the reaction, the mixture was concentrated in vacuo, and the residue was taken up in EtOAc (80 mL). The organic layer was washed with aqueous HCl (5%) (3×50 mL). The organic layer was then washed with brine and dried over Na$_2$SO$_4$. After removal of the solvent in vacuo, the residue was purified by flash column chromatography (SiO$_2$, step-wise gradient from 2-20% MeOH in CH$_2$Cl$_2$) to give 3A (0.98 g, 70%) as a white solid. $^1$H NMR (600 MHz, CDCl$_3$): δ 7.11 (2H, d, J=8.4 Hz), 6.86 (2H, d, J=8.4 Hz), 4.94 (1H, d, J=7.2 Hz), 4.53-4.60 (1H, m), 4.13 (2H, t, J=5.4 Hz), 3.58 (2H, t, J=5.4 Hz), 3.14 (1H, dd, J=13.8, 5.4 Hz), 3.04 (1H, dd, J=13.8, 5.4 Hz), 1.43 (9H, s); $^{13}$C NMR (150 MHz, CDCl$_3$): δ 157.3, 155.5, 130.5, 128.8, 114.7, 80.2, 66.9, 54.7, 50.1, 37.0, 28.3; MS (ESI, m/z): 373 (M+Na)$^+$.

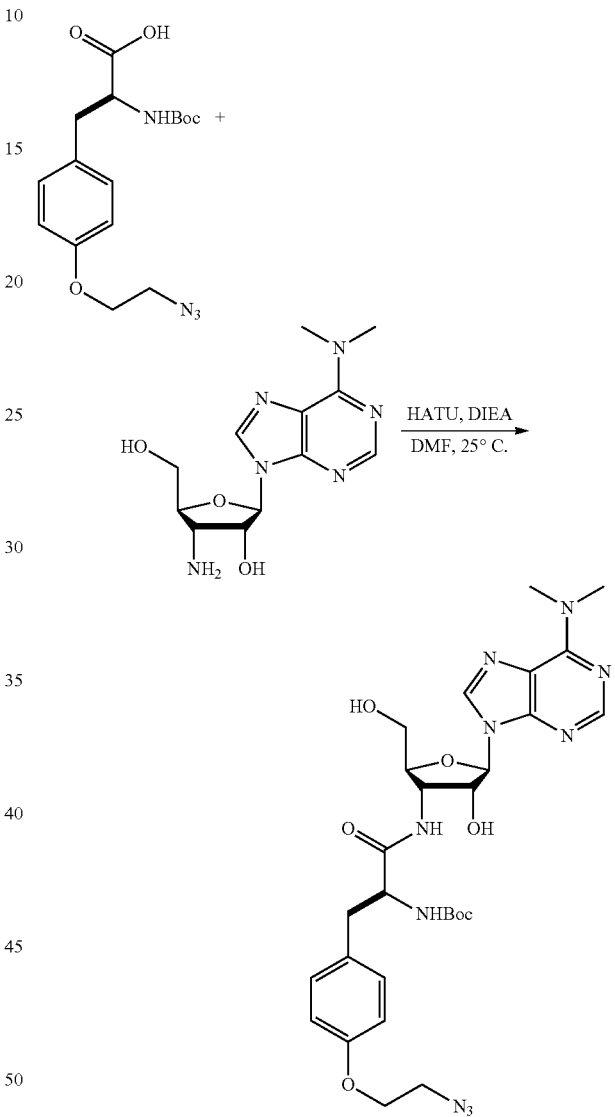

tert-Butyl ((S)-3-(4-(2-azidoethoxy)phenyl)-1-(((2S,3S,4R,5R)-5-(6-(dimethylamino)-9H-purin-9-yl)-4-hydroxy-2-(hydroxymethyl)tetrahydrofuran-3-yl)amino)-1-oxopropan-2-yl)carbamate (Boc-Puromycin Analog) (4A). 3A (289 mg, 0.82 mmol) and puromycin aminoglycoside (221 mg, 0.75 mmol) was dissolved in dry DMF (6 mL), followed by HATU (314 mg, 0.82 mmol) and diisopropylethylamine (0.26 mL, 1.5 mmol). The reaction mixture was then stirred at room temperature for 3 h, then diluted with H$_2$O (80 mL) and saturated NaHCO$_3$ (40 mL), extracted with EtOAc (3×40 mL). The combined organic phases were washed with brine, dried over Na$_2$SO$_4$ and concentrated in vacuo. The residue was purified by flash chromatography (SiO$_2$, step-wise gradient from 2-15% MeOH in CH$_2$Cl$_2$) to afford 4A (384 mg, 82%) as a white solid. $^1$H NMR (600 MHz, DMSO-d$_6$): δ 8.45

(1H, s), 8.24 (1H, s), 8.00 (1H, d, J=7.8 Hz), 7.21 (2H, d, J=8.4 Hz), 6.84-6.91 (3H, m), 6.06 (1H, d, J=4.8 Hz), 6.00 (1H, d, J=3.0 Hz), 5.16 (1H, t, J=5.4 Hz), 4.44-4.54 (2H, m), 4.21 (1H, dt, J=9.6, 4.8 Hz), 4.13 (2H, t, J=5.4 Hz), 3.92-3.98 (1H, m), 3.10-3.80 (10H, m), 2.92 (1H, dd, J=13.8, 4.8 Hz), 2.70 (1H, dd, J=13.8, 9.6 Hz), 1.31 (9H, s); $^{13}$C NMR (150 MHz, DMSO-$d_6$): δ 172.0, 156.5, 155.2, 154.3, 151.8, 149.7, 137.9, 130.5, 130.3, 119.6, 114.1, 89.3, 83.4, 78.0, 73.1, 66.7, 60.9, 55.9, 50.3, 49.6, 36.9, 28.1, 27.8; MS (ESI, m/z): 627 (M+H)$^+$.

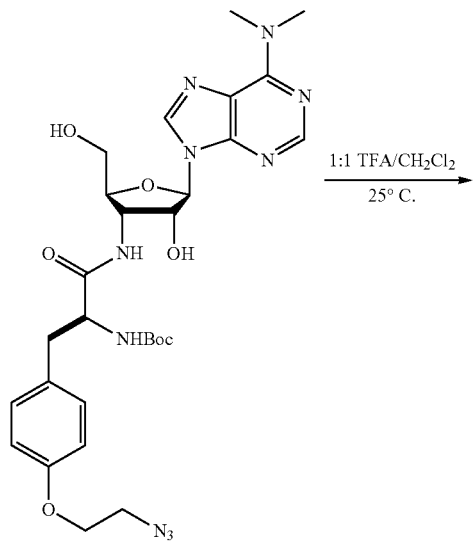

(S)-2-Amino-3-(4-(2-azidoethoxy)phenyl)-N-((2S,3S,4R,5R)-5-(6-(dimethylamino)-9H-purin-9-yl)-4-hydroxy-2-(hydroxymethyl)tetrahydrofuran-3-yl)propanamide (Azidoethyl-Puromycin, AE-Puro) (5A). Boc-Puromycin analog 4A (392 mg, 0.63 mmol) was dissolved in a 1:1 TFA (5 mL) and CH$_2$Cl$_2$ (5 mL) mixture and then stirred at room temperature for 30 min. Volatiles were evaporated in vacuo and the residue was dissolved into CH$_2$Cl$_2$. The solution was poured into a suspension of saturated aqueous NaHCO$_3$. The organic layer was dried over Na$_2$SO$_4$ and evaporated to dryness in vacuo. The residue was purified by flash chromatography (SiO$_2$, step-wise gradient from 2-15% MeOH in CH$_2$Cl$_2$) to afford Puromycin analog 5A (151 mg, 46%) as a white solid. $^1$H NMR (600 MHz, DMSO-$d_6$): δ 8.45 (1H, s), 8.24 (1H, s), 8.06 (1H, br), 7.17 (2H, d, J=8.4 Hz), 6.87 (1H, d, J=8.4 Hz), 6.14 (1H, d, J=4.8 Hz), 5.98 (1H, d, J=2.4 Hz), 5.14 (1H, t, J=5.4 Hz), 4.42-4.52 (2H, m), 4.14 (2H, t, J=5.4 Hz), 3.92-3.97 (1H, m), 3.10-3.80 (12H, m), 2.92 (1H, dd, J=13.8, 5.4 Hz), 2.55 (1H, dd, J=13.8, 9.0 Hz), 1.72 (2H, br); $^{13}$C NMR (150 MHz, DMSO-$d_6$): δ 174.8, 156.5, 154.3, 151.8, 149.6, 137.9, 131.1, 130.3, 119.6, 114.2, 89.4, 83.6, 79.1, 73.2, 66.7, 61.0, 56.3, 50.0, 49.6, 40.1; MS (ESI, m/z): 527 (M+H)$^+$.

Example 7

Inhibition of Translation by AE-puro

Figure 5:
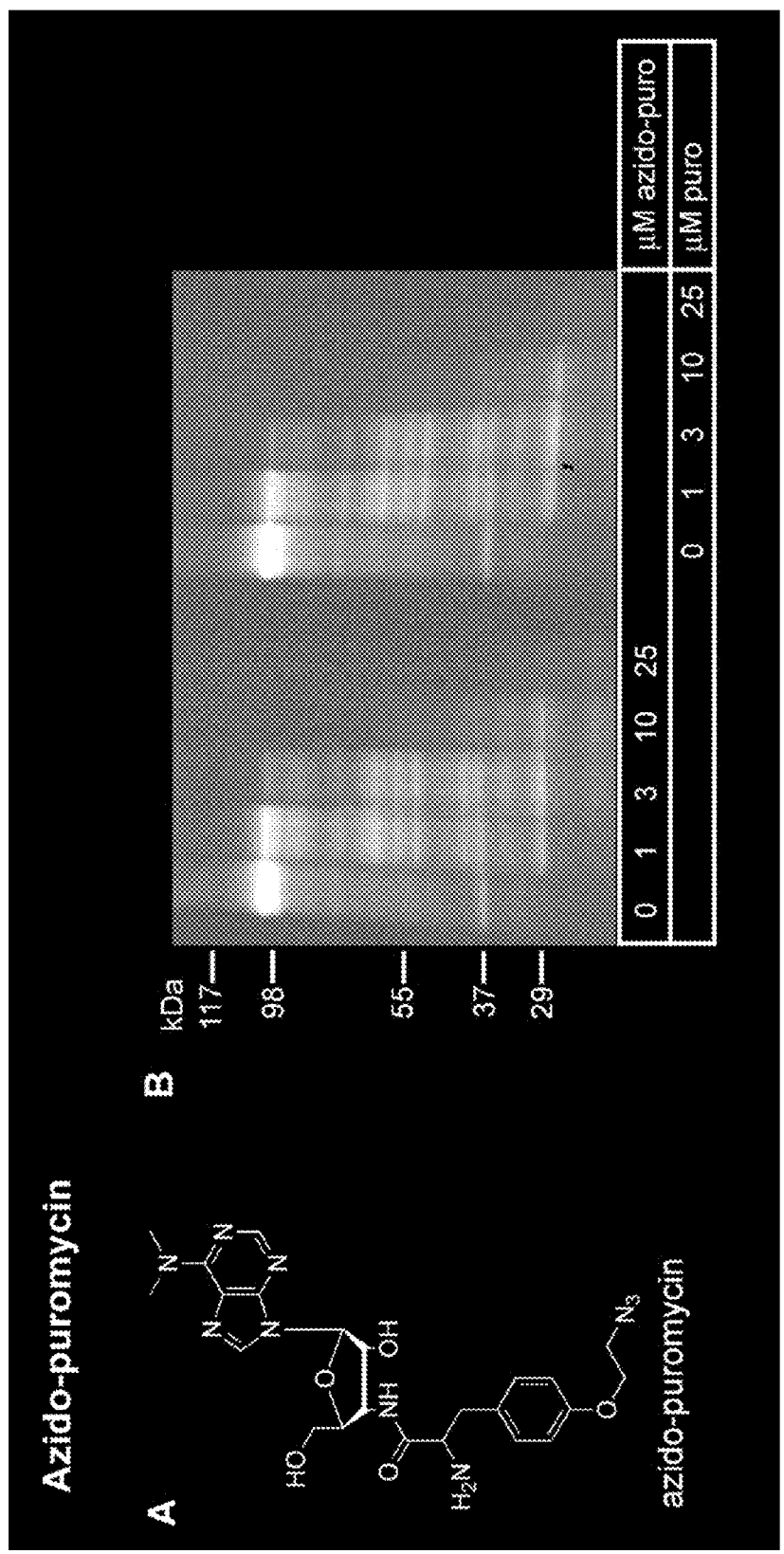
FIG. 5 shows that O-azidoethyl-puromycin (AE-puro), an azido puromycin (puro) analog, is a potent protein synthesis inhibitor. (A) Structure of AE-puro, which bears a terminal azide group. (B) Inhibition of protein translation in vitro by puro and AE-puro. A $^{35}$S-methionine-labeled protein (a GFP fusion of mouse Suppressor of Fused) was generated by translation in rabbit reticulocyte lysates, in the absence or presence of varying concentrations of puro and AE-puro. The translation reactions were separated by SDS-PAGE, and the translated protein was visualized by autoradiography. AE-puro inhibits protein synthesis in a dose-dependent manner.

A plasmid carrying a GFP fusion of the mouse Suppressor of Fused (SuFu) gene under the control of an SP6 RNA polymerase promoter was used to generate $^{35}$S-Met-labeled GFP-SuFu by in vitro translation in rabbit reticulocyte lysates (TNT SP6 Quick coupled transcription/translation kit, Promega), according to the manufacturer's instructions. Translation reactions were performed for 1 hour at 30° C., in the absence or presence of varying concentrations of puro and AE-puro (azido-puromycin, FIG. 5A). The reactions were stopped by addition of SDS-PAGE sample buffer with 50 mM DTT and boiling. Equal amounts of lysate were separated by SDS-PAGE and the amount of in vitro translated GFP-SuFu was determined by autoradiography. AE-puro inhibits protein synthesis in reticulocyte lysates (FIG. 5B) with a potency equal to that of unmodified puromycin.

OTHER EMBODIMENTS

This application refers to various issued patents, published patent applications, journal articles, books, manuals, and other publications, all of which are incorporated herein by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:
1. A compound of Formula (I):

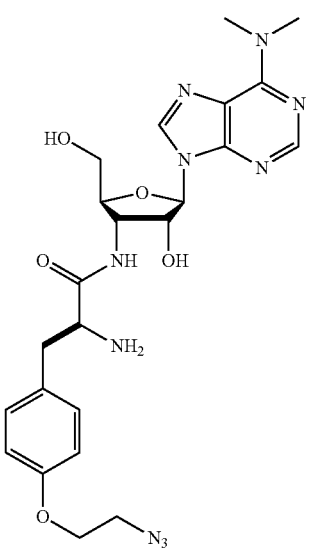

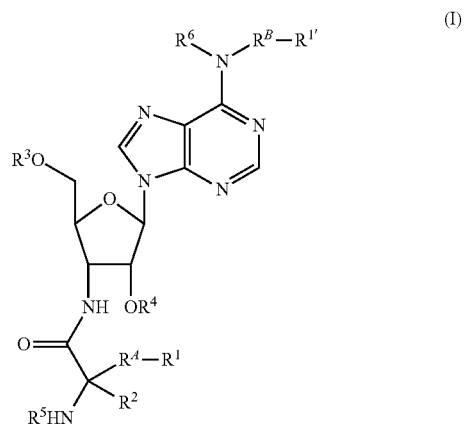

wherein
- $R^A$ is a bond or an optionally substituted aliphatic divalent moiety;
- $R^B$ is a bond or a $C_{1-6}$ aliphatic divalent moiety;
- $R^1$ is optionally substituted alkynyl;
- $R^{1'}$ is hydrogen;
- $R^2$ is hydrogen or $C_{1-6}$ aliphatic;
- $R^3$, $R^4$, and $R^5$ are each independently hydrogen or a protecting group; and
- $R^6$ is hydrogen or $C_{1-6}$ aliphatic;

or a salt thereof.

2. The compound of claim 1, wherein $R^1$ is unsubstituted alkynyl.

3. The compound of claim 1, wherein the compound is of Formula (II):

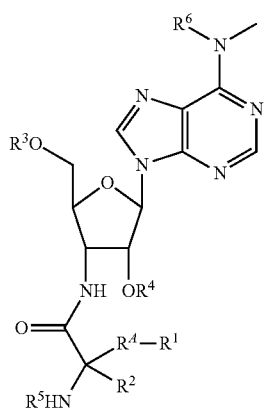

or a salt thereof.

4. The compound of claim 1, wherein the compound is of Formula (III):

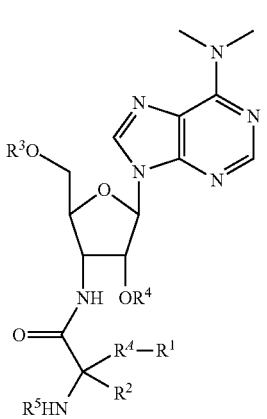

or a salt thereof.

5. The compound of claim 1, wherein $R^A$ is a bond, or an optionally substituted alkyl divalent moiety.

6. The compound according to claim 1, wherein $R^1$ is a propargyl group.

7. The compound according to claim 1, wherein $R^3$, $R^4$, and $R^5$ are hydrogen.

8. The compound according to claim 1, wherein the compound is of formula (I-a):

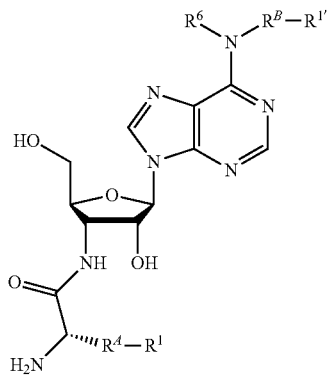

or a salt thereof.

9. The compound according to claim 1, wherein the compound is of the formula:

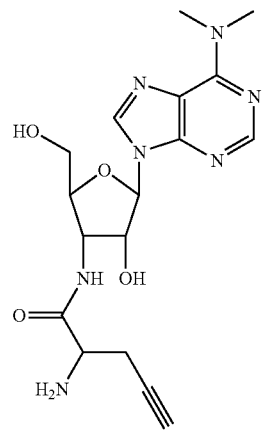

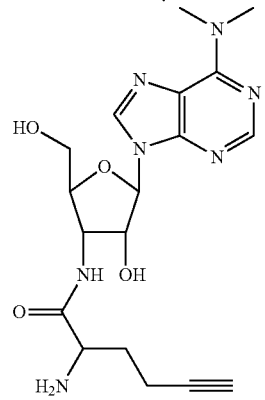

or a salt thereof.

10. A method of labeling a polypeptide comprising:
providing a conjugate of a polypeptide and a first compound of claim 1, wherein each one of the first compound and the conjugate comprises an optionally substituted alkynyl moiety; and
contacting the conjugate with a second compound comprising an azido group and a label, such that a bioorthogonal reaction occurs between the optionally substituted alkynyl moiety and the azido group.

11. The method of claim 10, wherein the label comprises a fluorescent agent.

12. A kit comprising:
a first compound of claim 1; and
a second compound comprising an azido group and a label.

13. A method of measuring protein synthesis comprising:
contacting a cell with an effective amount of a first compound of claim 1, such that the first compound is covalently bound to the C-terminus of one or more nascent polypeptides in the cell to form one or more polypeptide-first compound conjugates, wherein each one of the first compound and the conjugates comprises an optionally substituted alkynyl moiety;
contacting the cell with a second compound comprising an azido group and a label, such that a bioorthogonal reaction occurs between the optionally substituted alkynyl moiety and the azido group to form labeled nascent polypeptides; and
determining the amount of the labeled nascent polypeptides by fluorescence, spectroscopy, radio detection, autoradiography, immunostaining, ligand binding, chemiluminescence, immunoassay, enzymatic assay, isolation, or purification in the cell to measure protein synthesis.

14. A method of identifying an agent that perturbs protein synthesis comprising:
contacting a cell with a test agent;
contacting the cell with an effective amount of a first compound of claim 1, such that the first compound is covalently bound to the C-terminus of nascent polypeptides in the cell to form nascent polypeptide-first compound conjugates, wherein each one of the first compound and the conjugates comprises an optionally substituted alkynyl moiety;
contacting the cell with a second compound comprising an azido group and a label, such that a bioorthogonal reaction occurs between the optionally substituted alkynyl moiety and the azido group;
determining the amount of the label incorporated into the nascent polypeptides, wherein the amount of the label indicates the extent of protein synthesis; and
identifying the test agent as an agent that perturbs cellular proliferation if the amount of the label incorporated into the nascent polypeptides is less than or greater than the amount of the label measured in a control in which a cell is not contacted with the test agent.

15. A method of identifying a nascent polypeptide comprising:
contacting a cell with an effective amount of a first compound of claim 1, such that the first compound is covalently bound to the C-terminus of a nascent polypeptide in the cell to form a polypeptide-first compound conjugate, wherein each one of the first compound and the conjugate comprises an optionally substituted alkynyl moiety;
contacting the cell with a second compound comprising an azido group and an affinity label, such that a bioorthogonal reaction occurs between the optionally substituted alkynyl moiety and the azido group to form an affinity-labeled polypeptide; and
affinity purifying the affinity-labeled polypeptide.

16. The compound of claim 1, wherein $R^A$ is a $C_{1-3}$ alkyl divalent moiety.

17. The compound of claim 1, wherein $R^1$ is ethynyl.

18. The compound of claim 1, wherein —$R^A$—$R^1$ is of the formula:

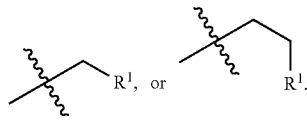

19. The compound of claim 1, wherein —$R^A$—$R^1$ is of the formula:

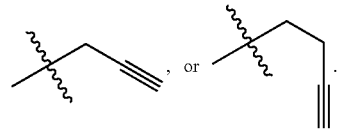

20. A compound of Formula (I):

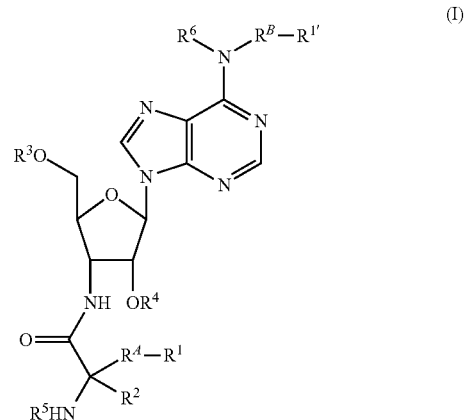

wherein
$R^A$ is a bond, an optionally substituted aliphatic divalent moiety, an optionally substituted heteroaliphatic divalent moiety, an optionally substituted aryl divalent moiety, or an optionally substituted heteroaryl divalent moiety;

$R^B$ is a bond or a $C_{1-6}$ aliphatic divalent moiety;

$R^{1'}$ is optionally substituted alkynyl;

$R^1$ is hydrogen;

$R^2$ is hydrogen or $C_{1-6}$ aliphatic;

$R^3$, $R^4$, and $R^5$ are each independently hydrogen or a protecting group; and $R^6$ is hydrogen or $C_{1-6}$ aliphatic;

or a salt thereof.

21. The compound of claim 20, wherein $R^{1'}$ is propargyl or ethynyl.

22. The compound of claim 20, wherein —$R^A$—$R^1$ is a side chain of a naturally occurring amino acid.

23. The compound of claim 20, wherein $R^A$ is an aryl group.

24. The compound of claim 20, wherein $R^A$ is an -alkylaryl group.

25. The compound of claim 20, wherein —R$^4$—R$^1$ is selected from the group consisting of:

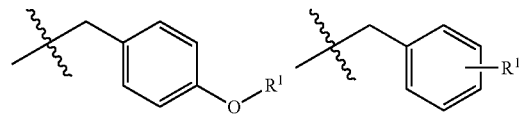

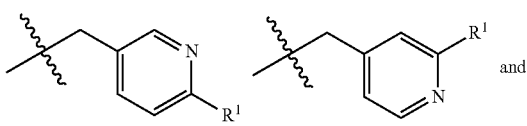

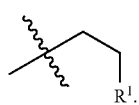

26. A method of labeling a polypeptide comprising:
   providing a conjugate of a polypeptide and a first compound of claim 20, wherein each one of the first compound and the conjugate comprises an optionally substituted alkynyl moiety; and
   contacting the conjugate with a second compound comprising an azido group and a label, such that a bioorthogonal reaction occurs between the optionally substituted alkynyl moiety and the azido group.

27. The method of claim 26, wherein the label comprises a fluorescent agent.

28. A kit comprising:
   a first compound of claim 20; and
   a second compound comprising an azido group and a label.

29. A method of measuring protein synthesis comprising:
   contacting a cell with an effective amount of a first compound of claim 20, such that the first compound is covalently bound to the C-terminus of one or more nascent polypeptides in the cell to form one or more polypeptide-first compound conjugates, wherein each one of the first compound and the conjugates comprises an optionally substituted alkynyl moiety;
   contacting the cell with a second compound comprising an azido group and a label, such that a bioorthogonal reaction occurs between the optionally substituted alkynyl moiety and the azido group to form labeled nascent polypeptides; and
   determining the amount of labeled nascent polypeptides by fluorescence, spectroscopy, radio detection, autoradiography, immunostaining, ligand binding, chemiluminescence, immunoassay, enzymatic assay, isolation, or purification in the cell to measure protein synthesis.

30. A method of identifying an agent that perturbs protein synthesis comprising:
   contacting a cell with a test agent;
   contacting the cell with an effective amount of a first compound of claim 20, such that the first compound is covalently bound to the C-terminus of nascent polypeptides in the cell to form nascent polypeptide-first compound conjugates, wherein each one of the first compound and the conjugates comprises an optionally substituted alkynyl moiety;
   contacting the cell with a second compound comprising an azido group and a label, such that a bioorthogonal reaction occurs between the optionally substituted alkynyl moiety and the azido group;
   determining the amount of the label incorporated into the nascent polypeptides, wherein the amount of the label indicates the extent of protein synthesis; and
   identifying the test agent as an agent that perturbs cellular proliferation if the amount of the label incorporated into the nascent polypeptides is less than or greater than the amount of the label measured in a control in which a cell is not contacted with the test agent.

31. A method of identifying a nascent polypeptide comprising:
   contacting a cell with an effective amount of a first compound of claim 20, such that the first compound is covalently bound to the C-terminus of a nascent polypeptide in the cell to form a polypeptide-first compound conjugate, wherein each one of the first compound and the conjugate comprises an optionally substituted alkynyl moiety;
   contacting the cell with a second compound comprising an azido group and an affinity label, such that a bioorthogonal reaction occurs between the optionally substituted alkynyl moiety and the azido group to form an affinity-labeled polypeptide; and
   affinity purifying the affinity-labeled polypeptide.

32. The compound according to claim 1, wherein the compound is of formula (II-a):

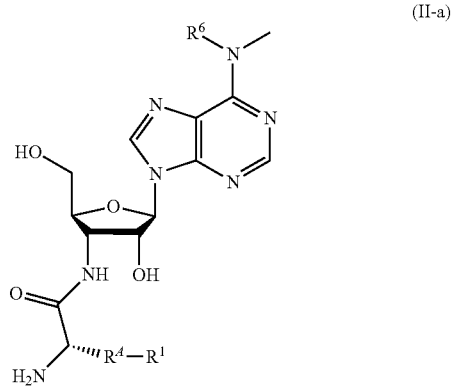

or a salt thereof.

33. The compound according to claim 1, wherein the compound is of formula (III-a):
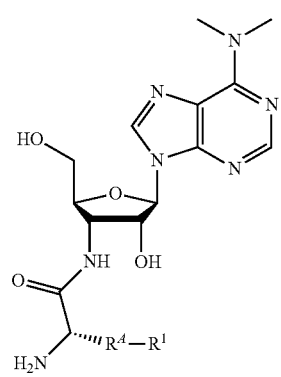
(III-a)
or a salt thereof.
34. The compound according to claim 1, wherein the compound is of the formula:
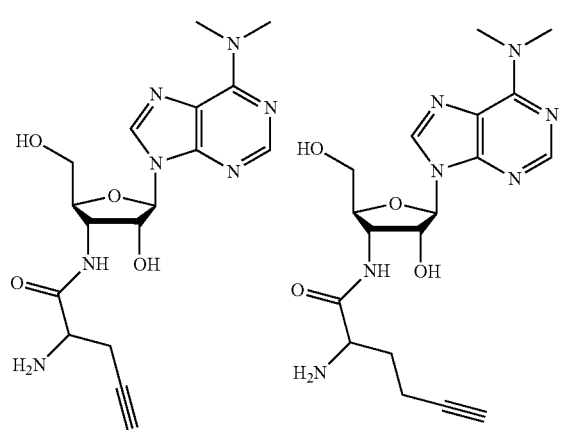
or a salt thereof.
35. The compound according to claim 1, wherein the compound is of the formula:
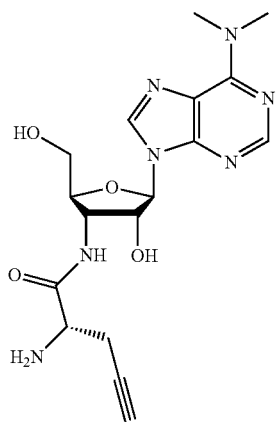
or a salt thereof.
* * * * *